(12) United States Patent
Seebeck et al.

(10) Patent No.: US 7,785,849 B2
(45) Date of Patent: Aug. 31, 2010

(54) **CYCLIC NUCLEOTIDE-SPECIFIC PHOSPHODIESTERASES FROM *LEISHMANIA* AND USES THEREOF**

(75) Inventors: Thomas Seebeck, Ortschwaben (CH); Andrea Johner, Niederwangen (CH); Yasmin Shakur, Falls Church, VA (US)

(73) Assignees: University of Bern, Bern (CH); Otsuka Pharmaceutical Co., Ltd., Tokyo (JP)

( * ) Notice: Subject to any disclaimer, the term of this patent is extended or adjusted under 35 U.S.C. 154(b) by 778 days.

(21) Appl. No.: 10/570,350

(22) PCT Filed: Sep. 3, 2004

(86) PCT No.: PCT/IB2004/003990

§ 371 (c)(1),
(2), (4) Date: Mar. 3, 2006

(87) PCT Pub. No.: WO2005/023856

PCT Pub. Date: Mar. 17, 2005

(65) Prior Publication Data

US 2007/0292847 A1      Dec. 20, 2007

Related U.S. Application Data

(60) Provisional application No. 60/500,244, filed on Sep. 5, 2003, provisional application No. 60/504,070, filed on Sep. 19, 2003, provisional application No. 60/582,584, filed on Jun. 25, 2004.

(51) Int. Cl.
| | |
|---|---|
| *C07H 21/02* | (2006.01) |
| *C07K 14/00* | (2006.01) |
| *C07K 17/00* | (2006.01) |
| *C12P 21/04* | (2006.01) |
| *C12N 9/00* | (2006.01) |
| *C12N 15/00* | (2006.01) |

(52) U.S. Cl. ............... 435/183; 435/70.1; 435/71.1; 435/71.2; 435/320.1; 536/23.1; 530/350

(58) Field of Classification Search ............ None
See application file for complete search history.

(56) References Cited

FOREIGN PATENT DOCUMENTS

WO         WO0222661 A2 *  3/2002

OTHER PUBLICATIONS

Rascon et al. Molecular and Biochemical Parasitology 106:283-292, 2000.*
Invitrogen Catalog, 1997 Primers for First Strand cDNA synthesis Under cDNA synthesis and Libraries Chapter.*
BLAST two sequences: alignment between Seq ID No. 3 and protein sequence of LmjF15.1480 (www.genedb.org) cAMP phosphodiesterase of *Leishmania major*. 2 pages.*
cAMP phosphodiesterase of *Leishmania major*—LmjF04.0030 http://www.genedb.org/genedb/Search?organism=leish& name=LmjF04.0030&isid=true 2pages.*
cAMP phosphodiesterase of *Leishmania major*—LmjF15.1480 http://www.genedb.org/genedb/GeneBasket?action=add& id=LmjF15.1480&organism=leish 3 pages.*
Montalvetti et al. Biochem. J. (2000) 349:27-34.*

* cited by examiner

*Primary Examiner*—Robert Mondesi
*Assistant Examiner*—Oluwatosin Ogunbiyi
(74) *Attorney, Agent, or Firm*—Finnegan, Henderson, Farabow, Garrett & Dunner, LLP

(57) ABSTRACT

The present invention relates to novel amino acid and nucleic acid sequences of cyclic nucleotide-specific phosphodiesterases from the parasite *Leishmania major*. The invention also relates to nucleic acid constructs, vectors, and host cells comprising the nucleic acid sequences as well as methods for producing and using the amino acid and nucleic acid sequences. The invention further relates to the use of these sequences, and of antibodies directed against these sequences, in the diagnosis and treatment of disorders related to the infection of *Leishmania major*, including the identification of compounds that form complexes with the polypeptides and nucleic acids of the present invention.

16 Claims, 62 Drawing Sheets

```
  1  MLDFLEQLQQ LASVYAICGN AVSVMAGMSD TAEELTFRSY DSLEGASYIC
 51  NLNEKALHTA KASLCDNADW SSFFREVQLA FNSGRVTVQP GNAHRVAVNA
101  AAPVSADSKG LACSMEVHCL SGSGEKCATF VLERTTEDQQ KYILESMLQA
151  HHMYNHPKEY EQKLLHIMEA KEIACTKREA LDRELVALND NLTRNKHKQK
201  INNERKEELL KKLGGYSTEN TGNPWQAIQE QQQRTAGENT KSRLPSPLGN
251  RTCKDFDLVL FRMIKSRWLS PEQCDASSPA NRVVQPYSKE DLAIQVSQLS
301  GSRAAIWKAL DSIDSWSYRV FDVQAAMSGD DYLSLSTQTH GGSLLITMYA
351  LLCMHDFLQK FKIDEQIALN WISAVEASYH GNPYHNSMHA ADVLQITDFI
401  ITQGGLAKRC DLSDIQVFSA LLAASIHDFD HPGINNNFHI KTGSYLATLY
451  NDRSVLENLH VSSVFELMKN PAFNILASFS DEQHHEVRET MIEMVLATDM
501  GSHGKYVASL KGKMQEHSSF TQTAEQNLCL AIALKMADIS NCGRPLDIYL
551  RWGAKVSDEF YQQGDRERNL GLECSPFMDR LQPSLAKSQI AFMNYIITPF
601  FEQVAELLPD MRFAVALVEE NKAYWANHDD S*
```

*FIG. 1*

```
  1  TGGCTACCGC CCTGCCAGCA AGTACCGGAG GCGCCGGCTC GTTTCTTTT
 51  TGTTGCCTTT TCCAAGCAAC TGACGGGACA CGTTTCAGTG CATGCGCATT
101  ACCACGATGC TTACGGTGAA GCACGACCGT GCACATTCAC TCAAGGTATT
151  GTGAGCGCGA ACAAGCAAAT CCCAAAAACAA GCCGCCTGCG TATGTCTCTG
201  CAGTTTCCCA TGTGCAAATC TACCTGTCTT CGACTCTGCC GCCATCCTTC
251  TCTCTTTCCT AACTCTGTTT CTCTTTCTCT GCAACAGAGC TGAAGTCTGA
301  CGCGCTTCTC GTTCTTTCGT TTTTTTTCCT CTTCCCCCTT TTTTTTGCAG
351  CTTCTCCCCA ACACGGTTGG TCGACCGCTC CAGAAAATAA CAGCAAGAGG
401  CGAAACAGTA ACGNAAACAC CCNACCCACC CACCCACTCA CCAAACAGGC
451  GGCCGAAAAA AAAGACTCCC CTCTGAACTT TTGCTTTTCG TTGCTCTTCC
501  TGCGGGTGCCG CGCTCTAGCA GCGGCAGCGA TGCTCGACTT TCTTGAGCAG
551  CTGCAGCAGC TGGCAAGTGT GTACGCCATC TGCGGGCAATG CTGTCTCCGT
```

*FIG. 2A*

```
601   GATGGCGGGG ATGAGCGACA CGGCAGAGGA GCTGACGTTC CGTTCCTACG
651   ACAGTTTAGA AGGCGCCTCC TACATCTGCA ACTTGAACGA GAAGCTCTT
701   CACACAGCGA AGGCCTCGCT CTGCGACAAT GCCGATTGGA GCAGCTTCTT
751   TCGCGAGGTT CAGCTGGCAT TCAACTCGGG TAGAGTAACC GTGCAGCCTG
801   GAAATGCTCA TCGAGTCGCC GTTAACGCCG CCGCGCCAGT TTCCGCCGAC
851   TCTAAAGGCC TAGCATGCTC GATGGAGGTG CATTGCCTGT CGGGGTCAGG
901   GGAGAAGTGT GCAACCTTTG TGCTTGAGCG AACCACGGAG GACCAGCAGA
951   AGTATATTCT CGAGAGCATG CTGCAGGCAC ATCACATGTA TAACCACCCG
1001  AAGGAGTACG AGCAGAAGCT GCTCCACATC ATGGAAGCCA AGGAGATAGC
1051  GTGCACGAAG CGGCAGGCAC TTGATCGTGA GCTGGTCGCG CTGAACGATA
1101  ATTTGACACG CAACAAGCAC AAGCAGAAGA TAAACAACGA GCGCAAAGAG
1151  GAGCTTCTAA AGAAGCTCGG CGGTTACAGC ACAGAGAACA CGGGAAATCC
```

FIG. 2B

```
1201  GTGGCAGGCG ATTCAGGAGC AGCAGCAGAG GACAGCTGGC GAGAACACGA
1251  AGTCTCGGCT GCCGAGCCCG CTCGGGAACC GCACCTGCAA GGATTTTGAT
1301  CTTGTCCTGT TTCGCATGAT CAAGAGTCGG TGGCTGTCAC CGGAGCAGTG
1351  CGACGCATCC TCGCCCGCGA ATCGCGTCGT GCAGCCGTAC TCCAAGGAGG
1401  ACCTCGCGAT CCAGGTGAGC CAACTCTCAG GTAGCCGAGC TGCGATATGG
1451  AAGGCACTGG ATTCCATCGA ACTACCTCTC TACCGCGTGT TTGATGTCCA
1501  GGCGGCTATG AGCGGTGACG ACTACCTCTC GCTCTCGACG CAGACGCACG
1551  GCGGGTCTCT CCTGATAACC ATGTACGCAC TGCTGTGCAT GCACGACTTT
1601  CTGCAAAAAT TCAAGAGATTGA CGAGCAAATT GCGCTCAACT GGATCAGCGC
1651  AGTGGAGGCG AGTTACCATG GCAACCCGTA TCACAACTCG ATGCACGCCG
1701  CGGATGTGCT GCAGATTACG GACTTCATCA TCACACAGGG AGGGTTGGCG
1751  AAGAGGTGCG ACCTAAGCGA CATCCAGGTC TTCTCTGCCT TGCTGGCTGC
```

FIG. 2C

```
1801  CTCGATCCAT GACTTCGACC ACCCTGGCAT CAACAATAAC TTCCACATCA
1851  AGACAGGCAG CTACCTTGCT ACGCTGTACA ACGATCGCAG TGTCCTGGAA
1901  AATCTGCACG TGAGCAGCGT TTTCGAGCTC ATGAAGAACC CAGCCTTCAA
1951  CATCCTAGCC AGCTTCAGTG ATGAGCAGCA TCATGAGGTC CGCGAGACGA
2001  TGATAGAGAT GGTGCTGGCG ACGGACATGG GCTCTCACGG AAAGTACGTG
2051  GCGAGTCTGA AGGGCAAGAT GCAGGAGCAC TCTAGTTTCA CTCAGACCGC
2101  CGAGCAGAAT CTCTGCCCTCG CGATTGCTCT GAAAATGGCC GACATTTCAA
2151  ACTGCGGGCG CCCGCTTGAC ATTTACCTGC GCTGGGGAGC GAAGGTGTCG
2201  GATGAGTTCT ACCAGCAGGG CGACCGTGAG CGCAACCTGG GCCTCGAATG
2251  CAGTCCCTTC ATGGATCGCC TTCAGCCGAG CCTTGCGAAG AGCCAGATTG
2301  CCTTCATGAA CTACATCATC ACTCCCTTCT TTGAGCAGGT GGCCGAGCTT
2351  CTGCCCGATA TGCGCTTCGC GGTGGCTTTG GTGGAGGAAA ACAAAGCGTA
```

FIG. 2D

```
2401  CTGGGCCAAC  CACGACGACT  CGTAGAGACA  TCCCACTCAC  CGCCTTTCGT
2451  GGCGCACCTG  TTTCCTCACC  GCCCCCTTTT  TTTCGTGGTG  ACGCGGCTCTT
2501  TGTGGATACA  CACACACACA  CACACACAGA  CACAGTCTTC
2551  GTTCTACCTA  GTGTCACGTC  GGTTTCTTC   ACCGGAAGCG  GGGCAAGGAT
2601  GTATATATCT  ATTTCTCTCT  CTTGTTGCAG  CTCCCACCTT  CACTGCCTCC
2651  CTCGTTGCCT  CTCCTTGCGA  TGTATTATTA  TTATTTTGT   TGTTCTCGCC
2701  GATTATTTCT  TCCACGCTGA  TGGGAAGGTG  TAAAAGGCGG  AGGAGAAGGG
2751  GGAGAGGAGT  TGAAGGAAAA  AGGAGTAACA  CCAACTGGAA  CCCTCACTCG
2801  TTTTCTTTTT  CGCCTTTTTG  TTCCGTATCC  GCTCAGTCTC  CTTAATTTTT
2851  TTTTGTGGTA  TGAATTTGCT  GAGTTGTCCT  CTTGAAGTGC  GAACACTTGT
2901  AATCCCTCTG  GTGGCTTTTG  ACACGTGTGT  GATGAGCTCC  ACACTTCTCT
2951  TCTTGCTTCC  TTCCCACTTT  CTCGTCTTCT  CACCCTCCAT  TCTTCACCTC
```

FIG. 2E

```
3001  ACATGTGCAT CTGGCGTGTG TGCACGTATG CGTAACGAGC CTGTCGCACA
3051  CGCTTCTTCG CCTCTCTCAT GCTTTTGTTT GTGCATTTCC TTCATGCCAA
3101  CCTCCGTGTT TTTATGTTCT ATTTTTACGC TTGCTTTCAA CCCTGTGTGT
3151  GTGCTTCCGC CGCCGTTTTT ATTTTTCCCT CCTCAGTGGT TGTTTGTGGT
3201  GGTACCCGAA TTGCCGTTTC GCACATACGC GGGCTTCGCC TTGACGAGGT
3251  TTACCTCTCT CTTCCCTTCC CTGGGTTTGT CGCAGACCGC CCTAGCTCCC
3301  TCCCTTCCCC ACATCCCCTCC GCCCCCTTTG GCCCCCCTTG TGCAAAACAA
3351  GAAAGAGAGA GGGCACCGTC CACCTCCTTC GGTTCTCTCT GTTTTCTTCG
3401  CCTCTTCGAT GATGCGCTTA GTTTGACTGA CGCGGTGCAG CGGGTAGCGT
3451  TTACATGCTG TTGCCTTTTT TTTTGTATTT CCTTTTGACG ATTATGGTTC
3501  TACGCGGCTT GCGTTTGGCG GCGACAAGCC ACTACTCTGT GAAGAAAAAC
3551  AAACAAGAAA AGGGCGTTGTC AATGCGAAAG GGTGCGCTAC TGGAGATGGA
```

FIG. 2F

```
3601  GATGAGCGTT  GGTGTCATCT  TCGTTGGTGC  TTCCCATGCC  TGAGTTCATG
3651  CATTGCGACT  TTAGGCCTTA  TCCAAGGTCT  GGCCGGCACT  TCTCCACAAG
3701  GATTTTGTCA  CTGCCGTATG  AACTCGGGTAG  CCAGGCTATG  ATTCCCATCT
3751  CTTGCTTCTG  GAGCACAGCG  CAACCCCCCC  TTTCTCTCCT  TCTCTTCTCG
3801  AGTCCAACGG  CTCTTCTCCC  TTTCTCTCCT  CTTCTCTTCC  GCTGCCCGCC
3851  TTCGTCGACG  TTTCTGGGTT  TCATGCCACT  CCCCCTTTCC  CTGCACGGAG
3901  GAAAAGCAGA  AGTACAGTTT  CTCAAAATCT  TGTCTCTACA  CGGCTTGCCA
3951  GTGTCCGCAC  TCGTCCCGTT  ACTTTCACAC  GGCGCACACG  ACGACACTTA
4001  CCCCCCCCCC  TACACACACA  CACACACACA  CACACACACA  CACACACACA
4051  CACTGCACAG  TGTCACGGTG  CATCATCTGA  AACATTTTTC  CTTTTTTCCT
4101  TTTCGCGGAA  CACATTCTTT  CTTCCTATTA  CTATTTGCT  TACCCTTGTT
4151  GGCAGCCTGC  TACCATTTTT  TTGTTTCCGT  TTCCTTGTGT  TGGCGATTAT
```

FIG. 2G

```
4201  ATACATATAT  ACATATATGT  ATATATATAT  ATATATGTGT  ATATGCTTCG
4251  ATCATCGTGG  GTCTTTGCAT  CCGTGTGCAC  CTCTCGCAAC  ACACTTCTGT
4301  CAGGCGCAATT GTCTTTTTGA  AAAGTAGATT  GTTGGCCACA  CACTCTGCGA
4351  TAGCGCGTTT  TCCAGGGACG  AGCTGCAGTC  TGCACACTTC  ACCGCCTCAT
4401  CACCTTGACG  TTATTATTAT  TATTTTAAGC  TTCCCGCAGA  GTTTGTCTGC
4451  AAGTTGACCC  AGAGTCTTTT  ACTCGAGCGC  ACACCATCAA  ACATCAGCCA
4501  TGCATCTTTC  TGAGCTTTGC  CGGGACTCCA  ACATCGACGT  GATCATCGCT
4551  CGCCTTCGCC  AGGTAGCACC  CCTAGAGCCT  GCGCCGGCTT  TCTCTTTGTC
4601  CGAAGGAGCA  GCAGATGACG  ACACAACTCC  CGCAACTGGA  CACTCGGACT
4651  TTCATGGGCT  GTGGAGCTAT  CAGGACAATG  ACGGGCGTAC  AGCCTTCCAT
4701  TGGGCCATAG  CGCTCAAGAA  CTTCGACCTG  GCTCGCAAGT  TGATGCAGGC
475*  ACCGTACAAT  TCGCCTGTGC  TGACCGAAGA  TGAGGAGTGG  AGCACACCGT
```

*FIG. 2H*

```
4801  AATGTTTGAC CGGTCGAAGA ACACGAGCTG GCGCGTGGGC AGATTGGCTT
4851  CATCGACTTC GTAGCTGGCA AGTTCTTCCG GGATATTGTG GGCAACCTAT
4901  TTCATGGAAT GCAGTGGTGT GTGGACACGG TAAACTCCAA CCGCGCAAAG
4951  TGGCAAGAGA TCCTGGATGG CCGCCGCGAC TCCATCCGAT CCTCGATTGT
5001  TTAAGGCATC GGTCCCGCGG TATCGTTGAT GCCGTAATAG CGCGCGGAAG
5051  TACTCACGGC GAATGTCTTT CGAGAAGTGA AAGCGGGTGAG CTCACTTGTC
5101  ACTATGGACG GATGAGTGCC GTTGGTCGCC GCTCTGCTGT GCGTGTCTAC
5151  GCGTCTTATC CCCACCTCAG TATGTGCACC GGGCCGTCAT TTCCCTTTGT
5201  ACCCGTCGCT GTATCCGCGA CGGCGGATGG TTTGTGTGTT GGTGAGTCTC
5251  CCTCTCTCTG CACCAGGGCC TGTTCTGGTT GATGGGCGCC TCTCGCACTG
5301  CTGAGGACAA GGTGTGGCAC ATGTGGGCGT GTGAGTCGTG TTTTTTTTTT
5351  TTGGCTCTCG TCTTGTCTCC TCTCTCCCTCG CTATTAGCCC TTTTCTGAAC
```

FIG. 21

```
5401  AGACCTCTCT CTCTCTCTCT GCTCGTCTTT CGGAGGAGTG GTTTGCCGTT
5451  GAAGGCTGAA CGGTACGAAG GGGGAGGAGT GAGCAGTGCA GGTGCACACA
5501  CACGCACCAC ACCTAAATTCT CTCTTCATCC GCCTTTCCTT TTTTTCCGGT
5551  GTGTGTCCCG AAGATGGTTT CCTGTCTTTG CATCCGTTTC TCTCCCCCTT
5601  TTTTCGTGTG TCTGTCTTTT GTTGTTCGTC ACGAATCTCA CCCGCCTCCC
5651  TCCCCCCTCT CCCATTTTTT CTCTCGTAGG TGTGTGCATC TGTGCTCCTG
5701  GTGAGACGGA GTGGAGTGGG GGCACCCCGC AGCGCGTGGC ATCTCTCCCC
5751  CCCCCCAGGT GGGGGGTCAT TCGTGCACCC AAACTCTGTC TCTGGGGAGG
5801  AAGCTCAGCG GCGCACCCCC ACCCCCACCC CCACCCTCTC CCTCCTATAT
5851  CCCTGCCAGT GCGGAACCGC TTCTCCTGGC GACAGGGTCA AGCACCTATA
5901  ACGCAGGGAG GACAGAGCAA GATGTCGCTG CGGATGTCGG CCGTCAGGTG
5951  CCGGATGGCG TGGCGCCGGA GCGACCTGCG ACAGCGCACA CGCACGATTC
```

*FIG. 2J*

```
6001  ATGTGATGGG  CAGAGTGCCG  GCGTGACTCG  AACGCATCCC  ACCCCCGGCC
6051  CTCACACTGT  CCTGCTGCTG  TGGGGAGCCT  GTGCCATCGC  GATGGAATCG
6101  CACCGTGTGG  CGACCGGCAC  AACGTGAGCG  GCTGTGGGGC  GACCTGTGAG
6151  GCGGGGTGGG  TGGGTGGGTG  GCGGGTAGAG  TTCGAGGCTG  AGGCTGTGCC
6201  CTCAGATGGC  CGAGTTGGCG  CGTTGCGGTC  ACGTGTGTCT  CTGCAGCTGC
6251  TTCGCACCAG  GCGATAGAGG  CCTGTGACAG  GGCCGGTGCA  AGAGTGGGGC
6301  TCGACCTCAT  GTTGCATGAC  AGAGAAATGA  ACATGCTGTA  ACTCCCCTCT
6351  CCTTGACTCA  TTTCCATCTC  TTGTGTCACC  TACTACCTGT  CCTTCTCAGT
6401  GTCTTGGTGC  ACTTGTGACG  TTCTCGGGTG  TCTCCCTCTT  TCTTTTCTTC
6451  TCGAAGTTTT  TTGGGTCTGC  AGAGAGGC    GATGGGAGGA  GGAGCAGCCA
6501  GGCTTGCGTT  GTGTGATGTC  GAGAAGAACA  ATGTAACAGC  TCTTCTCTCG
```

FIG. 2K

```
6551  TTGTCCTCCT  TCCTCCCGCT  TCTGTTCGGC  GAGGAAAACA  GCAGACTTGT
6601  GTAGCACAAG  ATGCTGCTGG  CGCCTGCTGT  GTGACATGTG  CGAGGAAGCC
6651  TCGCGGCAAAC  CGTTTGTGGT  CTCTGGAGGG  GGTACTGCGA  GCGGGAGGAC
6701  AGGGCGAGGC  AACGTGTGCG  AGATAAGGTC  GTGGCACAGA  GAGGATACGG
6751  CTATGAGAAG  GCTGTGTGCT  GTTGGTGTTT  CCTCAACGTT  CGTGCTAAAG
6801  GTCCGTCCAA  AGGTGAGGAA  GTTGGGACGA  GGAAGCATGC  ATGGACGGTC
6851  TCGTGGCCTC  ATCACCTCCT  TTCGGTGCCA  TCATTACCAC  CCCTCGCTCC
6901  GCTTCGCCTG  CACCACAGTG  AGCGTGCTTT  GGAGGCCATC  GCAACCCGCA
6951  TGCTCACCAC  ACCCGACATT  GCCGCCGTAG  TGCGTCCTGT  GACCGCCTTT
7001  CCGTCCAGCG  CTGGTCTCTA  CTCCTGCAGC  AATAGCGGACT  ACCACAGCCA
7051  CAAGGCGGTG  GAGTACGTCT  GCCGCACCCT  GCACGCTGCT  AGCGCCGTGT
7101  CATTTCAGGA  GGTGGTGTCG  GCGATACCGG  TGTTTGTGCT  GGATGTGCAG
```

*FIG. 2L*

```
7151  CCGCAACACA CTGTCGTGGA TCTCTGGCGG GCACCTGGCA GCAAAACAGT
7201  GCAGGCCTTG GACACCATGC TGAGCGGTGG GTGGTCTGCA GACGTCTGTC
7251  GAGGGGTGCT CATCGCCAAC GAAAAGGACA GAGTGAAGGC GACGCAGACA
7301  CTTCCGGCGC GGCTGAAGCG CTACCACGCC CCAAACGTGA TGACTACCCG
7351  ATGCGACGGT GTGCAGTGGC CTCGTTTGTA CTTTAACGAT CCTACGAACC
7401  CAAGCAGCGA GCCGCAAGAA CGGCGGTTTG ACCGCATCAT CTGCGACGTC
7451  CCGTGCAGCG GCGACGGCAC CATCCGCAAG GAGTGTTCCA TCGCCACAAC
7501  ATGGTCGGCA AGCTACGTGA AGTCCCTCGT GCCAACCCAA CGTGCCGTTGC
7551  TGTGCCGCGG CCTTGACCTC TTGGCCACAG GGGGCATTCT GGTTTACAGC
7601  ACGTGCAGCA TGAATCCGAA GGAGGACGAG GAGGTGGTTT GCGTCGGGTT
7651  GGAGGCTTTC GGCGACAGTG TCGAGCTCAT CGACGTGAAT GCGGTTCTAC
7701  AGGAGAAGGG ATTTCACCTG CACTCGGCAG GAGGGATTCT CTCCCCGAAT
```

```
7751  GTGGAGGGGA  TGCAGCACCC  GGTGCTGCCG  CCGACGTACG  ACGGCAACAA
7801  GGTCCTGCGC  ATTTGCCGC   ATCGTGATGA  CACCGGCGGG  TTCTTTGTGG
7851  CGGCTTTCCG  CAAAGCAAAG  CAGCCAGACC  GGACGGGCGCC CACAGTGATT
7901  CGACACAAGC  TGAACCACTG  GACGAAAGGC  AAGCTGTGGG  CGCCAGTTGG
7951  CGTCGAGGAC  GAGGCGTGGG  CCAACATATC  AACCTTCTAC  GGCTTTGACC
8001  GCCGCGACGA  AGCGAACTTC  GTCTACTATG  ACGCCACTAG  CTCTTCGTCC
8051  GGGAAAGGCC  TCGTGCCTCT  GTATCACCTC  AATCCAAATG  GTGGGCCTAT
8101  ACGCCGCATC  GTGCTCTCGA  CTCCGGCGCT  GGCGGATATG  GTGCTGCGCA
8151  CACGTCCGTA  CAAGGGCCCT  GGCGTGGAGG  TGGTGTCCGT  CGGTATGCGC
8201  GCGTTCGAGG  CATACGACGG  AAGGTTTTTG  CCAACTGCGG  CCTGCCGGTG
8251  GCGCGCCGTC  GTTGAGTCCG  CCTCTTTTTT  GGCACCGCGC  TTTACTGCCC
8301  GAAGGCTGCA  CTTCCACGTT  TCGAAGCACA  AGCAGCTACT  CGAGGATCTG
```

```
8351  CTCCGAAACG GCCACGTTTA CACGCGAGAT CACTGGAGGA CAGTGTTGGG
8401  TGGAGATCCT GCTGTTGTAG CCGCTAACGC GAATCCGAAG GCGCTGGTCA
8451  AGCCTGGCAG CCGACTCGAG GCGTTGCTGA CGCAGGGCAG TAGTGAATCT
8501  ACCATCTCTG ACGAGGAGGT GGCGGTGCTG CTGACAAGCC ACGTGGAGGT
8551  AGGGTGCGTT TTGGTGGGCA TCCTCTTCGA CGAGCCGACC GATGCAGCCG
8601  CTGGTCCGTG GTACATGAGC GCGACGCTGA GCGGGCACAA GCTGGAGCTC
8651  GCCATCGATG GCTCTCTGCG TGCGTTCGGG TTGATGACGT TTTTTGGCAT
8701  TCACGACGTT GAGCGTGGCT CGCTGGCCGG CAACAACATC GGCAGTGCGG
8751  TCGCAGAACGA AGAGCCTGAG GAGCAGGCAA AGGAGGTGTA GCACCGGAAG
8801  CTTCACACGG CGTGGTGTCG CATAACTCCT GTGCTTTCAC TGCAGTGGCT
8851  TATCGAGACT ACAGTTACAT TCGATTTCAA TCGAAGAGGC CATGGAGCC
```

FIG. 20

```
8901  GTCTGCACTG TTGATCCTTC TCCTTTTTTT GCGTATGCGT ACTATTCTAA
8951  GCGAGTAACC GCATCTTCAC TGACTAAACC GCCAAACTTC ATGAGTCGCA
9001  GGAGCAGTAT AATTGTCGCC GAGCCCCTCA TCACGTGTAT GAGGGGCGAA
9051  ACGAAAAATG ATGAGAGGCG ATGCATGGCT TTTCAATAGC CGTGACGCGT
9101  CCGTGTGTGC GCTGGATTCG CTGCTCTGGC TTTTCCACGA AGGGGATGGA
9151  TCGCGCAATA CACGCGCGTT GGAATGCACG GCCATTCTCG CTCTGTGCTC
9201  CGGCGTCCTC TTGAGGGTGC GGCTGGTGTT GGAGTGGGGT TGAGGGTCGC
9251  CGAGAAGACG CGTGCTTTCT GAACAGCTCA CGAGCAGAGC CTCTGCTACT
9301  TGAACCAACT CTCTTCCACT ACGAACGCTC TTTCGGTATC TTCAATCCAT
9351  CTTCTCTGTC TTGCTATTCG GTCTTCGTCC ACCTTGGCTT CACGAAGAAG
9401  GGAAGCCAAG CCTCAGCACA CAGCAACATC CGCACAAGCC GTACCCTTTA
9451  CCACCTCTGT GGTTCCACTC CATCTCCTTC ACTGGTGTAC ACGATATAAT
```

*FIG. 2P*

```
9501   CGGGGTTTTT CTTCTCTGTT GTTGCCCTCC TTTCTCTCTC GTGCTCCTGT
9551   TGGGCCATTT CGATACGCGC AAGGGTCGCT ATTTCGTGCT TTACATCTTG
9601   CGTTGGTCTC GCCCCGATTG CTCGTGGCAT TTTCTCGTCA TCGTTTTTCC
9651   GTCTCCGTAC GTTGCCGTGT TTCTCTTTAC TTCTATGGAG GCACGTTGTG
9701   CATCTTCGCC CCTCTCCGCT TCTTTGTCAG ACAGCGCGGC CAAGGCGAGG
9751   TTGGTCGGGT GCGGGGGCGG TCTCATTTCT CCATAGCTCC GTGCTTTTAA
9801   TACACCCTCC TTCCTCCTCC CTTGTTTCCA TAACTCCTTA TTTTCTTGTT
9851   TCTGGGGGGG GTTCGACCCC TTTTTGTGTA ATCAGCACCA TGCAGGTCGG
9901   TGTATATGAC AGAGATGATC AGATGTGCCA GTATGAGGGC TGCACGGAGA
9951   TCGATCTGCT GCCTGCCCGG TGCTCCAACT GCGACAAGCG ATTCTGCACC
10001  CACCATCTCT CCCACAGCGC ACATCGCTGT CCGGCCGTGA CGGATGTGCG
```

*FIG. 2Q*

```
10051  GGTCGGGGACG TGCCCCATAT GCTATCGGGT TGTACCGTTG GAGTACCCGC
10101  GCCAATGCAT GGACGAGGCG GTGTCCCGGC ACATTGACCG AGGATGTCGC
10151  GATGTACCGC AGGGCAGCTT ATTTTACGGC GGCGCCTCTG CGAAGGGGCG
10201  GCCCGGCCAG GCGAGAGGTC GCCGCTTGGG CGGCTCGGCA CGGCCGTGCA
10251  GCATTCAAGG CTGCCACGAG GCCTCCGAGA CGCGCGTGGA AGTGTGACCA
10301  ATGCGGCCAG ACATTCTGCC TTCAGCACCG CGGACCTCTG CAGCACCACT
10351  GCCGGCCCGC CGCCGCCACG CGCAGCGCCG TCGCGCCCTC CCCTTCAGAG
10401  CGGGATGCTG GTCTCTGCCG GGTGACAAGG CGGTTTCCGT
10451  GGCATGTCTG CTCACTCATC CCGCCAACAC TCCCGAAAAG GCGGTGGGCA
10501  AGGCGACAGA GCTGCCCTCG GACATGGTGA CATGCCTCGT GTGCTTCCTC
10551  ATACCCACTT GTGTGTCCAA AAAGGACGGC AACGCTGGCT GCGAAGAGTT
```

FIG. 2R

```
10601  CGAGCCGGTG  CCCCGTTCT  TCATGTTCAT  GCCCAAGAAT  ACAGCACTAG
10651  GCCGTCTCCT  GGACACGGCG  GTGGATCGTG  CCGCCATGAA  CTCACCGGCC
10701  GTGCGCACCG  GAAAACCCTG  GAACTTGTTC  GCCGTCACAC  TGCCCATCCA
10751  CGCCGAGGCC  GAGGCAGCCT  ACTATTCTCC  TCTTACACTC  TCGACGGTGG
10801  TGAAAAAGAG  TGCTGTCGGC  ATGGCGGAGC  GCACTATTGT  GTTTCTCTCG
10851  CCGCTCCAAG  CCTTGCCCGA  AGGCGTGATC  AAGGGGGTGA  AGGACTTGGA
10901  TAGGAAAGGG  TCGTGGCCGT  CAACGTCATC  GTCCTCCAGT  CAAGGGTGTC
10951  AAGTGATGTG  ATGAGG
```

FIG. 2S

```
  1  MAYFTAKRAS SMGASTVPSG NDHLLEALTL CDCILSRYKR CGVQLNDAEA
 51  AAFANLQQRI SSISGHAADA ACPAGATRKQ SQELGLHEYA QLAQRCLIFQ
101  NPLAQIVATI NEEFSKLVSC SVRTHYANTN DAVLCDPVHD TVATIDTSTP
151  IGRCAKTKTT VTISDTVYIP LCYNSHVVGC LEVESTAIDT STPFFGYLLQ
201  VAALTLQNAT SIDTLRWETR KAEAMVGMAT RLARDTLEES VLVQSIINTA
251  KTLTESDRCS IFLVKADGSL EAHFEDGNVV VLPAGTGIAG HVAESGAVVN
301  IPNAYEDDRF HRSVDKVTGY HTRTILCLPI AFEGTIVAVA QLINKLDMVT
351  QSGQRLPRVF GRRDEELFET FSMFAAASLR NCRINETLLK EKKKSDAILD
```

FIG. 3A

```
401  VVALLSNTDI  RDVDSIVRHV  LHGAKKLLNA  DRSSMFLLDK  ERNELYSKMA
451  DSANEIRFPC  GQGIAGTVAE  SGVGENIMDA  YADSRFNSAV  DRQLGYRTQS
501  ILCEPITLNG  EVLAVVQLVN  KLGDDGSVTC  FTPTDQETFK  VFSLFAGISI
551  NNSHLLEFAV  NAGREAMTLN  LQRNSITAQR  APKSVKVIAV  TPEEREAVMS
601  IDFGGAYDFT  SPGFNLFEVR  EKYSEPMDAA  AGVVYNLLWN  SGLPEKFGCR
651  EQTLLNFILQ  CRRYRRVPY   HNFYHVVDVC  QTLHTYLYTG  KASELLTELE
701  CYVLLVTALV  HDLDHMGVNN  SFYLKTDSPL  GILSSASGNN  SVLEVHHCSL
751  AIEILSDPAA  DVFEGLSGQD  VAYAYRALID  CVLATDMARH  GDLSRVFDDM
801  AKAGYDSNDQ  ESRRLVMETL  IKAGDVSNVT  KPFETSRMWA  MAVTEEFYRQ
851  GDMEKEKGVE  VLPMFDRSKN  NELARGQIGF  IDFVAGKFFR  DIVGNLFHGM
901  QWCVDTVNSN  RAKWQEILDG  RRDSIRPSIV  *
```

FIG. 3B

```
  1  CTGCGAGCGG GAGGACAGGG CGAGGCAACG TGTGCGAGAT AAGGTCGTGG
 51  CACAGAGAGG ATACGGCTAT GAGAGGGATG TGTGCTGTTG GTGTGTCCTC
101  AACGTTCGTG CTAAAGGTCC GTCCAAAGGT GAGGAAGTTG GGACGAGGAA
151  GCATGCATGG ACGGTCTCGT GGCCTCATCA CCTCCTTTCG GTGCCATCAT
201  TACCACCCCT CGCTCCTGCT TTTTCGCCGC CATGCCCAGC GGGACTTTTT
251  TTCGTCTTGT TCGCTTTCCT CCTCCTCCTC CTCCTCCTCC TGTGGTTGCT
301  TTCATGCATG TAATCTATGC GCGGTGTGCG GACTACACCG TCGCCCACCG
351  CCCTCCCCTC TCCCGTCTT CTTTTTCCCG TTCCTCCTTG TTTAGCGTTC TCTTTTCTT
401  GGCACCCCCT CTTTTTCCCG AGCAACGCAA TGCCTCCGCC TCCCCACCCC
451  GTATGTCGCA CCCCTGTGTC CCTTGCGCAC GCCTCTTACC GTACTGTAAC
501  CCTTTTCGCG TACACGGGCA CCATCTCGGT TTTACTTGTA TATTAGTCTG
```

*FIG. 4A*

```
551   GCCTGCCAAA ATCATGAAGT CCACCACACC TGCCTAGTCC ATGCCGCCTA
601   TCTGTTGCCG CGATTCTGCA CCGCTCCTTA TCCAGCGCGT CGTTGGAGTA
651   GAATCTCCCG CTGGCCCGTC CCGTTGCCCT TGTATGGAGA CCGCCAAGAG
701   TTGTGGCACA TTCAAAGTTG CCCCATGTGC GACCCGGGCGA TTAGGCAACT
751   GTAAAAAAAG GAGCGGCGTC ATTCACAGGA GTAGACGGTG CGTTCTGCCG
801   TGGCCTCTTT CGTGCTGCTC TCTCTCTATG CATCTCTCTC CTTCTCACGG
851   ATTACTCTCC GTGGCCACTG CGTGCCCTCC TGGCTGTTTC CCGGCTCTTT
901   TCCCCATTTG TGCGCTCTTC CATCCATGCA CCCAATCAAA AAATCGGATG
951   CGGTCATGTC TGTCGTGCGT GCATCTCTGC ATCCGTCTGC CAGTGCGTGC
1001  GTGCGTGTGT GTGTGTGTGT GTGCGCACGT CAGAACCGTC TCAAGTCCCT
1051  CACCTCAGCG TCAATCTACC CTCATTGTCG TCGTCGGCCT TGACGTGTTT
1101  TCGGTCATCG TTTCACCATT GCTCCGGCTC AACGACCACA ATAGAAAAAA
```

FIG. 4B

```
1151  GCATAGGGAT CGGAAAGCTG TGGCCTATAC ACGTTCACGG GTGCCCGCTC
1201  AGCGCTGGAC ACGTGCGCAC GTCCACCGCA TCACAGTGAG AGACGGAGAG
1251  AAACCAGCGT AGCGCCATGG CATATTTCAC GGCCAAGAGG GCGTCCTCGA
1301  TGGGTGCAAG CACCGTTCCG AGCGGCAACG ACCATCTCCT CGAGGCACTC
1351  ACGCTGTGCG ACTGCATTCT GAGCCGTTAC AAGCGCTGCG GGGTTCAGCT
1401  CAACGACGCG GAGGCCGCCG CCTTCGCCAA TTTGCAGCAG CGCATATCTA
1451  GCATCTCCGG CCACGCAGCA GACGCCGCAT GCCCAGCAGG CGCCACTCGA
1501  AAGCAGTCGC AGGAACTGGG ACTGCACGAG TACGCTCAAC TGGCGCAGCG
1551  GTGCCTGATC TTCCAGAACC CCCTCGCCCA AATTGTCGCC ACCATCAATG
1601  AAGAGTTCTC CAAACTTGTG AGCTGTTCAG TGCGCACGCA CTACGCCAAC
1651  ACAAACGACG CGGTGCTATG CGACCCAGTG CACGACACTG TTGCAACCAT
1701  CGATACATCG ACCCCCATCG GCAGGTGTGC GAAGACGAAG ACGACCGTTA
```

*FIG. 4C*

1751 CCATTTCCGA CACGGTGTAC ATCCCCCTAT GTTACAACAG CCACGTCGTC
1801 GGCTGCCTGG AGGTGGAGAG CACCGCAATC GACACGAGCA CGCCGTTTTT
1851 CGGGTACCTG CTTCAAGTGG CGGCACTAAC ACTGCAGAAC GCTACCTCCA
1901 TCGATACACT GCGGTGGGAG ACTCGGAAGG CAGAGGCCAT GGTGGGCATG
1951 GCGACACGGC TTGCTCGAGA CACGTTGGAG GAGTCGGTGC TGGTGCAGTC
2001 CATCATCAAC ACGGCAAAGA CGCTGACGGA GAGCGACCGG TGTAGCATCT
2051 TCCTGGTGAA AGCGGACGGC AGCCTGGAGG CGCACTTCGA GGACGGCAAC
2101 GTTGTGGTGC TGCCTGCGGG GACGGGCATC GCAGGTCACG TTGCGGAATC
2151 TGGCGCCGTG GTGAACATCC CGAACGCGTA CGAGGACGAC CGGTTCCACC
2201 GGTCCGTGGA CAAGGTGACT GGCTACCACA CGGCACGAT CTTGTGTCTG
2251 CCGATCGCGT TCGAGGGCAC GATCGTTGCC GTTGCGCAGC TGATCAACAA
2301 GCTGGACATG GTGACACAGA GCGGGCAGCG GCTTCCGCGC GTGTTTGGAC

FIG. 4D

```
2351  GGCGCGACGA GGAGCTGTTC GAGACGTTCT CGATGTTCGC TGCGGCGTCG
2401  CTGCGCAACT GCCGCATCAA CGAGACGCTG CTGAAGGAGA AGAAGAAGAG
2451  CGACGCGATC CTGGACGTTG TGGCGCTGCT GTCGAATACG GACATCCGCG
2501  ATGTGGACAG CATTGTGCGG CACGTGCTGC ACGGGCGCGAA GAAGCTGCTG
2551  AACGCGGACA GGTCATCGAT GTTTCTGCTG GATAAGGAGC GCAATGAGCT
2601  GTACAGTAAG ATGGCGGACA GCGCGAACGA GATCCGGTTT CCCTGCGGGC
2651  AAGGCATTGC CGGCACTGTT GCCGAGTCCG GCGTTGGCGA GAATATCATG
2701  GACGCGTACG CTGACTCGCG CTTCAACAGC GCTGTGGACC GGCAGCTGGG
2751  CTACCGCACA CAGTCCATCC TGTGCGAGCC GATTACGCTG AATGGCGAGG
2801  TGCTTGCCGT GGTGCAGCTC GTCAACAAGC TCGGCGACGA CGGTAGCGTG
2851  ACCTGCTTTA CACCCACTGA TCAAGAGACG TTTAAAGTGT TCTCGCTGTT
2901  TGCGGGCATC TCGATCAACA ACAGCCATCT GCTGGAGTTC GCGGTGAACG
```

FIG. 4E

```
2951  CAGGTCGTGA  GGCGATGACC  TTGAACCTGC  AGCGTAACAG  CATTACAGCG
3001  CAGGGTGCTC  CGAAGAGTGT  GAAGGTGATC  GCGGTGACGC  CGGAGGAGCG
3051  TGAGGCAGTG  ATGTCGATCG  ACTTCGGGGG  CGCATATGAC  TTCACTTCAC
3101  CGGGCTTCAA  CCTGTTTGAA  GTGCGCGAGA  AGTACAGCGA  GCCGATGGAT
3151  GCGGCTGCCG  GTGTTGTGTA  TAACCTGCTA  TGGAACAGTG  GTCTACCCGA
3201  GAAGTTTGGC  TGCCGTGAGC  AGACACTGCT  GAACTTCATC  TTGCAGTGCC
3251  GCCGCAGGTA  CCGCCGAGTG  CCGTACCACA  ACTTCTACCA  CGTCGTGGAC
3301  GTGTGCCAGA  CGCTGCACAC  GTACTTGTAC  ACAGGCAAGG  CGTCGGAGCT
3351  CCTGACAGAG  CTGGAGTGCT  ACGTGCTGCT  CGTGACGGCA  CTGGTGCACG
3401  ATCTTGACCA  CATGGGCGTG  AACAACAGCT  TCTACCTGAA  GACGGACTCG
3451  CCGCTAGGCA  TCCTCTCCAG  CGGCGAGCGGG  AACAACTCCG  TGCTGGAGGT
3501  GCACCACTGC  AGCCTCGCCA  TCGAGATTCT  GTCCGACCCC  GCCGCGGACG
```

*FIG. 4F*

```
3551  TGTTCGAGGG GCTGAGCGGG CAGGACGTTG CGTATGCGTA CCGGCGCTG
3601  ATCGATTGCG TGCTGGCCAC TGATATGGCT CGCCACGGGG ACTTGTCGAG
3651  GGTTTTCGAT GATATGGCGA AGGCCGGCTA CGACTCTAAC GATCAGGAAT
3701  CTCGTCGCCT GGTGATGGAA ACGCTGATCA AGGCCGGTGA CGTGTCGAAT
3751  GTGACGAAAC CGTTCGAGAC GTCGCGCATG TGGGCGATGG CTGTGACGGA
3801  GGAGTTCTAC CGTCAGGGTG ACATGGAGAA GGAGAAGGGC GTGGAGGTGC
3851  TGCCGATGTT TGACCGGTCG AAGAACAACG AGCTGGCGCG TGGGCAGATT
3901  GGGTTCATCG ACTTCGTAGC TGGCAAGTTC TTCCGGGATA TTGTGGGCAA
3951  CCTATTTCAT GGAATGCAGT GGTGTGTGGA CACGGTAAAC TCCAACCGCG
4001  CAAAGTGGCA AGAGATCCTG GATGGCCGCC GCGACTCCAT CCGACCCTCG
4051  ATTGTTTAAG GCGTCGGTCC CGTGGTATCG TTGATGCCGT AATAGCGCGC
4101  GGTGGTGCCG TTGCTCCTGG TGCGGAAAGT GTCTGGTAAG TGCAGGCGCT
```

*FIG. 4G*

```
4151  GTGTTGACGT TGGCGGCTGT GCTTATCTAG GCGAACGCTT GTGTCATGGA
4201  TGAGCAGCAG GTTTCGAGCA GCGGTGCAAT GCGGGGCGCTG GAAGGGGGAA
4251  TGTTGCAGTG TTGTTGGGGT GTGTGGCTAC AATGCTAAGC GTCTGTGCGT
4301  TGGAGCTTGT TCTCATGTGT TGCTTCTATG CTACCCATTG GATGTTCAAT
4351  CGCAAAGGTT AAGAGACTGC TGTCTGTTTT TTTTTTGTCT GTACAACTCT
4401  TCTGCTTCTT CTCTCTGTGT TGCTGCTGCT GTCGCCTCGC TGCACCGCCA
4451  CTCGGCCCCC TTCTTCCGTG GCCCCATGCT CGTGCGTACG TGTGCGTGAA
4501  GAGGCACTGG CGGTGTCGGC GTCCGGCCCA CCCCACCCCC CGGCAGGCCA
4551  CACGCATTCG GAGACTACCC CCTCTCGCCT CTCTCGTTTT CGTTTCGTTT
4601  TTGGTTGGTT CTCTTGTCGC TTTGGTTGGT CCTCTGCACT GTGCGCTTGC
4651  TCGTATTTAT CCCTTGCCTC TGTTTCCTGT CGGTGTAATC GGATGCACCA
4701  GCCACGTGTG TATGCCGGTG TCTGTAAGTG AAGAAGTCAG AGATTGGTAC
```

*FIG. 4H*

```
4751  GCTTGTGCAC  AGACTCAGAT  ACCCATATAT  ATGCCAATAA  AATCGATTAT
4801  TGTATCTCGG  CCATTCACCA  AGCCCTCCCT  CCCCCTCGCC  CACTCCCATT
4851  CCGAGTGTGC  TGTACTTTGT  TTCTTCCTCC  TTCTTCAATT  TCTCTTCCCC
4901  CCCCTCTTCT  CTTGATTTCG  TCCCCCTCCC  GCTTCTCGCA  CGAAACGACA
4951  GGAGGGCGGT  GCGATGTGGC  TGAGGCCGAT  GCTGGAACAC  TGGGAAAACG
5001  CCGCAGAAAC  GTCTTGGATT  TAGATCTGTC  TCACCCTCCC  CTATACCTAT
5051  CTCTCCCGCC  ACCAGTGTAG  GCGATGGAGT  GTCTATTGTG  TGGTGGACGG
5101  TGCTCCTGTT  GGGTAAATGG  CCTGTAGGAT  GTTCGAAGTA  CGTGTTCTTC
5151  TCAGCACAAC  GCTGGATGTC  CTGCGCTTGC  CACCGCGTCT  GTCTCCCACA
5201  TTCTCTGTAT  GTTTCACCTT  CTCTCTCCCG  TTGGCACAAG  GCAGGCATCG
5251  AGCGTGTGCG  TTCTTTTCTC  TTGGCGATGG  CGCACGCTCT  GTGCTTCTTT
5301  TCGTCTCTGC  TCGCTGTTAC  CCTCCCGCTG  TCAGTGCGCC  TCTCTTGTTC
```

FIG. 41

```
5351  TACGACTTCG CGGCTCTGTT CCACTCCCCC CCCCCTATCT CCACTCCCCC
5401  CACACACACA CCACTCCCAT CTGTTCGCGT ACTATATGCT CAATGCTGAG
5451  CCTGGGTTCC AAGTGGTTCT CTTGCTCTTC GTCGTCCCCG TCTCGCGCTC
5501  TTGTCTCTCT TTTCCCGTTA CGGTTTCCTG TCTGTCGCCA CTTTCTCGGC
5551  ATCCCCGACC CGATGTACAA CTCAAGCCCC ATGTGACGTC TCACCTCCGT
5601  CTTCCCTCCTC CCCGAACCCC CCCCTAGGGC GCTTCTCTTC TCTCTCCCGA
5651  TTTTTGTCTT CCTTTTTCTC TTTTACGATT GGATTGCACT TCTTCGTGCT
5701  TCCGCGTATG ATAGGACGCC TTTTACGATT GGCGTGGCCC CCCCCCCTTC CACCTCCCGC
5751  ACCTTCTCTC CGTCCCTCTT CCCACGTGTA GCTGTCCGTG CTTTTGTGCG
5801  AAGTCGATGC AATCCAAAACC AAGCTGTGTG CGCGGAAGGA GAGCGACAGA
5851  GAGAGAGAGA GCGAGCGAGC GGAACTGGAG AAGGTGCCGC TCACCAACAG
5901  AAGAGGAAAG AGGCGGGTAC GTTACACCAC GAGCCAAAGC GAAAGAAAAG
```

FIG. 4J

```
5951  TAGGACGGTA CCGCACACAC TGCGGTACGC CCGGAGACTC GTTCCCTCGC
6001  CATGACCGCC GCCAAAGAAG CCGTGTTAGA GTGAACCAGA TTGTTTCTGA
6051  GTTGCTCCCC GGTGTGCTTG GCTGCGGCAG CACCTCTCCC CCTTCACGTC
6101  TGCGGCGGGC CACGCGCGGT GAGAGGGCGT AGACACACCA CGCATGGGAG
6151  AAGACAAAAC ATGAGATGAC GAACACCTCG TGCGGTGCTG AAAGCAGTGC
6201  TAAGTAGCGT CTTTAAGGCA CCCCACAGGA CGACTGCTCT GTCGGGACT
6251  TCTATCCAGA TGTGTTCATC CTCGTGTACC TCTCCCTTGA TTCGCCTGTG
6301  TTCCACGCAC GTGCTCCACC TCATCATACT TTACTGATCC TCCCCTCCT
6351  CTTCCCCTGC TCTGCGACAC CTTCTCTTCG ACACTTGCCA CGACCTGTCG
6401  GTGCGCCCTT CTCCCTCCTC TCGCCACGTC CTGCCCCACT TCGACACCCT
6451  GGGAAACTTG CACGTGCTCG TGCACGCGGC CGTTTGGCAC CTCACCCATC
```

*FIG. 4K*

```
6501  TCCCACACGC CGACATACAT ATGCCCCGCT CCTCGCTTCA GCAATAACAG
6551  GTTAGGCATA CACACGTACA CAAGTGCACT TCCATCACTA CAACTCTTTT
6601  GACAGGACTA CCACCCTTTT ACAACCCTCC CCAACACGA GAAATGACTG
6651  GAGAAATCAG CGAGAAGGCC TTCCCTCTTT CGACGGACCG CCTCAGCCAG
6701  ACCATCCTCG ATCTCGTGCA GGAGGCGAGC AATGCCAAGA TGGTGAAGAA
6751  AGGTGCCAAC GAGGCCACCA AGGCCTTGAA CCGGCGGTATT GCGGACCTGA
6801  TAGTGTTGGC GGGTGACACG AACCCGATTG AGATTCTCCT GCACCTCCCC
6851  CTCTTGTGCG AAGACAAGAA CGTCCCGTAC GTCTTCGTGC CGTCCAAGAC
6901  GGCGCTTGGC CGCGCGTCGC AGTGTCTCG CAATGTCGTG GCGCTAGCCA
6951  TCCTTCAGGG CGAGAACAGC CCTGTTGCGG CGAAGGTGCA GGCAGTGAAG
7001  CTCGAGATCG AGCGCTTGCT CTGAGGTGTT TTTCCTTGCT TTCTGTTTGT
7051  AATTTTTTT TGTATTTGCG TGTTCCCTGT GTTTCTGTTC TCTTT
```

FIG. 4L

```
  1  MHSAVFSPDA  PYCGAAGSNH  LCEAVALCQS  ILARYRRTGT  SFSSTELKAI
 51  QALRTEFPDT  AQEPAANSAA  SPDQTTKDFL  SILDDATDVP  HNPQNDIVAF
101  VEECCDNTKE  PTVLFAAINE  RISAVTCSRN  VRTYMVIAND  NLLWDPVNGV
151  AALIDDVTPL  GKCAQARNML  TIANTLYIPL  WFRSELVGCV  EVPGACIPRD
201  KATCAQLLLR  CVTVAVRNSI  NISIRKREAN  KIEAMVGMAT  RLARDTLEES
251  VLVQSIINTA  KTLTESDRCS  IFLVKADGSL  EAHFEDGNVV  VLPAGTGIAG
301  HVAESGAVVN  IPNAYEDDRF  HRSVDKVTGY  HTRTILCLPI  AFEGTIVAVA
351  QLINKLDMVT  QSGQRLPRVF  GRRDEELFET  FSMFAAASLR  NCRINETLLK
401  EKKKSDAILD  VVALLSNTDI  RDVDSIVRHV  LHGAKKLLNA  DRSSMFLLDK
451  ERNELYSKMA  DSANEIRFPC  GQGIAGTVAE  SGVGENIMDA  YADSRFNSAV
501  DRQLGYRTQS  ILCEPITLNG  EVLAVVQLVN  KLGDDGSVTC  FTPMDRETFQ
```

FIG. 5A

```
551  VFSLFAGISI NNSHLLEFAV NAGREAMTLS LQRNSITAQR APKSVKVIAV
601  TPEEREAVMS IDFGGAYDFT SPGFNLFEVR EKYSEPMDAA AGVVYNLLWN
651  SGLPEKFGCR EQTLLNFILQ CRRYRRVPY HNFYHVVDVC QTLHTYLYTG
701  KASELLTELE CYVLLLVTALV HDLDHMGVNN SFYLKTDSPL GILSSASGNN
751  SVLEVHHCSL AIEILSDPAA DVFEGLSGQD VAYAYRALID CVLATDMAKH
801  ADALSRFTEL ATSGFEKDND THRRLVMETL IKAGDVSNVT KPFETSRMWA
851  MAVTEEFYRQ GDMEKEKGVE VLPMFDRSKN NELARGQIGF IDFVAGKFFR
901  DIVGNLFHGM QWCVDTVNSN RAKWQEILDG RRDSIRSSIV *
```

FIG. 5B

```
  1  ACAGGCAGGT GCGTGTGGAG AGGTTGAAGG ACAAGTTCA  TCCACAGCTC
 51  AGTGCCGCCA AGCCGGTGCT CAAGTTGAAT GCGGCTCCCG CGCCGTTGTG
101  CAAGAAGAAT CCACTGTCAG CCCCAGTGCC TTTGAAGAAG GTGCCAGCAA
151  TGGTAAAGCC GCAACGGAAG CGGACGCTGC CGATCGTCAC CAAGACAACT
201  GCGAGAAAGG CCGCACCGGT GGCGTCTCCT GATAGAAATG CCCCGCCGGC
251  AGTGACGCTT CAGCTGGGTCA CCAAGCGAGC TGCCGGGCGTT TCCCGCACTG
301  AAACGAAGGG TGTGCCCGCC TCCTGCCGAG CCCGCCGTGAA GGTCAGCGCG
351  GCCCAAAAGG TAGCCGGCGGC CGCTACCAAG AAGGCGCTCA AGAAGGGTAC
401  ATCCACCTCA CAGGCGACAA CCGCCACAGA CGAGGGTGGG GACTTCTTCG
451  CCGAGGATTT CATGGCGGAA GGTGAAGGAG ACGACGTCGG GCTCGAGGTT
501  GCCGACAAGT CCGCTGGGTGA CACGAACGCG CAAGTAGCAG CGCCCACGGC
```

FIG. 6A

```
 551  GCCAGTGAAG CAGAAGCGTA AGTCCGCCGG GCGTCGTGCA GCTCGCAGTC
 601  ACCTCCTTGC ACCCGAGTCG ATGCTCCCTG CGACGGCACG GTCACAGAAG
 651  GTGATTGTGG CGCACACCCC CACGTGTAGA AAGGCACCGC GGCCGGTGTG
 701  CACCTCCCCA TCATCCCCCT TTACTCCTGC ACGACGCAAG GTGAGCCTTG
 751  CCGACAACAT CCGCGCTCAG CTGGCCAGTT TTTGTAGTC ACTGGGTCGC
 801  GTGCGTGGTG CCGAACGCGG GGAACGGCTT GACCTACCTC TTCACGCGCG
 851  CTGAACAACA TATAGAGAAA ACACTAGATG CCACCCTTTC CTCTCCTCTC
 901  CCAGCTGCCC TTCCCCTGCT CCCCATCGAC CATGCGTGAA GGTTGTCCCC
 951  ACCACCTCGT ATCTGTCCAG CGGTGGCATG ATAATGGCGG CAGATTGAG
1001  CTGACTTGGA GAATGGCAAG ACAGGAAAGC GGGGGGGGGG GGGCAAAAGA
1051  AGAGATAGAG GGGAGAGCGT ATGAGGGGGG GGGGCGGCGG ACGCGCACAC
1101  ACTCATCTGC TCGTGAGGGC ACGTAACGCC CTAGCAAAATG TTTTGCATAG
```

FIG. 6B

```
1151  ACAAGGGAAG GACAAAGCGC CATCGATACC GGAGAGCAAT ACAGACTCAC
1201  ATACATACAT ACATGCGAAC GCCTACGCGC GTCCCGCACA TGAGGACAGC
1251  CGAATAAGTC TGCGGTGTTA CCTCAAAGAA AAAGGCACAG GAGGCACAAT
1301  CGAGACAGCA GCTGTGCTGT CTCGGTTGCG GTACGAGGTG TTCCGCCCAC
1351  GTCGTTTTCT GCACATCCCT TCACGATTGT GCTGCGGGTG CGCTCGTGTG
1401  ACTCATTGTC GAAACACGTC AGAGCAGCTG CCGGCCACAA CAGTACCCCG
1451  CTGGCGCGGC TGGCGAGACG CGGGGACATC ACGTGTCAGT ATGGTGCCAC
1501  CAAGCGAAGA GGGAGGGAGA GGCGAAGGGC TGAGATGACG GATCTGCTAC
1551  TGAATGCGCG AAGAGCGGGC GTGTGGTACG TGGAGGATAG CCGCCCAAGT
1601  TGAACGTTAC GGCTCGATCT TCTCCGTGAA GAAACGGTGC GCGTTCTCCT
1651  TTTCCGCTGC CGTTTCTTTC TCTCCCTGTA TGCCTCGCCA TCATGTATCA
1701  TTACGGATGT CCTGTCCTGC CCCACTTCTT CCTGCCTTTC TCGCCTACCA
```

FIG. 6C

```
1751  ACTACTGAAC GCTGTCAGTG CGCCTCTCGC TTCTCCAGCT CCACACGCGC
  18  TCACTGGCCA TCATCAAAGG GAAGCCACCA TCGGCACCCA AGGAGCTTAA
  18  CCAGCATTTG AGGTTCTTCA AAAGGCGGTG TGAGGTGCAG CTGCACTGGA
  19  TCATTCGGGG GACACAAACG CGCATGCGTG CACGGCTGCA CACGGACCC
  19  GTCATTGTCT CTTCCGCTCT GTTGCTCCTG TCGCCGCTCT CCACAGCGAC
  20  ACACATACAC ACACACAAGC ACACACACAC ACACACACAC ACACACACAC
  20  ACACACAAGC GAGCCCCATA CACGCAAACG CCACGCGGCC TCTTTGTTGT
  21  TCGTTTGTTC ACTCTTGTTT TTCGGCTCGT ATTGGCCGCT GTCTTCGATT
  21  TGTTATCAAC TGGCAGTGAC GCCGTACAGC GATGCATTCA GCGGTCTTTT
  22  CCCCCGATGC GCCGTATTGC GGCGCAGCCG GCTCCAATCA CCTATGTGAG
  22  GCGGTTGCAC TCTGCCAGTC GATTCTGGCG CGCTACCGTC GGACTGGTAC
  23  ATCCTTCTCC TCCACAGAGC TGAAGGCGAT TCAAGCCCTG CGCACCGAGT
```

*FIG. 6D*

```
2351  TCCCTGATAC  CGCGCAAGAG  CCGGCTGCGA  ATAGCGCGGC  TTCACCCGAC
2401  CAGACCACGA  AGGACTTCCT  GAGCATTCTT  GACGATGCAA  CCGACGTGCC
2451  GCACAACCCA  CAGAACGACA  TTGTCGCGTT  TGTGGAGGAG  TGCTGCGACA
2501  ACACCAAGGA  GCCAACAGTA  TTGTTTGCGG  CGATTAATGA  GCGCATTTCA
2551  GCCGTGACTT  GCTCGCGTAA  TGTCCGCACG  TACATGGTGA  TCGCAAACGA
2601  CAATCTCCTA  TGGGACCCTG  TCAACGGTGT  TGCCGCCCTT  ATCGACGACG
2651  TCACGCCCTT  GGGCAAGTGC  GCGCAAGCGC  GCAACATGCT  GACGATTGCC
2701  AACACCCTAT  ACATCCCCCT  CTGGTTTCGG  TCCGAGCTCG  TTGGCTGCGT
2751  GGAGGTGCCG  GGTGCCTGCA  TCCCAAGGGA  CAAGGCTACC  TGTGCTCAGC
2801  TTCTGCTCCG  GTGCGTCACC  GTTGCCGTTC  GAAACAGCAT  CAACATCTCC
2851  ATCAGAAAGA  GGGAAGCAAA  TAAGATCGAG  GCCATGGTGG  GCATGGCGAC
2901  ACGGCTTGCT  CGAGACACGT  TGGAGGAGTC  GGTGCTGGTG  CAGTCCATCA
```

FIG. 6E

```
2951  TCAACACGGC  AAAGACGCTG  ACGGAGAGCG  ACCGGTGTAG  CATCTTCCTG
3001  GTGAAAGCGG  ACGGCAGCCT  GGAGGGCAC   TTCGAGGACG  GCAACGTTGT
3051  GGTGCTGCCT  GCGGGGACGG  GCATCGCAGG  TCACGTTGCG  GAATCTGGCG
3101  CCGTGGTGAA  CATCCCGAAC  GCGTACGAGG  ACGACCGGTT  CCACCGGTCC
3151  GTGGACAAGG  TGACTGGCTA  CCACACGCGC  ACGATCTTGT  GTCTGCCGAT
3201  CGCGTTCGAG  GGCACGATCG  TTGCCGTTGC  GCAGCTGATC  AACAAGCTGG
3251  ACATGGTGAC  ACAGAGCGGG  CAGCGGCTTC  CGCGCGTGTT  TGGACGGCGC
3301  GACGAGGAGC  TGTTCGAGAC  GTTCTCGATG  TTCGCTGCGG  CGTCGCTGCG
3351  CAACTGCCGC  ATCAACGAGA  CGCTGCTGAA  GGAGAAGAAG  AAGAGCGACG
3401  CGATCCTGGA  CGTTGTGGCG  CTGCTGTCGA  ATACGGACAT  CCGCGATGTG
3451  GACAGCATTG  TGCGGCACGT  GCTGCACGGC  GCGAAGAAGC  TGCTGAACGC
3501  GGACAGGTCA  TCGATGTTTC  TGCTGGATAA  GGAGCGCAAT  GAGCTGTACA
```

*FIG. 6F*

```
3551  GTAAGATGGC GGACAGCGCG AACGAGATCC GGTTTCCCTG CGGGCAAGGC
3601  ATTGCCGGCA CTGTTGCCGA GTCCGGCGTT GGCGAGAATA TCATGGACGC
3651  GTACGCTGAC TCGCGCTTCA ACAGCGCTGT GGACCGGCAG CTGGGCTACC
3701  GCACACAGTC CATCCTGTGC GAGCCGATTA CGCTGAATGG CGAGGTGCTT
3751  GCCGTGGTGC AGCTCGTCAA CAAGCTCGGC GACGACGGTA GCGTGACCTG
3801  CTTTACACCC ATGGACCGGG AAACGTTCCA AGTGTTCTCG CTGTTTGCGG
3851  GCATCTCGAT CAACAACAGC CATCTGCTGG AGTTCGCGGT GAACGCAGGT
3901  CGTGAGGCGA TGACCTTGAG CCTGCAGCGC AACAGCATTA CAGCGCAGCG
3951  TGCTCCGAAG AGTGTGAAGG TGATCGCGGT GACGCCGGAG GAGCGTGAGG
4001  CAGTGATGTC GATCGACTTC GGGGGCGCAT ATGACTTCAC TTCACCGGGC
4051  TTCAACCTGT TTGAAGTGCG CGAGAAGTAC AGCGAGCCGA TGGATGCGGC
4101  TGCCGGTGTT GTGTATAACC TGCTATGGAA CAGTGGTCTA CCCGAGAAGT
```

*FIG. 6G*

```
4151  TTGGCTGCCG TGAGCAGACA CTGCTGAACT TCATCTTGCA GTGCCGCCGC
4201  AGGTACCGCC GAGTGCCGTA CCACAACTTC TACCACGTCG TGGACGTGTG
4251  CCAGACGCTG CACACGTACT TGTACACAGG CAAGGGCGTCG GAGCTCCTGA
4301  CAGAGCTGGA GTGCTACGTG CTGCTCGTGA CAGCTTCTAC CGGCACTGGT GCACGATCTT
4351  GACCACATGG GCGTGAACAA CAGCTTCTAC CTGAAGACGG ACTCGCCGCT
4401  AGGCATCCTC TCCAGCGCGA GCGGGAACAA CTCCGTGCTG GAGGTGCACC
4451  ACTGCAGCCT CGCCATCGAG ATTCTGTCCG ACCCCGCCGC GGACGTGTTC
4501  GAGGGGCTGA GCGGGCAGGA CGTTGCGTAT GCGTACCGCG CGCTGATCGA
4551  TTGCGTGCTG GCCACTGATA TGGCGAAGCA CGCTGACGCG CTAAGTCGCT
4601  TCACAGAGTT GGCGACAAGC GGGTTTGAGA AAGACAAGCA CACCCACCGT
4651  CGCCTGGTGA TGGAAACGCT GATCAAGGCC GGTGACGTGT CGAATGTGAC
4701  GAAACCGTTC GAGACGTCGC GCATGTGGGC GATGGCTGTG ACGGAGGAGT
```

*FIG. 6H*

| | | | | | |
|---|---|---|---|---|---|
| 4751 | TCTACCGTCA | GGGTGACATG | GAGAAGGAGA | AGGGCGTGGA | GGTGCTGCCG |
| 4801 | ATGTTTGACC | GGTCGAAGAA | CAACGAGCTG | GCGCGTGGGC | AGATTGGCTT |
| 4851 | CATCGACTTC | GTAGCTGGCA | AGTTCTTCCG | GGATATTGTG | GGCAACCTAT |
| 4901 | TTCATGGAAT | GCAGTGGTGT | GTGGACACGG | TAAACTCCAA | CCGCGCAAAG |
| 4951 | TGGCAAGAGA | TCCTGGATGG | CCGCCGCGAC | TCCATCCGAT | CCTCGATTGT |
| 5001 | TTAAGGCATC | GGTCCCGCGG | TATCGTTGAT | GCCGTAATAG | CGCGCGGAAG |
| 5051 | TACTCACGGC | GAATGTCTTT | CGAGAAGTGA | AAGCGGGTGAG | CTCACTTGTC |
| 5101 | ACTATGGACG | GATGAGTGCC | GTTGGTCGCC | GCTCTGCTGT | GCGTGTCTAC |
| 5151 | GCGTCTTATC | CCCACCCTCAG | TATGTGCACC | GGGCCCGTCAT | TTCCCTTTGT |
| 5201 | ACCCGTCGCT | GTATCCGCGA | CGCGGGATGG | TTTGTGTGTT | GGTGAGTCTC |
| 5251 | CCTCTCTCTG | CACCAGGGCC | TGTTCTGGTT | GATGGGGCGCC | TCTCGACTG |
| 5301 | CTGAGGACAA | GGTGTGGCAC | ATGTGGGCGT | GTGAGTCGTG | TTTTTTTTTT |

FIG. 6I

```
5351  TTGGCTCTCG TCTTGTCTCC TCTCTCCTCG CTATTAGCCC TTTTCTGAAC
5401  AGACCTCTCT CTCTCTCTCT GCTCGTCTTT CGGAGGAGTG GTTTGCCGTT
5451  GAAGGCTGAA CGGTACGAAG GGGGAGGAGT GAGCAGTGCA GGTGCACACA
5501  CACGCACCAC ACCTAATTCT CTCTTCATCC GCCTTTCCTT TTTTTCCGGT
5551  GTGTGTCCCG AAGATGGTTT CCTGTCTTTG CATCCGTTTC TCTCCCCCTT
5601  TTTTCGTGTG TCTGTCTTTT GTTGTTCGTC ACGAATCTCA CCCGCCTCCC
5651  TCCCCCCTCT CCCATTTTTT CTCTCGTAGG TGTGCTCCTG TGTGCTCCTG
5701  GTGAGACGGA GTGGAGTGGG GGCACCCCGC AGCGCGTGGC ATCTCTCCCC
5751  CCCCCCAGGT GGGGGGTCAT TCGTGCACCC AAACTCTGTC TCTGGGGAGG
5801  AAGCTCAGCG GCGCACCCCC ACCCCCCACC CCACCCCTCTC CCTCCTATAT
5851  CCCTGCCAGT GCGGAACCGC TTCTCCTGGC GACAGGGTCA AGCACCTATA
5901  ACGCAGGGAG GACAGAGCAA GATGTCGCTG CGGATGTCGG CCGTCAGGTG
```

*FIG. 6J*

```
5951  CCGGATGGCG  TGGCGCCGGA  GCGACCTGCG  ACAGGCGCACA  CGCACGATTC
6001  ATGTGATGGG  CAGAGTGCCG  GCGTGACTCG  AACGCATCCC   ACCCCCGGCC
6051  CTCACACTGT  CCTGCTGCTG  TGGGGAGCCT  GTGCCATCGC   GATGGAATCG
6101  CACCGTGTGG  CGACCGGCAC  AACGTGAGCG  GCTGTGGGGC   GACCTGTGAG
6151  GCGGGGTGGG  TGGGTGGGTG  GCGGGTAGAG  TTCGAGGCTG   AGGCTGTGCC
6451  TCGAAGTTTT  TTGGGTCTGC  AGAGAGAGGC  GATGGGAGGA   GGAGCAGCCA
6501  GGCTTGCGTT  GTGTGATGTC  GPGAAGAACA  ATGTAACAGC   TCTTCTCTCG
6551  TTGTCCTCCT  TCCTCCCGCT  TCTGTTCGGC  GAGGAAAACA   GCAGACTTGT
6601  GTAGCACAAG  ATGCTGCTGG  CGCCTGCTGT  GTGACATGTG   CGAGGAAGCC
6651  TCGCGCAAAC  CGTTTGTGGT  CTCTGGAGGG  GGTACTGCCGA  GCGGGAGGAC
6701  AGGGCGAGGC  AACGTGTGCG  AGATAAGGTC  GTGGCACAGA   GAGGATACGG
```

*FIG. 6K*

| | | | | | |
|---|---|---|---|---|---|
| 6751 | CTATGAGAGG | GCTGTGTGCT | GTTGGTGTTT | CCTCAACGTT | CGTGCTAAAG |
| 6801 | GTCCGTCCAA | AGGTGAGGAA | GTTGGGACGA | GGAAGCATGC | ATGGACGGTC |
| 6851 | TCGTGGCCTC | ATCACCTCCT | TTCGGTGCCA | TCATTACCAC | CCCTCGCTCC |
| 6901 | TGCTTTTTCG | CCGCCATGCC | CAGCGGGACT | TTTTTCGTC | TGTTC |

FIG. 6L

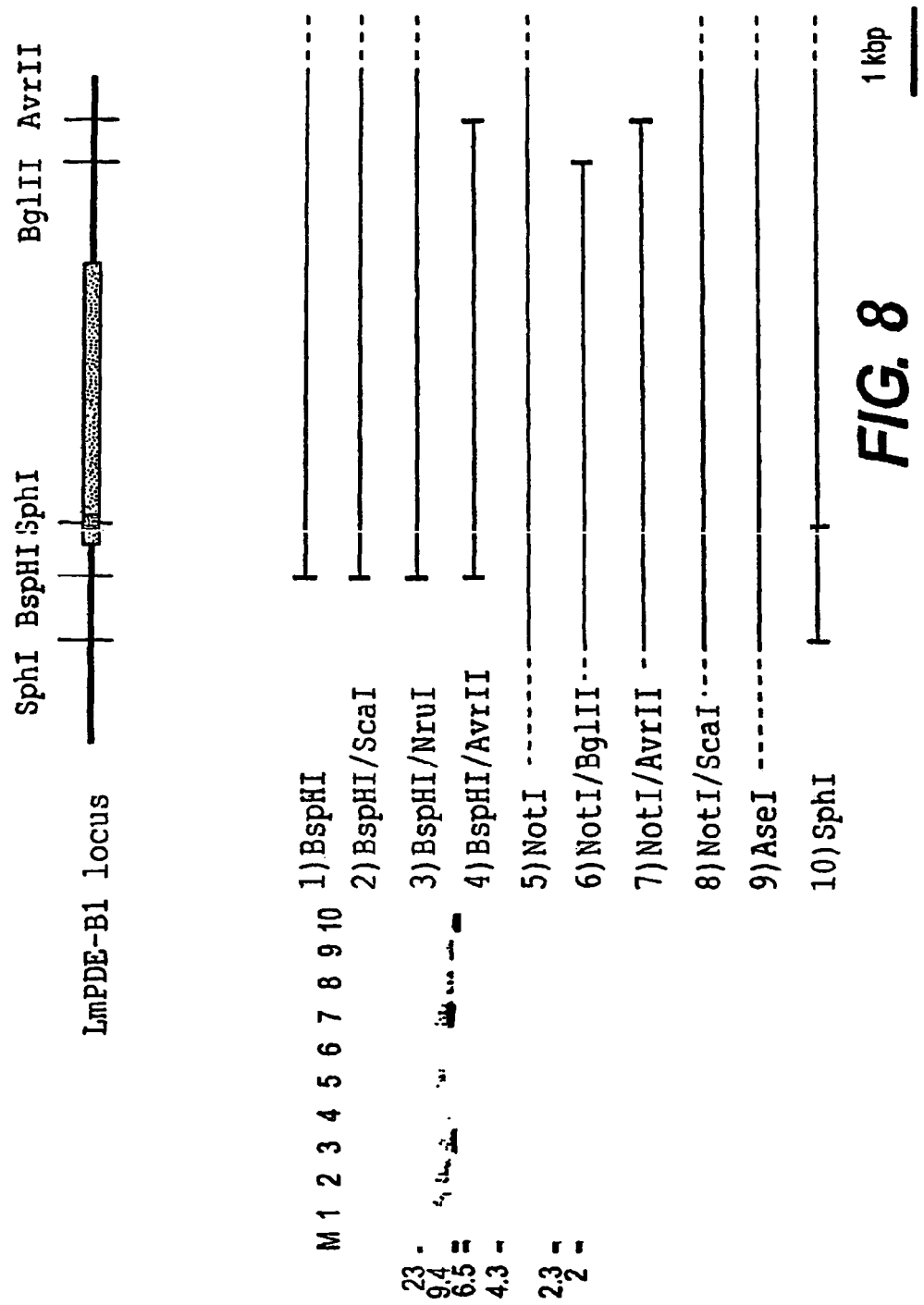

M 1 2 3 4 5 6 7 8 9 10

23 —
9.4 —
6.5 —

4.3 —

2.3 —
2 —

1) BspHI            6) NotI/BglII
2) BspHI/ScaI       7) NotI/AvrII
3) BspHI/NruI       8) NotI/ScaI
4) BspHI/AvrII      9) AseI
5) NotI             10) SphI

*FIG. 10*

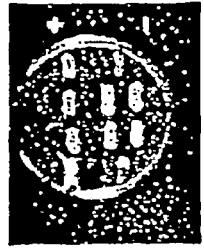
FIG. 12A WITH HEATSHOCK — LmPDE-A in pLT1
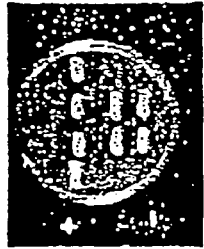
FIG. 12B WITHOUT HEATSHOCK — LmPDE-A in pLT1
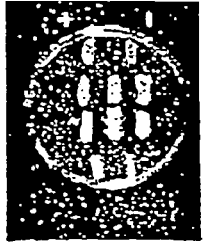
FIG. 12C WITH HEATSHOCK — LmPDE-B1 in pLT1
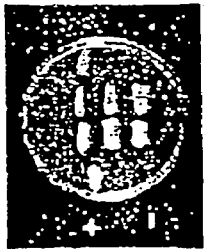
FIG. 12D WITHOUT HEATSHOCK — LmPDE-B1 in pLT1

CYCLIC NUCLEOTIDE-SPECIFIC PHOSPHODIESTERASES FROM *LEISHMANIA* AND USES THEREOF

The present application is a U.S. National Phase application of International Application PCT/IB04/03990 (filed Sep. 3, 2004) which claims the benefit of U.S. Provisional Application No. 60/500,244 (filed Sep. 5, 2003), 60/504,070 (filed Sep. 19, 2003), and 60/582,584 (filed Jun. 25, 2004), which are incorporated herein by reference.

FIELD OF THE INVENTION

The present invention relates to novel amino acid and nucleic acid sequences of cyclic nucleotide-specific phosphodiesterases from a parasite in the *Leishmania* family, such as *Leishmania major*. The invention also relates to nucleic acid constructs, vectors, and host cells comprising the nucleic acid sequences as well as methods for producing and using the amino acid and nucleic acid sequences. The invention further relates to the use of these sequences, and of antibodies directed against these sequences, in the diagnosis and treatment of disorders related to the infection of *Leishmania*, such as *Leishmania major*, including the identification of compounds that form complexes with the polypeptides and nucleic acids of the present invention.

BACKGROUND OF THE INVENTION

*Leishmania major* is one of several *Leishmania* parasites that, when introduced into a host organism, is the causative agent of leishmaniasis. *Leishmania major* is a species of the *Leishmania tropica* complex. Other complexes (comprising species and subspecies) include *Leishmania donovani*, *Leishmania mexicana*, and *Leishmania viannia*. According to the World Health Organization, leishmaniasis is among the most infectious diseases worldwide and is endemic in 88 countries in Africa, Asia, Europe, and in North and South America. It has been estimated that over 12 million people suffer from Leishmanial infections worldwide, where serious public health problems exist particularly in countries such as Iran, Iraq, Afghanistan, Algeria, Brazil, India, Peru, and Syria. Leishmaniasis most commonly manifests itself as either cutaneous (i.e. skin) leishmaniasis (CL) or visceral (i.e. internal organs) leishmaniasis (VL). CL is the most common form of leishmaniasis and is the result of transmission of the parasite *Leishmania major* via the bite of an infected female phlebotomine sandfly. Symptoms of CL include large skin legions or ulcers on exposed parts of the body, which cause serious disability and permanent scarring.

Methods of treating leishmaniasis have typically been limited to administering pentavalent antimony ($Sb^V$) (Sundar et al. (2002) *Curr. Opin. Infec. Dis.* 15, 593-598). Due to the recent emergence of large-scale resistance to $Sb^V$, however, the effectiveness of this treatment is becoming increasingly limited. Furthermore, $Sb^V$ treatment has several side effects including nausea, vomiting, diarrhea, and convulsions. In addition, HIV co-infection with *Leishmania* species presents further challenges since such co-infection can dramatically alter the epidemiology, diagnosis, and response of leishmaniasis to therapy (Lee et al. (2003) *Int. J. Infect. Dis.* 7, 86-93).

SUMMARY OF THE INVENTION

The invention provides novel *Leishmania* cyclic nucleotide-specific phosphodiesterase (LmPDE) polypeptides and nucleic acid molecules thereof that are useful in the diagnosis and treatment of leishmaniasis. The polypeptides of the present invention also include antibodies that recognize and bind to LmPDE polypeptides. The nucleic acid molecules of the invention also include peptide nucleic acids (PNA), and antisense molecules that react with the nucleic acid molecules of the invention.

In one embodiment, the invention provides full-length, novel phosphodiesterases (PDEs) from the parasite *Leishmania major*, designated LmPDE-A, LmPDE-B1, and LmPDE-B2, including the polypeptide molecules, corresponding nucleic acid molecules, and fragments thereof.

The present invention also encompasses various nucleotide and amino acid sequences that represent different forms and fragments of the LmPDE genes, transcripts, and proteins, such as conservatively mutated proteins, different allelic forms, polymorphic forms, alternative precursor transcripts and mature transcripts. Additionally, recombinant nucleic acid molecules that are codon usage variants of the novel LmPDE sequences are provided. The invention encompasses LmPDE from *Leishmania major*, as well as other *Leishmania* species and subspecies of the complexes *Leishmania tropica*, *Leishmania donovani*, *Leishmania mexicana*, and *Leishmania viannia*.

The present invention further provides recombinant nucleic acid molecules that encode wild type or mutant sequences of LmPDE polypeptides that maintain PDE biological activity. These include naturally-occurring and synthetic mutants, as well as semi-synthetic and recombinant polypeptides.

The present invention also includes the polynucleotides encoding LmPDEs in recombinant expression vectors and host-vector systems that include the expression vectors. One embodiment provides various host cells transformed with recombinant vectors that include the LmPDE nucleotide sequences of the invention. The invention also provides genetically modified organisms comprising a vector containing a recombinant LmPDE sequence wherein at least one endogenous LmPDE gene has been disabled.

The present invention further provides methods for using substantially purified LmPDE polypeptides to identify compounds that modulate the expression or activity of LmPDEs.

The present invention also provides methods for using LmPDE nucleotide sequences as nucleic acid probes and primers, and for using LmPDE polypeptides as antigens for the production of novel anti-LmPDE antibodies. The LmPDE probes and primers, and the anti-LmPDE antibodies are useful in diagnostic assays and kits for the detection of naturally occurring LmPDE nucleotide and protein sequences present in biological samples.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

BRIEF DESCRIPTION OF THE DRAWINGS

FIG. 1 shows the deduced amino acid sequence of a full-length LmPDE-A polypeptide (SEQ ID NO: 1).

FIGS. 2A-2S show the DNA sequence (SEQ ID NO: 2) for the full-length gene of LmPDE-A. The open reading frame begins with adenine at position 530 and ends with guanine at position 2425.

FIGS. 3A-3B show the deduced amino acid sequence of a full-length LmPDE-B1 polypeptide (SEQ ID NO: 3).

FIGS. 4A-4L show the DNA sequence (SEQ ID NO: 4) for the full-length gene of LmPDE-B1. The open reading frame begins with adenine at position 1267 and ends with adenine at position 4059.

FIGS. 5A-B show the deduced amino acid sequence of a full-length LmPDE-B2 polypeptide (SEQ ID NO: 5).

FIGS. 6A-6L show the DNA sequence (SEQ ID NO: 6) for the full-length gene of LmPDE-B2. The open reading frame begins with adenine at position 2182 and ends with adenine at position 5004.

FIG. 8 shows the results of a Southern blot analysis for LmPDE-B1 using a conserved region of the LmPDE-B1 sequence as the hybridization probe.

FIG. 10 shows the results of a Southern blot analysis using a conserved region that was specific to both LmPDE-B1 and LmPDE-B2 as the hybridization probe.

FIGS. 12A, 12B, 12C, and 12D show the heat-shock test results of PDE-deficient *Saccharomyces cerevisiae* cells that have been transfected with LmPDE-B1 and LmPDE-A.

FIGS. 13A and 13B show the hydrolysis of cAMP in the absence and presence of a 100-fold excess of cGMP, respectively. FIG. 13C shows the effect of a 50-fold excess of AMP. The figure insets depict the corresponding Eadie-Hofstee plots.

DEFINITIONS

Figure 7A:
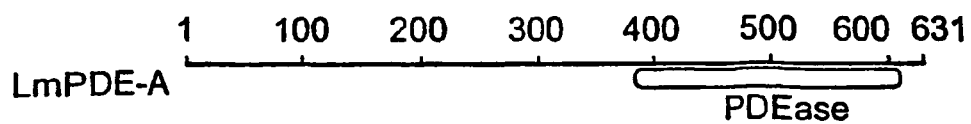
FIGS. 7A, 7B, and 7C show the location of conserved domains that are found in the LmPDE-A, LmPDE-B1, and LmPDE-B2 polypeptide sequences, respectively.

The term "amino acid sequence" refers to amino acids encoding an oligopeptide, peptide, polypeptide, or protein sequence, and fragments thereof, and includes naturally occurring or synthetic molecules.

The term "antibody" refers to intact molecules as well as fragments thereof (e.g., Fab), which can bind an antigenic determinant on an antigen (e.g., an antigenic determinant(s) on a LmPDE). The antibody can be "polyclonal", "monoclonal", "chimeric", "humanized", or human.

The term "antigenic determinant" refers to that fragment of a molecule (i.e., an epitope) that induces an antibody and which thereafter makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense" refers to any composition containing nucleotide sequences which are complementary to a specific DNA or RNA sequence.

The term "antisense strand" is used in reference to a nucleic acid strand that is complementary to the "sense" strand. Antisense molecules include nucleic acids (that can include modified nucleotide base and modified sugar moieties) and may be produced by any method including synthesis or transcription. Once introduced into a cell, the complementary nucleotides combine with natural sequences produced by the cell to form duplexes and block either transcription or translation of the sequences.

The term "biological sample" is used in its broadest sense. A biological sample is suspected of containing LmPDE nucleic acid molecules, or fragments thereof, or a LmPDE polypeptide. The suitable biological sample can be from an animal or a human. The sample can be a cell sample or a tissue sample, including samples from spleen, lymph node, thymus, bone marrow, liver, heart, testis, brain, placenta, lung, skeletal muscle, kidney, and pancreas. The sample can be a biological fluid, including urine, blood sera, blood plasma, phlegm, or lavage fluid. Alternatively, the sample can be a swab from the nose, ear, or throat.

The term "biologically active" refers to a polypeptide having structural, regulatory, or biochemical functions of a naturally occurring molecule. Likewise, "immunologically active" refers to the capability of the natural, recombinant, or synthetic LmPDEs of the invention, or any fragment thereof, to induce a specific immune response in appropriate animals or cells and to bind with specific antibodies. For example, the polypeptides of the invention can elicit antibodies that specifically bind an epitope associated with a LmPDE polypeptide of the invention. Accordingly, a LmPDE polypeptide is capable of inducing a specific immune response in appropriate animals or cells, and/or binding with ligands such as specific antibodies.

The term "catalytic domain" refers to a conserved subset of amino acids within a PDE sequence that is responsible for catalyzing the hydrolysis reaction of the bound substrate.

The term "chimeric antibody" refers to an antibody in which the variable regions derived from one species are combined with the constant regions of an antibody derived from a different species. Chimeric antibodies are useful, as they are less likely to be antigenic to a human subject than antibodies with non-human constant regions and variable regions. The antigen combining region (variable region) of a chimeric antibody can be derived from a non-human source (e.g. murine) and the constant region of the chimeric antibody, which confers biological effector function to the immunoglobulin, can be derived from a human source (Morrison et al. (1985) *Proc. Natl. Acad. Sci. U.S.A.* 81, 6851; Takeda et al. (1985) *Nature* 314, 452; Cabilly et al., U.S. Pat. No. 4,816, 567; Boss et al., U.S. Pat. No. 4,816,397). The chimeric antibody may have the antigen binding specificity of the nonhuman antibody molecule and the effector function conferred by the human antibody molecule.

The term "complementary" refers to nucleic acid molecules having purine and pyrimidine nucleotides which have the capacity to associate through hydrogen bonding to form double stranded nucleic acid molecules. The following base pairs are related by complementarity: guanine and cytosine; adenine and thymine; and adenine and uracil. The term "complementary" applies to all base pairs comprising two single-stranded nucleic acid molecules, or to all base pairs comprising a single-stranded nucleic acid molecule folded upon itself. Complementarity between two single-stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands.

The term "control cell" is a cell that is generally the same, e.g., genotypically and phenotypically, as the cell to which it is being compared (e.g., the cells can be sister cells), but which is not exposed to a test compound.

The term "expression control sequence" or "expression control element" refers to a regulatory polynucleotide sequence that can direct the transcription and translation of an open reading frame. Expression control elements are known in the art and include, but are not limited to, inducible promoters, constitutive promoters, splice donor and acceptor sites, secretion signals, enhancers, transcription terminators, and other transcriptional regulatory elements. Other expression control elements that are involved in translation are known in the art, and include the Shine-Delgarno sequence, and initiation and termination codons.

The term "fragment" of a LmPDE polypeptide refers to a portion of a LmPDE polypeptide. For example, a LmPDE fragment can be a polypeptide with fewer amino acids than a full-length LmPDE, but having the biological activity of a full-length LmPDE-A, LmPDE-B1, or LmPDE-B2 polypeptide, e.g., the ability to hydrolyze cAMP. A fragment can also be a portion of a LmPDE polypeptide that elicits an immune response, or that possesses any other biological or diagnostic property of the full-length LmPDEs of the invention.

The term "fragment" of a LmPDE nucleic acid molecule refers to a portion of a full-length LmPDE nucleotide sequence. For example, such a nucleic acid fragment can encode a LmPDE polypeptide fragment that maintains the biological activity of a full-length LmPDE-A, LmPDE-B1, or LmPDE-B2 polypeptide, e.g., the ability to hydrolyze cAMP (as determined by methods known in the art, e.g., Schilling et al. (1994) *Anal. Biochem.* 216, 154-158).

The term "GAF domain" refers to a highly conserved domain that binds small molecular weight ligands. The GAF domain in some PDEs is known to bind cGMP.

The term "humanized antibody" refers to an antibody molecule in which amino acids have been replaced in the non-antigen binding regions in order to more closely resemble a human antibody, while still retaining the original binding ability. As used herein, a humanized LmPDE antibody is an immunoglobulin molecule that is capable of binding to a LmPDE polypeptide and has variable regions with substantially the same amino acid sequence as a human immunoglobulin, and has a hyper-variable region with substantially the same amino acid sequence as a non-human immunoglobulin.

The term "hybridization" or "hybridize" refers to any process by which a sequence of nucleic acids binds with a complementary strand through base pairing.

The term "hydrolyze" refers to a chemical reaction wherein a chemical bond is cleaved via a water molecule. The catalytic function of LmPDEs of the invention, as with all PDEs, involves the hydrolysis of cAMP (as determined by methods known in the art, e.g., Schilling et al. (1994) *Anal. Biochem.* 216, 154-158).

As used herein, a first amino acid or nucleotide sequence is said to be "identical" to a second reference amino acid or nucleotide sequence, respectively, when a comparison of the first and the second sequences are exactly alike. Two sequences are said to be "X % identical" when a comparison of the first and second sequences have X % of nucleotides or amino acids that are exactly alike. Percent identity can be determined electronically, e.g., by using the MEGALIGN program (DNASTAR) which creates alignments between two or more sequences according to methods selected by the user, e.g., the clustal method (e.g., Higgins et al. (1988) *Gene* 73:237-244). Percent identity between sequences can also be counted or calculated by other methods known in the art (e.g., Hein (1990) *Methods Enzymol.* 183:626-645). Identity between sequences can also be determined by other methods known in the art, e.g., by varying hybridization conditions.

The term "incubate" refers to a process of contacting a cell or a cell culture with the compound of interest, or otherwise introducing the compound of interest into a cell.

The term "inhibitor" refers to an agent which, when bound to a LmPDE, or to some other polypeptide or nucleic acid, decreases the amount (expression) or the biological activity of a LmPDE. Inhibitors may include proteins, nucleic acids, carbohydrates, antibodies or any other molecules which decrease the amount (expression) or biological activity of LmPDEs present in a sample. The preferred inhibitor will selectively inhibit the biological activity of a LmPDE, while not affecting any other cellular proteins.

The term "isolated" or "purified" refers to a specific nucleic acid, protein, or polypeptide, or a fragment thereof, in which contaminants (i.e., substances that differ from the specific nucleic acid, protein, or polypeptide molecule) have been separated or substantially separated from the specific nucleic acid, protein, or polypeptide.

The term "LmPDE" means any of LmPDE-A, LmPDE-B1, or LmPDE-B2, and can refer to the polypeptide or nucleic acid sequences. LmPDE polypeptides can be natural, synthetic, semi-synthetic, or recombinant. LmPDE includes polypeptides from *Leishmania major*, as well as other *Leishmania* species and subspecies from the complexes *Leishmania fropica, Leishmania donovani, Leishmania mexicana,* and *Leishmania viannia* including *Leishmania aethiopica, Leishmania brasiliensis, Leishmania d. donovani, Leishmania d. infantum, Leishmania d. chagasi, Leishmania garnhami, Leishmania m. mexicana, Leishmania m. amazonensis,* and *Leishmania pifanoi*.

The term "LmPDE-A nucleic acid molecule" refers to a nucleic acid molecule that encodes a LmPDE-A polypeptide.

The term "LmPDE-B1 nucleic acid molecule" refers to a nucleic acid molecule that encodes a LmPDE-B1 polypeptide.

The term "LmPDE-B2 nucleic acid molecule" refers to a nucleic acid molecule that encodes a LmPDE-B2 polypeptide.

The term "LmPDE expression" refers to the process whereby a RNA transcript or translated polypeptide is produced from a LmPDE nucleotide sequence.

The term "modulates" refers to a change in the activity of the LmPDEs of the present invention. For example, modulation may cause an increase or a decrease in protein amount (expression) or activity, binding characteristics, or any other biological, functional or immunological properties of the LmPDEs of the invention.

The term "nucleic acid sequence" or "nucleic acid molecule" refers to an oligonucleotide, nucleotide, or polynucleotide, and fragments thereof; to DNA or RNA of genomic or synthetic origin, which may be single- or double-stranded; and represents the sense or antisense strand.

The term "operably linked" refers to functionally related nucleic acid sequences. For example, a promoter is operably linked with a coding sequence if the promoter controls the translation of the encoded polypeptide. While operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "PDEase domain" refers to the conserved catalytic domain of PDEs.

The term "stringent conditions" refers to conditions which permit hybridization between complementary polynucleotide sequences. Suitably-stringent conditions can be defined by, for example, the concentrations of salt and/or formamide in the pre-hybridization and hybridization solutions, or by the hybridization temperature, which are well known in the art. In particular, stringency can be increased by reducing the concentration of salt, increasing the concentration of formamide, or raising the hybridization temperature.

The term "substantially purified" refers to nucleic acid or polypeptide sequences that are removed from their natural environment and are isolated or separated, and are at least 60% free, 65% free, 70% free, 75% free, 80% free, 85% free, 90% free, 95% free, 96% free, 97% free, 98% free, or 99% free from other components with which they are naturally associated.

The term "variants and mutants" refers to changes in a polypeptide or nucleic acid sequence such as amino acid or nucleotide substitutions, insertions, deletions, conservative amino acid changes, polymorphic changes, allelic changes, frame shift changes, truncations, or the like, wherein the variant or mutant protein maintains its native function (here, at least the hydrolysis of cAMP) and wherein the variant or mutant nucleic acid molecule encodes a protein that maintains its native function.

The term "vector" includes, but is not limited to, plasmids, cosmids, and phagemids.

DETAILED DESCRIPTION OF THE INVENTION

Second messengers such as cyclic adenosine mono-phosphate (cAMP) and cyclic guanosine mono-phosphate (cGMP) play important biological roles in modulating the effects of a wide variety of first messengers. For example, cAMP and cGMP are involved in the propagation of a variety of extracellular signals that originate from first messengers such as hormones, light, and neurotransmitters. The steady state intracellular levels of cAMP and cGMP are controlled by their rates of synthesis by cyclases and by their rate of degradation by cyclic nucleotide-specific phosphodiesterases (PDEs).

PDEs are typically composed of a catalytic domain (approximately 270 amino acids), an N-terminal regulatory domain responsible for binding cofactors, and, in some cases, a C-terminal domain of unknown function. A conserved motif, HDXXHXGXXN, has been found in the catalytic domain of all PDEs. Several families of PDEs have been identified (Beavo (1995) *Physiol. Rev.* 75, 725-748; Soderling et al. (1998) *J. Biol. Chem.* 273, 15553-15558; and Fisher et al. (1998) *J. Biol. Chem.* 273, 15559-15564). PDE families display roughly 35% amino acid sequence identity within their catalytic domain. Isozymes within the same family typically display 75-95% sequence identity in this region. Within a family, there is often greater than 60% sequence identity outside the catalytic domain, whereas across different PDE families, there is little or no sequence similarity.

In eukaryotes, two distinct classes of PDEs have been identified. Class I enzymes all show significant amino acid sequence conservation within their catalytic domains. Class I PDEs include all currently known families of mammalian PDEs as well as several PDEs from lower eukaryotes such as PDE2 from *Saccharomyces cerevisiae* and the regA gene product from *Dictyostelium discoideum*. Class II PDEs, however, share very little amino acid sequence identity with class I PDEs, and thus likely have a different evolutionary origin. Furthermore, class II PDEs are often distinguished by their generally higher $K_M$ values (Zoraghi et al. (2001) *J. Biol. Chem.* 276, 11559-11566). Class II PDEs have been identified in yeast (Nikawa et al. (1987) *Mol. Cell. Biol.* 7, 3629-3636), the slime mold *Dictyostelium discoideum* (Lacombe et al. (1986) *J. Biol. Chem.* 261, 16811-16817), *Vibrio fisheri* (Dunlap et al. (1993) *J. Bacteriol.* 175, 4615-4624), and *Candida albicans* (Hoyer et al. (1994) *Microbiology* 140, 1533-1542).

A variety of diseases are thought to result from decreased levels of cyclic nucleotides due to increased PDE activity. Accordingly, PDEs have become highly attractive drug targets over the last several years. A growing number of family-specific and subtype-specific PDE inhibitors are being developed as therapeutic agents for a wide range of diseases such as autoimmune disease (Bielekova et al. (2000) *J. Immunol.* 164, 1117-1124), arthritis (Kiely et al. (1995) *Eur. J. Immunol.* 25, 2899-2906), asthma (Barnette (1999) *Prog. Drug Res.* 53, 193-229), inflammatory diseases (Barnes (2001) *Novartis Found. Symp.* 234, 255-267) impotency (Langtry et al. (1999) *Drugs* 57, 967-989) and cancer (Marko et al. (2000) *Chem. Res. Toxicol.* 10, 944-948). So far, there is limited information about PDEs in kinetoplastids such as *Leishmania major*.

Polypeptides of the Invention

One aspect of the present invention is directed to novel, isolated PDE polypeptides from the parasite *Leishmania major*, designated LmPDE-A (SEQ ID NO: 1), LmPDE-B1 (SEQ ID NO: 3), and LmPDE-B2 (SEQ ID NO: 5). Particular embodiments of the LmPDE polypeptides of the invention include full-length LmPDE-A, LmPDE-B1, and LmPDE-B2 from *Leishmania major*. In another aspect, the invention relates to fragments of LmPDEs. The invention also provides polypeptides comprising biologically and/or immunologically active fragments of LmPDEs.

The present invention also relates to variants and mutants of LmPDEs. Mutant alleles of LmPDEs encode mutant forms of LmPDE polypeptides having at least one amino acid substitution, insertion, deletion, truncation, or frame shift. Such mutant forms of polypeptides may not exhibit the same biological activity as wild-type proteins (e.g., they may have less PDE activity or an activity not normally found in LmPDE polypeptides, such as, for example, not functioning as a PDE).

Another variant of LmPDE polypeptides may have amino acid sequences that differ by one or more amino acid substitutions. The variant may have conservative amino acid changes, where a substituted amino acid has similar structural or chemical properties. Amino acid residues that can be conservatively substituted for one another include, but are not limited to: glycine/alanine; valine/isoleucine/leucine; asparagine/glutamine; aspartic acid/glutamic acid; serine/threonine; lysine/arginine; and phenylalanine/tyrosine. Other substitutions can also be considered conservative, depending on the environment of the particular amino acid and its role in the three-dimensional structure of the protein. For example, methionine, which is relatively hydrophobic, can frequently be interchanged with leucine and isoleucine, and sometimes with valine.

Alternatively, a variant may have nonconservative amino acid changes, such as, for example, replacement of a glycine with a tryptophan, or alanine with lysine. Similar minor variations may also include amino acid deletions and insertions. Any amino acid substitution that does not significantly affect the biological and/or chemical properties of LmPDE polypeptides is encompassed by the present invention. Guidance in determining which and how many amino acid residues may be substituted, inserted and deleted may be found using computer programs well known in the art such as the DNASTAR software package.

The present invention also encompasses various amino acid sequences that represent different forms and fragments of the LmPDE polypeptides such as polypeptides with conservative mutations and fragments containing the PDEase domain. The LmPDE polypeptides may be from *Leishmania major*, or other *Leishmania* species and subspecies of the complexes *Leishmania tropica, Leishmania donovani, Leishmania mexicana*, and *Leishmania viannia* including *Leishmania aethiopica, Leishmania brasiliensis, Leishmania d. donovani, Leishmania d. infantum, Leishmania d. chagasi, Leishmania garnhami, Leishmania m. mexicana, Leishmania m. amazonensis*, and *Leishmania pifanoi*.

The LmPDEs of this invention may be embodied in many forms, such as in isolated form or in purified form. A skilled artisan can readily employ standard isolation and purification methods to obtain isolated LmPDE polypeptides (see, e.g., Marchak et al. (1996) *Strategies for Protein Purification and Characterization*, Cold Spring Harbor Press, Plainview, N.Y.). The nature and degree of isolation and purification will depend on the intended use. For example, purified LmPDE protein molecules will be substantially free of other proteins or molecules that impair the binding of LmPDE proteins to antibodies or other ligands. Embodiments of LmPDE polypeptides include purified LmPDE polypeptides having the biological activity of a LmPDE protein. In one form, such purified LmPDE polypeptides retain the ability to bind antibody or other ligand.

Various forms of a particular LmPDE polypeptide of the invention may be produced as a result of processes such as post-translational modifications. For example, various forms of isolated LmPDE polypeptides may include precursor forms and different mature forms of a LmPDE protein or polypeptide that result from posttranslational events, such as glycosylation, phosphorylation, and intramolecular cleavage.

The present invention provides isolated and purified polypeptides having an amino acid sequence identical to the predicted LmPDE polypeptide sequences disclosed herein. Accordingly, the amino acid sequences of the present invention may be identical to LmPDE-A (SEQ ID NO: 1), LmPDE-B1 (SEQ ID NO: 3) or LmPDE-B2 (SEQ ID NO: 5). LmPDE polypeptides of the invention may also comprise at least one sequence that is identical to a fragment of a full-length LmPDE polypeptide sequence. The present invention also provides isolated and purified polypeptides with at least about 60%, 65%, 70%, 75%, 80%, 85%, 90%, 95%, 96%, 97%, 98%, or 99% identity to the sequences disclosed herein.

Nucleic Acid Molecules of the Invention

The present invention provides LmPDE nucleic acid molecules corresponding to the full length genes of LmPDE-A (SEQ ID NO: 2), LmPDE-B1 (SEQ ID NO: 4), and LmPDE-B2 (SEQ ID NO: 6). The present invention also provides nucleic acid molecules that encode the LmPDE polypeptides discussed previously. The present invention also encompasses various nucleotide sequences that represent different forms and fragments of LmPDE genes and transcripts, such as different allelic forms, polymorphic forms, alternative precursor transcripts, and mature transcripts. Additionally, recombinant nucleic acid molecules that are codon usage variants of novel LmPDE sequences are provided.

In one embodiment, the present invention provides a nucleic acid encoding a LmPDE-A polypeptide of the present invention comprising the nucleotide sequence shown in SEQ ID NO: 2, beginning with adenine at position 530 and ending with guanine at position 2425 (which corresponds to amino acids 1-631 of SEQ ID NO: 1). Another embodiment comprises a nucleotide sequence found in SEQ ID NO: 2, beginning with thymine at position 1679 and ending with cytosine at position 2356, which corresponds to the PDEase domain of a LmPDE-A polypeptide (amino acids 384-609 of SEQ ID NO:1). Due to the degeneracy of the genetic code, the present invention also provides any nucleic acid molecule that encodes a polypeptide comprising the LmPDE-A polypeptide sequence set forth in SEQ ID NO: 1, beginning with methionine at amino acid position 1 and ending with serine at amino acid position 631. The invention also provides nucleic acids that encode fragments of a LmPDE-A, for example a nucleic acid that encodes the PDEase domain comprising amino acids 384-609 as set forth in SEQ ID NO: 1.

A specific embodiment of a nucleic acid encoding a LmPDE-B1 polypeptide of the present invention comprises the nucleotide sequence of SEQ ID NO: 4, beginning with adenine at position 1267 and ending with adenine at position 4059 (which corresponds to amino acids 1-930 of SEQ ID NO: 3). Another embodiment comprises a nucleotide sequence found in SEQ ID NO: 4, beginning with thymine at position 3205 and ending with cytosine at position 3906, which corresponds to the PDEase domain of LmPDE-B1 (amino acids 647-880 of SEQ ID NO: 3). Due to the degeneracy of the genetic code, the present invention also provides any nucleic acid molecule that encodes a polypeptide comprising the LmPDE-B1 polypeptide sequence set forth in SEQ ID NO: 3, beginning with methionine at amino acid position 1 and ending with valine at amino acid position 930. The invention also provides nucleic acids that encode fragments of a LmPDE-B1 polypeptide, for example a nucleic acid that encodes the PDEase domain comprising amino acids 647-880 as set forth in SEQ ID NO: 3.

A specific embodiment of a nucleic acid encoding a LmPDE-B2 polypeptide of the present invention comprises the nucleotide sequence of SEQ ID NO: 6, beginning with adenine at position 2182 and ending with adenine at position 5004 (which corresponds to amino acids 1-940 of SEQ ID NO: 5). Another embodiment comprises a nucleotide sequence found in SEQ ID NO: 6, beginning with thymine at position 4150 and ending with cytosine at position 4851, which corresponds to the PDEase domain of LmPDE-B2 (amino acids 657-890 of SEQ ID NO: 5). Due to the degeneracy of the genetic code, the present invention also provides any nucleic acid molecule that encodes a polypeptide comprising the LmPDE-B2 polypeptide sequence set forth in SEQ ID NO: 5, beginning with methionine at amino acid position 1 and ending with valine at amino acid position 940. The invention also provides nucleic acids that encode fragments of a LmPDE-B2 polypeptide, for example a nucleic acid that encodes the PDEase domain comprising amino acids 657-890 as set forth in SEQ ID NO: 5.

One of skill in the art will appreciate that nucleic acids of the present invention can encode domains or portions of LmPDE polypeptides other than those specifically mentioned above.

The present invention contemplates alternative allelic forms of LmPDE nucleotide sequences that are isolated from different subjects of the same species. Typically, isolated allelic forms of naturally-occurring gene sequences include wild-type and mutant alleles. A wild-type LmPDE gene sequence will encode a LmPDE protein having normal PDE biological activity, such as, for example, a phosphodiesterase function. A mutant of a LmPDE gene sequence may encode a LmPDE polypeptide having an activity not normally found in LmPDE polypeptides, such as, for example, not functioning as a phosphodiesterase. Alternatively, a mutant of a LmPDE gene sequence may encode a LmPDE polypeptide having normal activity. Accordingly, the present invention provides wild-type and mutant allelic forms of LmPDE nucleotide sequences.

The present invention further contemplates polymorphic forms of LmPDE nucleotide sequences. Typically, isolated polymorphic forms of naturally-occurring gene sequences are isolated from different subjects of the same species. The polymorphic forms include sequences having one or more nucleotide substitutions that may or may not result in changes in the amino acid codon sequence. These substitutions may result in a wild-type LmPDE gene that encodes a protein having the biological activity of wild-type LmPDE proteins, or encodes a mutant polymorphic form of the LmPDE protein having a different or null activity.

The present invention further provides isolated codon-usage variants (see Table 1) that differ from the disclosed LmPDE nucleotide sequences, yet do not alter the predicted LmPDE protein sequence or biological activity. The codon-usage variants may be generated by recombinant DNA technology. Codons may be selected to optimize the level of production of the LmPDE transcript or LmPDE protein in a particular prokaryotic or eukaryotic expression host, in accordance with the frequency of codons utilized by the host cell. Alternative reasons for altering the nucleotide sequence encoding a LmPDE protein include the production of RNA transcripts having more desirable properties, such as an extended half-life or increased stability.

TABLE 1

| Amino Acid | Symbol | One Letter Symbol | Codons |
| --- | --- | --- | --- |
| Alanine | Ala | A | GCU, GCC, GCA, GCG |
| Cysteine | Cys | C | UGU, UGC |
| Aspartic Acid | Asp | D | GAU, GAC |

TABLE 1-continued

| Amino Acid | Symbol | One Letter Symbol | Codons |
| --- | --- | --- | --- |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The present invention further provides novel purified and isolated polynucleotides (i.e. DNA sequences and fragments thereof), which can be in isolated form, including DNA and RNA transcripts (both sense and complementary antisense strands) encoding LmPDEs, DNA/RNA hybrids, and related molecules. The nucleic acid molecules of the present invention include nucleotide sequences substantially identical to or complementary to the LmPDE nucleotide sequences disclosed herein.

The invention encompasses genomic, cDNA, ribozyme, and antisense molecules, as well as nucleic acids based on alternative backbone and including alternative bases and modified sugar moieties, whether derived from natural sources or wholly or partially synthesized. As used herein, "wholly" synthesized DNA means that the DNA is produced entirely by chemical means, and "partially" synthesized means that only portions of the resulting DNA are produced by chemical synthesis. Antisense molecules can be RNAs or other molecules, including peptide nucleic acids (PNAs) or non-nucleic acid molecules such as phosphorothioate derivatives (described in greater detail below) that specifically bind DNA or RNA in a base-pair dependent manner. A skilled artisan can readily obtain these classes of nucleic acid molecules using the sequences described herein.

The present invention further provides nucleotide sequences that selectively hybridize to LmPDE nucleotide sequences under high stringency hybridization conditions. Typically, hybridization under standard high stringency conditions will occur between two complementary nucleic acid molecules that differ in sequence complementarity by about 70% to about 100%. It is readily apparent to one skilled in the art that the high stringency hybridization between nucleic acid molecules depends upon, for example, the degree of identity, the stringency of hybridization, and the length of the hybridizing strands. The methods and formulas for conducting high stringency hybridizations are well known in the art, and can be found, for example, in Sambrook, et al. (2001) *Molecular Cloning: A Laboratory Manual* (Cold Spring Harbor Laboratory, Cold Spring Harbor, N.Y.).

In general, stringent hybridization conditions are those that: (1) employ low ionic strength and high temperature for washing, for example, 0.015 M NaCl, 0.0015 M sodium citrate, and 0.1% SDS at 50° C.; or (2) employ a denaturing agent during hybridization such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, and 75 mM sodium citrate at 42° C.

Another example of stringent conditions is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Typical ranges of stringency conditions include: (1) low stringency (2×SSC/0.1% (w/v) SDS, room temperature), (2) moderate stringency (0.2×SSC/0.1% (w/v) SDS, 42° C.), and (3) high stringency (0.1×SSC/0.1% (w/v) SDS, 68° C.).

The present invention provides RNA molecules that encode LmPDE polypeptides. In particular, the RNA molecules of the invention may be isolated full-length or partial mRNA molecules or RNA oligomers that encode a LmPDE polypeptide.

The nucleic acid molecules of the invention also include derivative nucleic acid molecules which differ from DNA or RNA molecules, and anti-sense molecules. Derivative molecules include peptide nucleic acids (PNAs), and non-nucleic acid molecules including phosphorothioate, phosphotriester, phosphoramidate, and methylphosphonate molecules, that bind to single-stranded DNA or RNA in a base pair-dependent manner (Zamecnik et al. (1978) *Proc. Natl. Acad. Sci. USA* 75, 280-284; Goodchild et al. (1986) *Proc. Natl. Acad. Sci. USA* 83, 4143-4146).

Peptide nucleic acid molecules comprise a nucleic acid oligomer to which an amino acid residue, such as lysine, and an amino group have been added. These small molecules (also known as anti-gene agents) stop transcript elongation by binding to their complementary (template) strand of nucleic acid (Nielsen et al., (1993) *Anticancer Drug Des.* 8, 53-63). Reviews of methods for synthesis of DNA, RNA, and their analogues can be found in *Oligonucleotides and Analogues* (ed. F. Eckstein (1991) IRL Press, New York) and *Oligonucleotide Synthesis* (ed. M. J. Gait (1984) IRL Press, Oxford, England). Additionally, methods for antisense RNA technology are described in U.S. Pat. Nos. 5,194,428 and 5,110,802. A skilled artisan can readily obtain these classes of nucleic acid molecules using the LmPDE nucleotide sequences described herein (see, for example, *Innovative and Perspectives in Solid Phase Synthesis* (1992) Egholm, et al. pp. 325-328, or U.S. Pat. No. 5,539,082).

Embodiments of the LmPDE nucleic acid molecules of the invention include DNA and RNA primers, which allow the specific amplification of LmPDE sequences, or of any fragments thereof, and probes that selectively or specifically hybridize to LmPDE sequences or to any fragments thereof.

As used herein, amplification refers to the production of additional copies of a nucleic acid sequence and is generally carried out using polymerase chain reaction (PCR) technologies that are well known in the art (Dieffenbach et al. (1995) PCR Primer, a Laboratory Manual, Cold Spring Harbor Press, Plainview, N.Y.). The nucleic acid probes can be labeled with a detectable marker. Examples of a detectable marker include, but are not limited to, a radioisotope, a fluorescent compound, a bioluminescent compound, a chemiluminescent compound, a metal chelator, or an enzyme. Technologies for generating labeled DNA and RNA probes are well known in the art (see, for example, Sambrook et al. (1989) in *Molecular Cloning*).

Recombinant Nucleic Acid Molecules Encoding LmPDEs

The invention also includes recombinant nucleic acid molecules encoding LmPDE polypeptides. Such molecules may have regulatory sequences operatively linked to the LmPDE nucleotide sequences of the invention.

The present invention also encompasses recombinant nucleic acid molecules, such as recombinant DNA molecules (rDNAs) that comprise nucleotide sequences encoding LmPDE polypeptides. As used herein, a rDNA molecule is a DNA molecule that has been subjected to molecular manipulation in vitro. Methods for generating rDNA molecules are well known in the art (see, for example, Sambrook et al. (1989) *Molecular Cloning*, supra). In one embodiment of the present invention, the rDNA sequences that encode a LmPDE polypeptide, or fragments thereof, are operably linked to one or more expression control sequences and/or vector sequences.

Vectors Comprising Novel LmPDEs

The nucleic acid molecules of the present invention may be recombinant molecules, each comprising the sequence, or portion thereof, of a LmPDE nucleotide sequence linked to a non-LmPDE nucleotide sequence. For example, the LmPDE sequence may be operatively linked to a vector to generate a recombinant molecule.

One possible vector for expression is an autonomously replicating vector comprising a replicon that directs the replication of the rDNA within the appropriate host cell. Alternatively, the vector directs integration of the recombinant vector into a host cell. Various viral vectors may also be used, such as a number of well known retroviral, adenoviral, and adeno-associated viral (MV) vectors (Berkner (1988) *Biotechniques* 6, 616-629).

Vectors of the present invention may permit expression of a LmPDE transcript or polypeptide sequence in prokaryotic or eukaryotic host cells. Such vectors include expression vectors comprising an expression control element, described above. Vectors used for expression of the LmPDE nucleotide sequences in eukaryotic host cells can include expression control elements, such as the baculovirus polyhedrin promoter for expression in insect cells. Other possible expression control elements include promoters or enhancers derived from the genomes of plant cells (e.g., heat shock, RUBISCO, storage protein genes), viral promoters or leader sequences from plant viruses, and promoters or enhancers from the mammalian genes or from mammalian viruses.

Specific initiation signals may also be required for efficient translation of LmPDE nucleotide sequences. These signals include the ATG-initiation codon and adjacent sequences. In cases where a LmPDE initiation codon and upstream sequences are inserted into the appropriate expression vector, no additional translation control signals may be needed. However, in cases where only the coding sequence (or a portion thereof) is inserted, exogenous translational control signals including the ATG-initiation codon must be provided.

Furthermore, the initiation codon must be in the correct reading frame to ensure translation of the entire insert. Exogenous translational elements and initiation codons can be of various origins, both natural and synthetic. The efficiency of expression may be enhanced by the inclusion of enhancers appropriate to the cell system in use (Scharf et al (1994) *Results ProbL Cell. Differ.* 20, 125-162; Bittner et al. (1987) *Methods in Enzymol.* 153, 516-544).

One possible vector includes at least one selectable marker gene that encodes a gene product that confers drug resistance such as resistance to ampicillin or tetracyline. The vector may also comprise multiple endonuclease restriction sites that enable convenient insertion of exogenous DNA sequences. Methods for generating a recombinant expression vector encoding a LmPDE protein of the invention are well known in the art (see, for example, Sambrook et al. (2001) *Molecular Cloning, A Laboratory Manual*, Cold Spring Harbor Laboratory, Cold Spring Harbor, N.Y. and Ausubel (1989) *Current Protocols in Molecular Biology*, John Wiley & Sons, New York N.Y.).

Vectors of the present invention for generating LmPDE transcripts and/or the encoded LmPDE polypeptides can be expression vectors that are compatible with prokaryotic host cells. Prokaryotic cell expression vectors are well known in the art and are available from several commercial sources. For example, pET vectors (e.g., pET-21, Novagen Corp.), pQE vectors (Qiagen, Chatsworth, Calif.), BLUESCRIPT phagemid (Stratagene, LaJolla, Calif.), pSPORT (Gibco BRL), or ptrp-lac hybrids may be used to express LmPDE polypeptides in bacterial host cells.

Alternatively, the expression vectors of the present invention for generating LmPDE transcripts and/or the encoded LmPDE polypeptides can be expression vectors which are compatible with eukaryotic host cells, such as vertebrate cells. Eukaryotic cell expression vectors are well known in the art and are available from several commercial sources. Such vectors can contain convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), and similar eukaryotic expression vectors.

Host-Vector Systems Comprising LmPDEs

The invention further provides a host-vector system comprising a vector, plasmid, phagemid, or cosmid comprising a LmPDE nucleotide sequence, or a fragment thereof, introduced into a suitable host cell. A variety of expression vector/host systems may be utilized to carry and express LmPDE nucleotide sequences. The host-vector system can be used to express (e.g., produce) LmPDE polypeptides encoded by LmPDE nucleotide sequences. The host cell can be either prokaryotic or eukaryotic. Examples of suitable prokaryotic host cells include bacterial strains from genera such as *Escherichia, Bacillus, Pseudomonas, Streptococcus,* and *Streptomyces*. Examples of suitable eukaryotic host cells include yeast cells, plant cells, or animal cells such as mammalian cells and insect cells. Several possible embodiments provide a host-vector system comprising the pcDNA3 vector (Invitrogen, Carlsbad, Calif.) in COS-7 mammalian cells, pGEX vector (Promega, Madison, Wis.) in bacterial cells, pLT1 vector (S. Kunz, unpublished) in *Saccharomyces cerevisiae* cells, or pFastBac HT baculovirus vector (Gibco/BRL) in Sf9 insect cells (ATCC, Manassas, Va.).

The introduction of the recombinant DNA molecules of the present invention into an appropriate host cell may be accomplished by well-known methods that depend on the type of vector and host system employed. For example, prokaryotic host cells are introduced (e.g., transformed) with nucleic acid molecules by electroporation or salt treatment methods (see, for example, Cohen et al. (1972) *Proc Natl Acad Sci USA* 69, 2110; Sambrook et al. (1989) *Molecular Cloning* supra). Vertebrate cells can be transformed with vectors containing recombinant DNAs by various methods, including electroporation, or cationic lipid or salt treatment (Graham et al. (1973) *Virol.* 52, 456; Wigler et al. (1979) *Proc. Natl. Acad. Sci. USA* 76, 1373-1376).

Successfully transformed cells, i.e., cells that contain a rDNA molecule of the present invention, can be identified by techniques well known in the art. For example, cells resulting from the introduction of recombinant DNA of the present invention are selected and cloned to produce single colonies. Cells from those colonies are harvested, lysed and their DNA content examined for the presence of the rDNA using a method such as that described by Southern (1975) *J. Mol. Biol.* 98, 503, or Berent et al. (1985) *Biotech.* 3, 208. The proteins produced from the cell may also be assayed via a biochemical assay or immunological method.

In bacterial systems, a number of expression vectors may be selected depending upon the use intended for the LmPDE polypeptides. For example, when large quantities of LmPDEs are needed for the induction of antibodies, vectors that direct high level expression of fusion proteins that are soluble and readily purified may be desirable. Such vectors include, but are not limited to, the multifunctional *E. coli* cloning and expression vectors such as BLUESCRIPT (Stratagene, San Diego, Calif.), into which a LmPDE nucleotide sequence may be ligated in-frame with sequences for the amino-terminal Met and the subsequent 7 residues of β-galactosidase so that a hybrid protein is produced; pIN vectors (Van Heeke & Schuster (1989) *J. Biol. Chem.* 264, 5503-5509); and the like. The pGEX vectors (Promega, Madison, Wis.) may also be used to express LmPDE polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned protein of interest can be released from the GST moiety at will.

In yeast (*Saccharomyces cerevisiae*) a number of vectors containing constitutive or inducible promoters such as beta-factor, alcohol oxidase and PGH may be used. For reviews, see Ausubel et al. (supra) and Grant et al. (1987) *Methods in Enzymology* 153, 516-544.

In cases where plant expression vectors are used, the expression of a sequence encoding a LmPDE polypeptide can be driven by several different promoters. For example, viral promoters such as the 35S and 19S promoters of CaMV (Brisson et al. (1984) *Nature* 310, 511-514) may be used alone or in combination with the omega leader sequence from TMV (Takamatsu et al. (1987) *EMBO J.* 6, 307-311). Alternatively, plant promoters such as the small subunit of RUBISCO (Coruzzi et al (1984) *EMBO J.* 3, 1671-1680; Broglie et al. (1984) *Science* 224, 838-843), or heat shock promoters (Winter et al. (1991) *Results ProbL. Cell Differ.* 17, 85-105) may be used. These constructs can be introduced into plant cells by direct DNA transformation or pathogen-mediated transfection. For reviews of such techniques, see Hobbs (1992) *McGraw Yearbook of Science and Technology*, McGraw Hill New York N.Y., pp. 191-196, or Weissbach and Weissbach (1988) *Methods for Plant Molecular Biology*, Academic Press, New York N.Y., pp. 421-463.

An alternative expression system that can be used to express LmPDE polypeptides is an insect system. In one such system, *Autographa californica* nuclear polyhedrosis virus (AcNPV) is used as a vector to express foreign genes in *Spodoptera frugiperda* cells or in *Trichoplusia larvae* (Smith et al. (1983) *J. Virol.* 46, 584; Engelhard et al. (1994) *Proc. Nat. Acad. Sci. USA* 91, 3224-3227). The sequence encoding a LmPDE polypeptide may be cloned into a nonessential region of the virus, such as the polyhedrin gene, and placed under control of the polyhedrin promoter. Successful insertion of a LmPDE nucleotide sequence will render the polyhedrin gene inactive and produce recombinant virus lacking coat protein. The recombinant viruses are then used to infect *S. frugiperda* cells or *Trichoplusia larvae* in which a LmPDE polypeptide is expressed.

In mammalian host cells, a number of viral-based expression systems are utilized. In cases where an adenovirus is used as an expression vector, a LmPDE nucleotide sequence is ligated into an adenovirus transcription/translation vector consisting of the late promoter and tripartite leader sequence. Insertion in a nonessential E1 or E3 region of the viral genome results in a viable virus (Logan et al. (1984) *Proc Natl. Acad. Sci. USA* 81, 3655-3659) capable of expressing a LmPDE protein in infected host cells. In addition, transcription enhancers, such as the rous sarcoma virus (RSV) enhancer, can be used to increase expression in mammalian host cells.

A host cell strain may also be chosen for its ability to modulate the expression of the inserted LmPDE nucleotide sequences or to process the expressed LmPDE polypeptide in a particular manner. Such modifications of LmPDE polypeptides include, but are not limited to, acetylation, carboxylation, glycosylation, phosphorylation, lipidation and acylation. Post-translational processing which cleaves a precursor form of the protein may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines that stably express LmPDE polypeptides are transformed using expression vectors that contain viral origins of replication or endogenous expression elements and a selectable marker gene. Following the introduction of the vector, cells are grown in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate for the cell type used.

Any number of selection systems may be used to recover transformed cell lines. These include, but are not limited to, the herpes simplex virus thymidine kinase (tk) (Wigler et al. (1977) *Cell* 11, 223-232) and adenine phosphoribosyltransferase (aprt) (Lowy et al. (1980) *Cell* 22, 817-823) genes which can be employed in tk-minus or aprt-minus cells, respectively. Also, antimetabolite, antibiotic or herbicide resistance can be used as the basis for selection. Examples include: dhfr which confers resistance to methotrexate (Wigler et al. (1980) *Proc Natl Acad Sci USA* 77, 3567-3570); npt, which confers resistance to the aminoglycosides neomycin and G-418 (Colbere-Garapin et al. (1981) *J. Mol. Biol.* 150, 1-14) and als or pat, which confer resistance to chlorsulfaron and phosphinotricin acetyltransferase, respectively (Murry, supra).

Additional selectable genes have been described, for example, UpB, which allows cells to utilize indole in place of tryptophan, or hisD, which allows cells to utilize histinol in place of histidine (Hartman et al. (1988) *Proc. Natl. Acad. Sci. USA* 85, 8047-8051). Recently, the use of visible markers has gained popularity. Such markers include anthocyanins, β-glucuronidase and its substrate, GUS, and luciferase and its substrate, luciferin. These markers are widely used not only to identify transformants, but also to quantify the amount of transient or stable protein expression attributable to a specific vector system (Rhodes et al. (1995) *Methods Mol. Biol.* 55, 121-131).

Antibodies Reactive Against LmPDE Polypeptides

The present invention also provides antibodies that bind to the LmPDEs of the invention. These antibodies may be used for both diagnostic and therapeutic purposes.

The invention provides antibodies, such as polyclonal, monoclonal, chimeric, humanized, and human antibodies, as well as fragments thereof (e.g., Fab), that bind to LmPDE polypeptides. Such antibodies may selectively bind to a LmPDE polypeptide but will not bind (or will bind weakly) to a non-LmPDE protein. These antibodies can be from any source, e.g., rabbit, sheep, rat, dog, cat, pig, horse, mouse and human.

As will be understood by those skilled in the art, the epitopes of a LmPDE polypeptide to which an antibody is directed may vary with the intended application. LmPDE polypeptides may be targets for therapeutic methods such as targeted antibody therapy and immunotherapy to treat conditions associated with the presence or absence of a LmPDE of the invention. Additionally, some of the antibodies of the invention may be internalizing antibodies, which internalize (e.g., enter) into the cell upon or after binding. Internalizing antibodies are useful for inhibiting cell growth and/or inducing cell death and for detecting or targeting LmPDEs within damaged or dying cells.

The invention also encompasses antibody fragments that specifically recognize a LmPDE polypeptide. As used herein, an antibody fragment is defined as at least a portion of the variable region of the immunoglobulin molecule that binds to its target, i.e., the antigen-binding region. Some of the constant region of the immunoglobulin may be included. Fragments of the monoclonal antibodies or the polyclonal antisera include Fab, F(ab')$_2$, Fv fragments, single-chain antibodies, and fusion proteins which include the immunologically significant portion (i.e., a portion that recognizes and binds a LmPDE).

The chimeric antibodies of the invention may be immunoglobulin molecules that comprise at least two antibody portions from different species, for example a human and non-human portion. The invention also provides chimeric antibodies having different effector functions (Neuberger et al. (1984) *Nature* 312, 604), immunoglobulin constant regions from another species, and constant regions of another immunoglobulin chain (Sharon et al. (1984) *Nature* 309, 364; Tan et al. (1985) *J. Immunol.* 135, 3565-3567). Additional procedures for modifying antibody molecules and for producing chimeric antibody molecules using homologous recombination to target gene modification have been described (Fell et al. (1989) *Proc. Natl. Acad. Sci. USA* 86, 8507-8511).

Humanized antibodies directed against LmPDE polypeptides are also useful. Humanized antibodies can be made according to several methods known in the art (Teng et al. (1983) *Proc. Natl. Acad. Sci. USA* 80, 7308-7312; Kozbor et al. (1983) *Immunology Today* 4, 7279; Olsson et al. (1982) *Meth. Enzymol.* 92, 3-16).

Various methods for the preparation of antibodies are well known in the art. For example, antibodies may be prepared by immunizing a suitable mammalian host with an immunogen such as an isolated LmPDE polypeptide (Harlow (1989) *Antibodies*, Cold Spring Harbor Press, NY). In addition, fusion proteins of LmPDEs may also be used as immunogens, such as a LmPDE fused to GST, human Ig, or His-tagged fusion proteins. Cells expressing or over-expressing LmPDE polypeptides may also be used for immunizations. This strategy may result in the production of monoclonal antibodies with enhanced capacities for recognizing endogenous LmPDE polypeptides (Harlow et al. (1988) *Antibodies: A Laboratory Manual*, Cold Spring Harbor Press).

The invention also provides for human antibodies. There are a number of well-known strategies one of ordinary skill in the art may use to produce human recombinant antibodies. One is the generation of antibodies using phage display technologies (Low et al. (1996). *J Mol Biol* 260(3):359-368; Winter et al. (1994). *Annu Rev Immunol* 12:433-455). Specifically, human RNA is used to produce a cDNA library of antibody heavy and light chain fragments expressed on the surface of bacteriophage. These libraries can be used to probe against the antigen of interest. The phage that bind, because of the antibody expressed on the surface, can then be isolated. The DNA encoding the variable regions is sequenced and cloned for antibody expression.

Another method of producing human antibodies employs "humanized" mice. These transgenic mice have had their own antibody genes replaced with a portion of the human antibody gene complex so that upon inoculation with antigen, they produce human antibodies (Green et al. (1994) *Nat. Genet.* 7:13-21; Low et al. (1996). *J Mol Biol* 260(3):359-368; Wagner et al. (1994) *Eur. J. Immunol.* 24(11):2672-2681; Wagner et al. (1994) *Nuc. Acids Res.* 22(8): 1389-1393; Winter et al. (1994) *Annu Rev. Immunol.* 12:433-455). The antibody producing cells that result can then be incorporated into the standard hybridoma technology for the establishment of specific monoclonal antibody producing cell lines.

Recombinant human antibodies are also produced by isolating antibody-producing B cells from human volunteers that have a robust response against the antigen of interest. Using fluorescence activated cell sorting (FACS) and fluorescently labeled antigen, cells producing the antibodies directed against the antigen can be separated from the other cells. The RNA can then be extracted and the sequence of the reactive antibody variable regions determined (Kantor et al. (1995) *Ann. N.Y. Acad. Sci.* 764:224-227, Wang et al. (2000) *J. Immunol. Methods* 244:217-225). The DNA sequence of the functional variable regions can be synthesized or cloned into mammalian expression vectors for large-scale human recombinant antibody production.

The amino acid sequence of LmPDE polypeptides may be used to select specific regions of a LmPDE protein for generating antibodies. For example, hydrophobicity and hydrophilicity analyses of a LmPDE amino acid sequence may be used to identify hydrophilic regions in a LmPDE protein structure. Regions of a LmPDE polypeptide that show immunogenic structure, as well as other regions and domains, can readily be identified using various other methods known in the art such as Chou-Fasman, Garnier-Robson, Kyte-Doolittle, Eisenberg, Karplus-Schultz or Jameson-Wolf analysis (Rost et al. (1994) *Protein* 19, 55-72).

Methods for preparing a protein for use as an immunogen and for preparing immunogenic conjugates of a protein with a carrier such as BSA, KLH, or other carrier proteins are well known in the art. Techniques for conjugating or joining therapeutic agents to antibodies are well known (Amon et al. (1985) "Monoclonal Antibodies For Immunotargeting Of Drugs In Cancer Therapy", *Monoclonal Antibodies And Cancer Therapy*, Reisfeld et al. (eds.) pp. 243-56, Alan R. Liss, Inc; Hellstrom et al. (1987) "Antibodies For Drug Delivery", *Controlled Drug Delivery* (2nd Ed.), Robinson et al. (eds.) pp. 623-53, Marcel Dekker, Inc.; Thorpe (1985) "Antibody Carriers Of Cytotoxic Agents In Cancer Therapy: A Review", *Monoclonal Antibodies '84-Biological And Clinical Applications*, Pinchera et al. (eds.) pp. 475-506; Thorpe et al. (1982) "The Preparation And Cytotoxic Properties Of Antibody-Toxin Conjugates", *Immunol. Rev.* 62, 119-158; and Sodee et al. (1997), *Clin. Nuc. Med.* 21, 759-766). In some circumstances, for example, direct conjugation using carbodiimide reagents may be used; in other instances linking reagents such as those supplied by Pierce Chemical Co., Rockford, Ill., may be effective.

Administration of a LmPDE immunogen is conducted generally by injection over a suitable time period and with use of a suitable adjuvant, as is generally understood in the art. (Harlow et al. (1988) *Antibodies: A Laboratory Manual*, Cold Spring Harbor Press). During the immunization schedule, titers of antibodies can be taken to determine the adequacy of antibody formation.

While the polyclonal antisera produced in this way may be satisfactory for some applications, monoclonal antibody preparations are preferred for pharmaceutical compositions. Immortalized cell lines which secrete a desired monoclonal antibody may be prepared using the standard method of Kohler and Milstein (*Nature* 256, 495-497) or modifications which effect immortalization of lymphocytes or spleen cells, as is generally known in the art. The immortalized cell lines secreting the desired antibodies are screened by immunoassay in which the antigen is a LmPDE polypeptide. When the appropriate immortalized cell culture secreting the desired antibody is identified, the cells can be cultured either in vitro or by production in ascites fluid. The desired monoclonal antibodies are then recovered from the culture supernatant or from the ascites supernatant.

The antibodies or fragments may also be produced by recombinant means. The antibody regions that bind specifically to the desired regions of a LmPDE polypeptide can also be produced in the context of chimeric antibodies of multiple species origin.

The antibodies of the invention can bind specifically to LmPDE polypeptides. In one embodiment, the LmPDE antibodies may specifically bind to the GAF domain of a LmPDE protein. In another embodiment, the antibodies of the invention may specifically bind to the C-terminal domain of a LmPDE protein. In a further embodiment, the antibodies may specifically bind to the PDE catalytic domain of a LmPDE polypeptide. In other embodiments, the antibodies of this invention may bind to other domains of a LmPDE polypeptide, for example the antibodies may bind to the N-terminal domain of a LmPDE polypeptide.

Use of Antibodies Against LmPDEs

LmPDE polypeptides can be used to elicit the generation of antibodies, including fragments, that specifically bind an epitope associated with a LmPDE polypeptide, using methods described herein (Kohler et al. supra). The antibodies which are immunoreactive with selected domains or regions of a LmPDE polypeptide are particularly useful. In one embodiment, LmPDE antibodies are used to screen expression libraries in order to obtain polypeptides related to LmPDE polypeptides (e.g., homologues).

In another embodiment, LmPDE antibodies are used to enrich or purify LmPDE polypeptides from a sample having a heterologous population of polypeptides. The enrichment and purifying methods include conventional techniques, such as immuno-affinity methods. In general, the immuno-affinity methods include the following steps: preparing an affinity matrix by linking a solid support matrix with a LmPDE antibody, wherein the linked affinity matrix specifically binds with a LmPDE polypeptide; contacting the linked affinity matrix with the sample under conditions that permit a LmPDE polypeptide in the sample to bind to the linked affinity matrix; removing the non-LmPDE polypeptides that did not bind to the linked affinity matrix, thereby enriching for or purifying a LmPDE polypeptide. A further step may include eluting a LmPDE polypeptide from the affinity matrix. The general steps and conditions for affinity enrichment for a desired protein or protein complex can be found in *Antibodies: A Laboratory Manual* (Harlow et al. (1988) CSHL, Cold Spring, N.Y.).

Furthermore, there are multiple diagnostic uses of the antibodies of the invention. The invention provides methods for diagnosing in a subject, e.g., an animal or human subject, a disease associated with the presence or deficiency of at least one LmPDE polypeptide. In one embodiment, the method comprises quantitatively determining the amount of at least one LmPDE polypeptide in the sample (e.g., cell or biological fluid sample) using any one or a combination of the antibodies of the invention. The amount so determined can then be compared with the amount in a sample from a normal subject. The presence of a measurably different amount in the sample (i.e., the amount of a LmPDE polypeptide in the test sample exceeds or is reduced from the amount of a LmPDE polypeptide in a normal sample) indicates the presence of the disease.

The anti-LmPDE antibodies of the invention may also be useful in diagnostic imaging methodologies, where the antibodies have a detectable label. The invention provides various immunological assays useful for the detection of LmPDE polypeptides in a suitable biological sample. Suitable detectable markers include, but are not limited to, a radioisotope, a fluorescent compound, a bioluminescent compound, a chemiluminescent compound, a chromophore, a metal chelator, biotin, or an enzyme. Such assays generally comprise one or more labeled LmPDE antibodies that recognize and bind a LmPDE polypeptide, and include various immunological assay formats well known in the art, including but not limited to various types of precipitation, agglutination, complement fixation, radioimmunoassays (RIA), enzyme-linked immunosorbent assays (ELISA), enzyme-linked immunofluorescent assays (ELIFA) (H. Liu et al. (1998) *Cancer Research* 58, 4055-4060), immunohistochemical analyses, and the like.

Methods for Generating LmPDE Polypeptides

The LmPDE polypeptides of the present invention may be generated by chemical synthesis or by recombinant methods. If a high yield is desired, recombinant methods may be used, as set forth above. The LmPDE polypeptides of the invention can also be generated by chemical synthetic methods. The principles of solid phase chemical synthesis of polypeptides are well known in the art and may be found in general texts relating to this area (see, e.g., Dugas et al. (1981) *Bioorganic Chemistry*, pp. 54-92, Springer-Verlag, New York).

The present invention also provides derivative polypeptide molecules, such as chemically modified LmPDE polypeptides. Illustrative of such modifications is replacement of hydrogen by an alkyl, acyl, or amino group. The LmPDE polypeptide derivatives retain the biological activities of naturally occurring LmPDEs.

Screening for Compounds that Modulate LmPDE Activity/Expression

The LmPDE polypeptides of the present invention are phosphodiesterases from *Leishmania*, such as *Leishmania major*, that function as key components in the regulation of intracellular levels of cAMP by catalyzing its hydrolysis. Together with the adenylyl cyclases, these phosphodiesterases ultimately control the biological responses mediated by the messenger cAMP. Regulation of intracellular levels of cAMP is crucial in the processes of cell transformation and proliferation. Thus, LmPDE polypeptides are important targets for compounds that modulate their biological activity, or that modulate their expression. Compounds that effectively modulate the biological functions of LmPDEs may serve as important therapeutics for the treatment of parasitic diseases such as leishmaniasis. The invention also provides a method for obtaining compounds that modulate either the activity or the expression of LmPDEs.

The present invention relates to screening methods for identifying compounds that bind to LmPDE polypeptides (e.g., ligands) and modulate the biological activity of LmPDE polypeptides. These screening methods may also identify compounds that do not necessarily bind directly to LmPDEs, but nevertheless modulate LmPDE activity. Such screening methods can also be used to identify compounds that modulate the expression of LmPDE polypeptides.

Typically, the goal of screening methods is to identify compounds that bind to the target LmPDEs and cause changes in the biological activity of the target polypeptide or nucleic acid molecule. The compounds of interest are identified from a population of candidate compounds. For example, a compound that effectively binds the target nucleic acid molecule can decrease expression of the LmPDE polypeptide, and thereby decrease proliferation of cells that express LmPDE polypeptides. Decreasing the proliferation of cells that express LmPDE polypeptides can be an effective method of treating diseases associated with the infection of parasites such as *Leishmania major*.

Several assays and screens can be used to identify compounds that modulate LmPDE activity and/or expression. The compounds identified in the assays and screens may modulate the activity of LmPDEs in a variety of ways. For example, the compounds may bind directly to a LmPDE polypeptide or it may bind to intracellular proteins that bind to a LmPDE. The compounds may also modulate the activity of a LmPDE gene, or modulate the expression of a LmPDE gene or a LmPDE polypeptide. For example, such compounds may bind to a LmPDE regulatory sequence and thus modulate gene expression (see, e.g. Platt (1994) *J. Biol. Chem.* 269, 28558-28562).

Compounds that can be screened by the methods described in the present invention include, but are not limited to, peptides and derivatives thereof (e.g. peptidomimetics) that bind to a LmPDE polypeptide or otherwise modulate its activity in any way. Such compounds may include peptides, such as soluble peptides, including members of random peptide libraries (Lam et al. (1991) *Nature* 354, 82-84; Houghten et al. (1991) *Nature* 354, 84-86), and combinatorial chemistry-derived molecular libraries made of D- and/or L-amino acids, phosphopeptides (including, but not limited to, members of random or partially degenerate, directed phosphopeptide libraries; see, e.g., Songyang et al. (1993) *Cell* 72, 767-778), carbohydrates, and small organic or inorganic molecules.

Compounds that can be screened include, but are not limited to, natural and synthetic products. A skilled artisan can readily recognize that there is no limit as to the structural nature of the compounds tested for binding to LmPDE polypeptides.

Candidate compounds that are tested for binding with LmPDE polypeptides and/or modulating the activity of LmPDE polypeptides can be randomly selected or rationally selected. As used herein, a compound is said to be randomly selected when the compound is chosen randomly without considering the specific sequences of the LmPDE polypeptide or nucleic acid. Examples of randomly selected agents are members of a chemical library, a peptide combinatorial library, a growth broth of an organism, or plant extract.

As used herein, a compound is said to be rationally selected when the compound is chosen on a nonrandom basis that is based on the sequence of the target site and/or its conformation in connection with the compound's action. Compounds can be rationally selected by utilizing the peptide sequences that make up the LmPDE polypeptide or by analyzing the nucleotide sequence that encodes a LmPDE polypeptide.

Methods for rationally selecting a compound that modulates the activity and/or expression of a LmPDE polypeptide include computer modeling or searching techniques. For example, compounds likely to interact with the active site of a LmPDE polypeptide are identified. The active site of a LmPDE polypeptide can be identified using methods known in the art including, for example, analysis of the amino acid sequence of a molecule, and from a study of complexes formed by a LmPDE polypeptide and a native substrate (e.g. cAMP), Methods such as X-ray crystallography and NMR can be used to solve the three-dimensional structure of a protein in order to identify possible binding sites, including the active site of the natural substrate.

Computer-based modeling can be used to complete an incomplete or insufficiently accurate structure. Modeling methods that can be used are, for example, parameterized models specific to particular biopolymers such as proteins or nucleic acids, molecular dynamics modeling based on computing molecular motions, statistical mechanics models based on thermal ensembles, or combined models. For most types of models, standard molecular force fields, representing the forces between constituent atoms and groups are necessary, and can be selected from force fields known in the art. Information on incomplete or less accurate structures determined as above can be incorporated as constraints on the structures computed by these modeling methods.

Once the structure of the active site of a LmPDE polypeptide has been determined, candidate modulating compounds can be identified by searching databases containing compounds along with information on their molecular structure. The compounds identified in such a search are those that have structures that match the active site structure, fit into the active site, or interact with groups defining the active site. The compounds identified by the search are potential LmPDE modulating compounds.

These methods may be used to identify improved modulating compounds based on compounds that are known to modulate other PDEs. The structure of the known compound is modified and modulating effects are determined using experimental and computational methods as described herein. The altered structure is compared to the active site structure of a LmPDE polypeptide to determine or predict how a particular modification to the compound will effect its interaction with that protein. Systematic variations in composition, such as by varying side groups, can be evaluated to obtain modified modulating compounds of preferred specificity or activity.

Examples of molecular modeling systems are the QUANTA programs, e.g., CHARMm, MCSS/HOOK, and X-LIGAND (Molecular Simulations, Inc., San Diego, Calif.). QUANTA provides a modeling environment for simulation and analysis of macromolecules and small organic molecules.

The process of using experimental or predicted structural information in a computer simulation to predict the interactions of potential modulating compounds is well known in the art. For example, see Rotivinen et al. (1988) *Acta Pharm. Fenn.* 97, 159-166; and McKinaly et al. (1989) *Ann. Rev. Pharmacol. Toxicol.* 29, 111-122. Computer programs designed to screen and depict chemicals are available from companies such as MSI, Allelix, Inc., and Hypercube, Inc. These applications are largely designed for drugs specific to particular proteins; however, they may be adapted to the design of drugs specific to identified regions of DNA or RNA. Commercial sources of chemical libraries can be used as sources of candidate compounds. Such chemical libraries can be obtained from, for example, ArQule, Inc.

Compounds that modulate the activity and/or expression of a LmPDE polypeptide may also be based on antisense constructs. Therapeutic techniques based on an antisense approach involve the design of oligonucleotides that are complementary to LmPDE mRNAs. These oligonucleotides bind the complementary transcripts and prevent translation. Absolute (or total) complementarity is not required. An oligonucleotide may function as an effective antisense construct as long as its sequence is sufficiently complementary to be able to hybridize with RNA and form a stable duplex. In the case of a double-stranded antisense nucleic acid molecule, a single strand of the duplex may be tested, or triplex formation may be assayed. The ability to hybridize will depend on both the degree of complementarity and the length of the antisense nucleic acid. In general, the longer the hybridizing nucleic acid, the more base mismatches with an RNA it may contain and still form a stable duplex (or triplex, as the case may be). One skilled in the art can determine a tolerable degree of mismatch by use of standard procedures to determine the melting point of the hybridized complex.

Furthermore, several in vitro assays can be used to identify compounds that modulate the expression and/or the activity of a LmPDE polypeptide. Such assays typically involve preparation of a reaction mixture comprising a LmPDE polypeptide and a test compound under conditions sufficient to allow the two components to interact and bind, thus forming a complex that can be detected and/or isolated. The binding of a compound with a LmPDE polypeptide can be assayed using a shift in the molecular weight or a change in biological activity of the unbound LmPDE polypeptide, or the expression of a reporter gene in a yeast two-hybrid system (Fields et al. (1989) *Nature* 340, 245-246). The method used to identify whether a compound binds to a LmPDE polypeptide will be based primarily on the nature of the LmPDE polypeptide used. For example, a gel retardation assay can be used to determine whether a compound binds to a LmPDE polypeptide. Alternatively, immunodetection and biochip (e.g., U.S. Pat. No. 4,777,019) technologies can be adopted for use with a LmPDE polypeptide. An alternative method for identifying compounds that bind with a LmPDE polypeptide employs TLC overlay assays using glycolipid extracts from immune-type cells (Abdullah et al. (1992) *Infect. Immunol.* 60, 56-62). Furthermore, a decrease in LmPDE cAMP hydrolytic activity can be measured to determine whether or not a particular compound is inhibiting a LmPDE. A skilled artisan can readily employ numerous techniques known in the art for determining whether a particular compound binds to a LmPDE polypeptide of the invention. Such assays will typically make use of a control cell.

It is also possible to use cell-based assays to identify compounds that interact with LmPDE polypeptides. Cell lines that naturally express LmPDEs or that have been genetically engineered to express LmPDEs can be used. For example, test compounds may be added to cell cultures after which the hydrolysis of cAMP can be measured using standard techniques known in the art. A decrease in the amount of hydrolysis in the presence of a test compound compared to control cells that do not contain the test compound indicates that the test compound is an inhibitor of LmPDE activity.

Inhibitors of LmPDE expression may be identified by using a chimeric gene in which a LmPDE nucleotide sequence is fused with a reporter, such as firefly luciferase. Cultured cells that have been transformed with the chimeric gene can be screened for the expression of luciferase activity in the presence of test compounds. Compounds that inhibit luciferase activity in this high throughput assay can also be confirmed by direct measurement for the presence of the endogenous LmPDE polypeptide (e.g. by Western blotting) and LmPDE mRNA (e.g. by Northern blotting) using methods that are well known in the art (see, e.g., Ausubel et al. (1994) *Current Protocols in Molecular Biology*, John Wiley & Sons). Candidate compounds can be further tested in cell or tissue cultures as well as in animal models. Cells expressing a LmPDE polypeptide, for example, can be incubated with a test compound, after which cell lysates are prepared and probed for the presence of the LmPDE polypeptide (e.g. using Western blotting techniques). A decrease in the amount of LmPDE expression in cultures treated with the test compound compared to control cultures without the test compound indicates that the test compound is an inhibitor of LmPDE expression.

In vivo assays can also be used to test these compounds in animal models of *Leishmania* infection. Test compounds predicted to inhibit LmPDE activity and/or expression are administered to the animals. The treated animals can then be assayed for inhibition of LmPDE activity. Such assays may be indirect or inferential. Improved health, for example, may indicate the efficacy of a test compound. Direct assays may also be performed where a decrease in LmPDE expression can be measured by a Northern blotting analysis. A decrease in the amount of LmPDE mRNA present in the sample from treated animals compared to untreated control animals indicates that the test compound inhibits LmPDE expression. A direct assay may also be performed that measures the hydrolytic activity of a LmPDE on cAMP. A decrease in hydrolysis of cAMP in the sample from treated animals compared to the untreated control animals indicates that the test compound inhibits LmPDE activity.

LmPDE polypeptides which are used in the screening assays described herein include, but are not limited to, an isolated LmPDE polypeptide, a host cell that expresses a LmPDE polypeptide, or a fraction of a host cell that expresses a LmPDE polypeptide.

The cellular extracts to be tested for binding with LmPDE polypeptides and or modulating the activity of LmPDE polypeptides can be, as examples, aqueous extracts of cells or tissues, organic extracts of cells or tissues or partially purified cellular fractions. A skilled artisan can readily recognize that there is no limit as to the source of the cellular extracts used in the screening methods of the present invention.

Compounds that are identified as candidates for inhibiting the activity and/or expression of a LmPDE polypeptide, when administered in a therapeutically effective amount, may be useful for treating diseases and reducing symptoms associated with the infection of *Leishmania*, such as leishmaniasis. Toxicity and therapeutic efficacy of identified compounds that modulate the activity and/or expression of a LmPDE polypeptide can be determined by standard pharmaceutical procedures. For example, using either cells in culture or experimental animals, the dose lethal to 50% of the population ($LD_{50}$) can be determined. The dose ratio between toxic and therapeutic effects is the therapeutic index and can be expressed as the ratio $LD_{50}/ED_{50}$. Compounds with a large therapeutic index are preferred. While compounds that have toxic side effects may be used, care should be taken to design a delivery system that targets such compounds to the site of affected tissue to minimize potential damage to uninfected cells and thus reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administrations used. For any compound used in the method of the present invention, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma can be measured, for example, by high performance liquid chromatography.

Generation of Transgenic Organisms

Another aspect of the invention provides transgenic organisms comprising LmPDE nucleic acids. As used herein, a genetically modified organism refers to an organism that has been altered from its natural state by manipulation of the native nucleic acid sequences. For example, in one application, PDE-deficient organisms can be generated using standard knock-out procedures to inactivate an endogenous PDE. Alternatively, inducible PDE anti-sense molecules can be used to regulate the activity and/or expression of the endogenous PDE. An organism can also be produced so as to contain a LmPDE-encoding nucleic acid molecule or an anti-sense-LmPDE expression unit that directs the expression of a LmPDE polypeptide or the antisense molecule. In such cases, an organism is generated in which the expression of the endogenous PDE gene is altered by inactivation and/or replaced by a LmPDE gene. This can be accomplished using a variety of procedures known in the art such as targeted recombination. Once generated, the endogenous PDE-deficient organism that expresses a LmPDE polypeptide can be used to (1) identify biological and pathological processes mediated by LmPDE polypeptides, (2) identify proteins and other genes that interact with LmPDE polypeptides, (3) identify compounds that can be exogenously supplied to inhibit a LmPDE polypeptide, and (4) serve as an appropriate screen for identifying mutations within LmPDE genes that increase or decrease activity.

For example, in one embodiment, the endogenous PDE genes in *S. cerevisiae* can be deleted, which results in intracellular accumulation of cAMP. Organisms that accumulate high levels of intracellular cAMP cease to grow when exposed to a heat shock. LmPDE nucleic acid molecules can then be cloned into a yeast expression vector and transfected into the PDE-deficient strain of *S. cerevisiae*. Restoration of heat-insensitive growth is thus a marker for LmPDE activity. Observing whether or not heat-insensitive growth is restored to the transfected strain under various conditions can indicate the effects these conditions have on LmPDE activity.

Uses of LmPDE Polypeptides

As discussed previously, the present invention provides cAMP-specific PDEs from *Leishmania*, such as *Leishmania major*, including LmPDE-A, LmPDE-B1, and LmPDE-B2 and fragments, variants, and mutants thereof. It is known that cAMP plays a key role in cell growth and differentiation in this parasite and that PDEs are responsible for the hydrolysis of this messenger. Therefore, as discussed above, LmPDEs are targets for drug screening assays and are useful in accomplishing selective drug design.

Additionally, the invention provides methods for monitoring the course of disease or disorders associated with the presence of LmPDEs in a test subject by measuring the amount of a LmPDE polypeptide in a sample from the test subject at various points in time. This is done for purposes of determining a change in the amount of a LmPDE in the sample over time. Monitoring the course of a disease or disorder over time may optimize the timing, dosage, and type of treatment. In one embodiment, the method comprises quantitatively determining in a first sample from the subject the presence of a LmPDE polypeptide and comparing the amount so determined with the amount present in a second sample from the same subject taken at a different point in time, a difference in the amounts determined being indicative of the course of the disease. Measuring the amount of LmPDE polypeptide present in a sample can be performed using a variety of techniques well known in the art, for example by using immunoassays as discussed below.

The present invention further provides methods for using isolated and substantially purified LmPDE polypeptides as antigens for the production of novel anti-LmPDE antibodies, and for using LmPDE polypeptides for obtaining and detecting novel LmPDE ligands. The anti-LmPDE antibodies are useful in diagnostic assays and kits for the detection of naturally occurring LmPDE protein sequences present in biological samples.

Uses of Nucleic Acid Molecules Encoding LmPDEs

The nucleic acid molecules encoding LmPDE polypeptides of the invention are useful for a variety of purposes, including their use in diagnosis and/or prognostic methods. The nucleic acid molecules and polypeptides of the invention may be used to test for the presence and/or amount of LmPDE nucleotide sequences and LmPDE polypeptides in a suitable biological sample.

The nucleic acid molecules of this invention can be used in various hybridization methods to identify and/or isolate nucleotide sequences related to LmPDE nucleotide sequences, such as different polymorphic forms and genomic sequences. Sequences related to a LmPDE nucleotide sequence are useful for developing additional ligands and antibodies. The hybridization methods are used to identify/isolate DNA and RNA sequences that are at least about 60%, 65%, 70%, 75%, 80%, 85%, 90%, 95%, 96%, 97%, 98%, or 99% identical to LmPDE nucleotide sequences, such as novel LmPDE homologues, allelic variants, and mutant forms.

Nucleotide sequences that encode LmPDE polypeptides described herein can be used as nucleic acid probes to retrieve nucleic acid molecules having sequences related to LmPDEs.

In one embodiment, a LmPDE nucleic acid probe is used to screen genomic libraries, such as libraries constructed in lambda phage or BACs (bacterial artificial chromosomes) or YACs (yeast artificial chromosomes), to isolate a genomic clone of a LmPDE gene. The LmPDE nucleotide sequences from genomic libraries are useful for isolating upstream or downstream non-coding sequences, such as promoter, enhancer, and transcription termination sequences. The upstream sequences from a LmPDE gene may be joined to non-LmPDE sequences in order to construct a recombinant DNA molecule that expresses the non-LmPDE sequence upon introduction into an appropriate host cell. In another embodiment, a LmPDE probe is used to screen cDNA libraries to isolate cDNA clones expressed in certain tissues or cell types.

Additionally, pairs of oligonucleotide primers can be prepared for use in a polymerase chain reaction (PCR) to selectively amplify or clone nucleic acid molecules encoding LmPDE proteins, or fragments thereof. PCR methods (U.S. Pat. No. 4,965,188) that include numerous cycles of denature/anneal/polymerize steps are well known in the art and can be readily adapted for use in isolating LmPDE-encoding nucleic acid molecules.

In addition, the nucleic acid molecules of the invention may also be employed in diagnostic embodiments, using LmPDE nucleic acid probes to determine the presence and/or the amount of LmPDE sequences present in a biological sample. One embodiment encompasses determining the amount of LmPDE nucleotide sequences present within the suitable biological sample such as in specific cell types, tissues, or body fluids, using a LmPDE probe in a hybridization procedure. The amount of LmPDE nucleic acid molecules in the test sample can be compared with the amount of LmPDE nucleic acid molecules in a reference sample from a normal subject. The presence of a measurably different amount of LmPDE nucleic acid molecules between the test and reference samples may correlate with the presence or with the severity of a disease associated with abnormal levels (high or low) of LmPDE nucleic acid molecules as compared to normal levels.

In another embodiment, monitoring the amount of LmPDE RNA transcripts over time is effected by quantitatively determining the amount of LmPDE RNA transcripts in test samples taken at different points in time. A difference in the amounts of LmPDE RNA transcripts in the various samples is indicative of the course of the disease associated with expression of a LmPDE transcript.

To conduct such diagnostic methods, a suitable biological sample from a test subject is contacted with a labeled LmPDE probe, under conditions effective to allow hybridization between the sample nucleic acid molecules and the probe. In a similar manner, a biological sample from a normal subject is contacted with a LmPDE probe and hybridized under similar conditions. The presence of the nucleic acid molecules hybridized to the probe is detected. The relative and/or quantified amount of the hybridized molecules may be compared between the test and reference samples. The LmPDE probes can be labeled with any of several known detectable labels, including radioactive, enzymatic, fluorescent, or chemiluminescent labels.

Many suitable variations of hybridization technology are available for use in the detection of nucleic acids that encode LmPDE polypeptides. These include, for example, Southern and Northern procedures. Other hybridization techniques and systems are known that can be used in connection with the detection aspects of the invention, including diagnostic assays such as those described in Falkow et al. (U.S. Pat. No. 4,358,535). Another hybridization procedure includes in situ hybridization, where the target nucleic acids are located within one or more cells and are contacted with the LmPDE probes. As is well known in the art, the cells are prepared for hybridization by fixation, e.g. chemical fixation, and placed in conditions that permit hybridization of a LmPDE probe with nucleic acids located within the fixed cell.

The nucleic acid molecules of this invention further provide anti sense molecules that recognize and hybridize to a LmPDE nucleic acid. Antisense polynucleotides are particularly useful in regulating the expression of a LmPDE protein in those cells expressing a LmPDE mRNA. One embodiment useful for this approach is an anti-sense molecule corresponding to the N-terminal sequence of the gene. The present invention includes such full length and fragment anti-sense polynucleotides.

The polynucleotides of this invention further provide reagents to develop animal models using "knock-out" strategies through homologous recombination. Methods for generating knock-out animals that fail to express a functional protein molecule are well known in the art (Capecchi (1989) *Science* 244, 1288-1292), and may be used in studying the in vivo functions of LmPDEs.

It is to be understood that both the foregoing general description and the following examples are exemplary and explanatory only and are not restrictive of the invention, as claimed. Moreover, it must be understood that the invention is not limited to the particular embodiments described. Further, the terminology used to describe particular embodiments is not intended to be limiting, since the scope of the present invention will be limited only by its claims.

The following examples are presented to illustrate the present invention and to assist one of ordinary skill in making and using the same. The methodology and results may vary depending on the intended goal of treatment and the procedures employed. The examples are not intended in any way to otherwise limit the scope of the invention.

EXAMPLES

Example 1

The following example provides the methods used to identify three cyclic nucleotide-specific phosphodiesterases from *Leishmania major*.

Two families of cAMP-specific PDEs from the protozoal parasite *Trypanosoma brucei* had been previously characterized and identified (Zoraghi et al. (2001) *J. Biol. Chem.* 276, 11559-11566; Zoraghi et al. (2002) *Proc. Natl. Acad. Sci. USA* 99, 4343-4348; Gong et al. (2001) *Mol. Biochem. Parasitol.* 116, 229-232); and Rascon et al. (2002) *Proc. Natl. Acad. Sci. U.S.A.* 99, 4714-4719. Sequences representing each family were then used to screen the *Leishmania* genome database available on the Sanger Institute's GeneDB website. A BLAST search was performed using the nucleotide sequence corresponding to the trypanosomal enzyme TbPDE1, which identified a nucleotide sequence in *Leishmania major* that shares 45.1% amino acid sequence identity (determined using the BESTFIT utility of the GCG program suite with default parameters). This novel sequence was labeled LmPDE-A. The gene for LmPDE-A is located within a sequence cluster consisting of chromosomes 18, 20, and 22. A BLAST search was also performed using the nucleotide sequence corresponding to the trypanosomal enzyme TbPDE2C, which identified two closely related sequences that were subsequently labeled LmPDE-B1 and LmPDE-B2. LmPDE-B1 shares 70.2% amino acid identity with the query sequence TbPDE2C, while LmPDE-B2 shares 69.8% overall sequence identity with TbPDE2C. Overall amino acid sequence identity between LmPDE-B1 and LmPDE-B2 is 84.5%. According to the *Leishmania* genome database, the identified LmPDE-B1 and LmPDE-B2 loci are located on chromosome 15.

Example 2

The following example provides the methods used to clone and sequence the novel sequences identified in the *Leishmania* genome database.

Based on the sequences identified in the *Leishmania* genome database (as discussed in Example 1), PCR-primers were designed to amplify all three full-length genes from the genomic DNA of *Leishmania major*. PCR primers were also designed to amplify only the open reading frame portion of the three full-length genes. The primers were designed to contain a SalI site for in-frame cloning into the pLT1 vector (where the ATG-initiation codon is provided by the vector) and to code for a C-terminal hemagglutinin tag. For LmPDE-A, the forward and reverse primers were designed as follows: forward—5'-gtggtcgactcgactttcttgagcag-3' (nucleotides 4-21 of the open reading frame, which correspond to nucleotides 533-550 in FIG. 2); reverse—5'-ptgggaatcctaagcataatctggaa-catcatatggatacgagtcgtcgtggttgg-3' (nucleotides 1896-1877 of the open reading frame—which correspond to nucleotides 2425-2406 in FIG. 2—and HA-tag). For LmPDE-B1, the forward and reverse primers were designed as follows: forward—5'-gatgtcga ctggcatatttcacggcca-3' (nucleotides 2-19 of the open reading frame, which correspond to nucleotides 1268-1286 in FIG. 4); reverse—5'-ctgggaatccta agcataatctg-gaacatcatatggataaacaatcgagggtcggatg-3' (nucleotides 2792-2772 of the open reading frame—which correspond to nucleotides 4058-4038 in FIG. 4—and HA-tag). For LmPDE-B2 the forward and reverse primers were designed as follows: forward—5'-gatgtcgacattcagcggtcttttcc-3' (nucleotides 3-21 of the open reading frame, which correspond to nucleotides 2184-2202 in FIG. 6); reverse—5'-ctgggaatcctaagcataatctg-gaacatcatatggat aaacaatcgaggatcggatg-3' (nucleotides 2822-2803 of the open reading frame—which correspond to nucleotides 5003-4984 in FIG. 6—and HA tag). The genes of *Leishmania major*, as with other kinetoplastids, do not contain introns. Accordingly, amplification of open reading frames directly from genomic DNA is routinely performed (Beverley (2003) *Nat. Rev. Genet.* 4, 11-19). Both strands of all three PCR fragments (LmPDE-A, LmPDE-B1, and LmPDE-B2) were then cloned via the TA-overhang into the vector pCR2.1-TOPO following the instructions of the kit supplied by Invitrogen. The clones were then sequenced using the ABI PRISM Big Dye Terminator v3.0 Cycle Sequencing Ready Reaction Kit (Applied Biosystems). Both strands of each clone were sequenced at least two times for verification.

The full-length LmPDE-A nucleotide sequence, with a length of 10,966 nucleotides, is shown in FIG. 2 where the open reading frame begins with adenine at position 530 and ends with guanine at position 2425. The corresponding amino acid sequence is set forth in FIG. 1. The full-length nucleotide sequence of LmPDE-B1, which is 7,095 nucleotides in length, is shown in FIG. 4, where the open reading frame begins with adenine at position 1267 and ends with adenine at position 4059, and the corresponding amino acid sequence is set forth in FIG. 3. The full-length nucleotide sequence of LmPDE-B2, which is 6,945 nucleotides in length, is shown in FIG. 6, where the open reading frame begins with adenine at position 2182 and ends with adenine at position 5004. The amino acid sequence that corresponds to this sequence is set forth in FIG. 5.

Figure 7B:
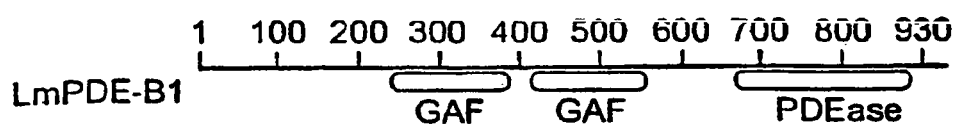
Figure 7C:
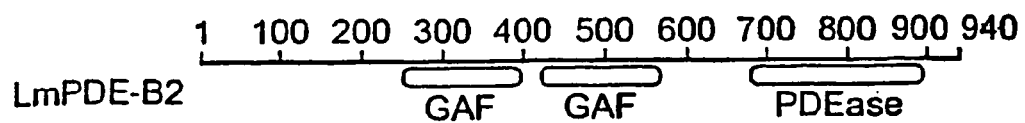

The sequence of the cloned LmPDE-A coincided 100% with the sequence present in the *Leishmania* database. The predicted amino acid sequence of LmPDE-A (FIG. 1) shares 45.1% overall sequence identity with the amino acid sequence of trypanosomal TbPDE1. The predicted amino acid sequence of LmPDE-B1 (FIG. 3) shares 70.2% overall sequence identity with the trypanosomal TbPDE2C amino acid sequence, while the predicted amino acid sequence of LmPDE-B2 (FIG. 5) shares 69.8% overall sequence identity with TbPDE2C. Using the Conserved Domain Search Service provided by the National Center for Biotechnology Information's (NCBI) Conserved Domain Database, several conserved domains were identified in the LmPDE amino acid sequences. As indicated in FIG. 7, LmPDE-A contains a highly conserved catalytic domain (PDEase) beginning with tyrosine at amino acid position 384, and ending with proline at amino acid position 609. LmPDE-B1 and LmPDE-B2 also each contain a highly conserved PDEase domain, beginning with phenylalanine at amino acid position 647, and ending with phenylalanine at amino acid position 880 (LmPDE-B1) and beginning with phenylalanine at amino acid position 657, and ending with phenylalanine at amino acid position 890 (LmPDE-B2). In addition to the PDEase domain, LmPDE-B1 and LmPDE-B2 both have two GAF domains as shown in FIGS. 7B and 7C.

Example 3

The following example describes the methods used to evaluate the genomic organization of LmPDE-B1 and LmPDE-B2.

Figure 9:
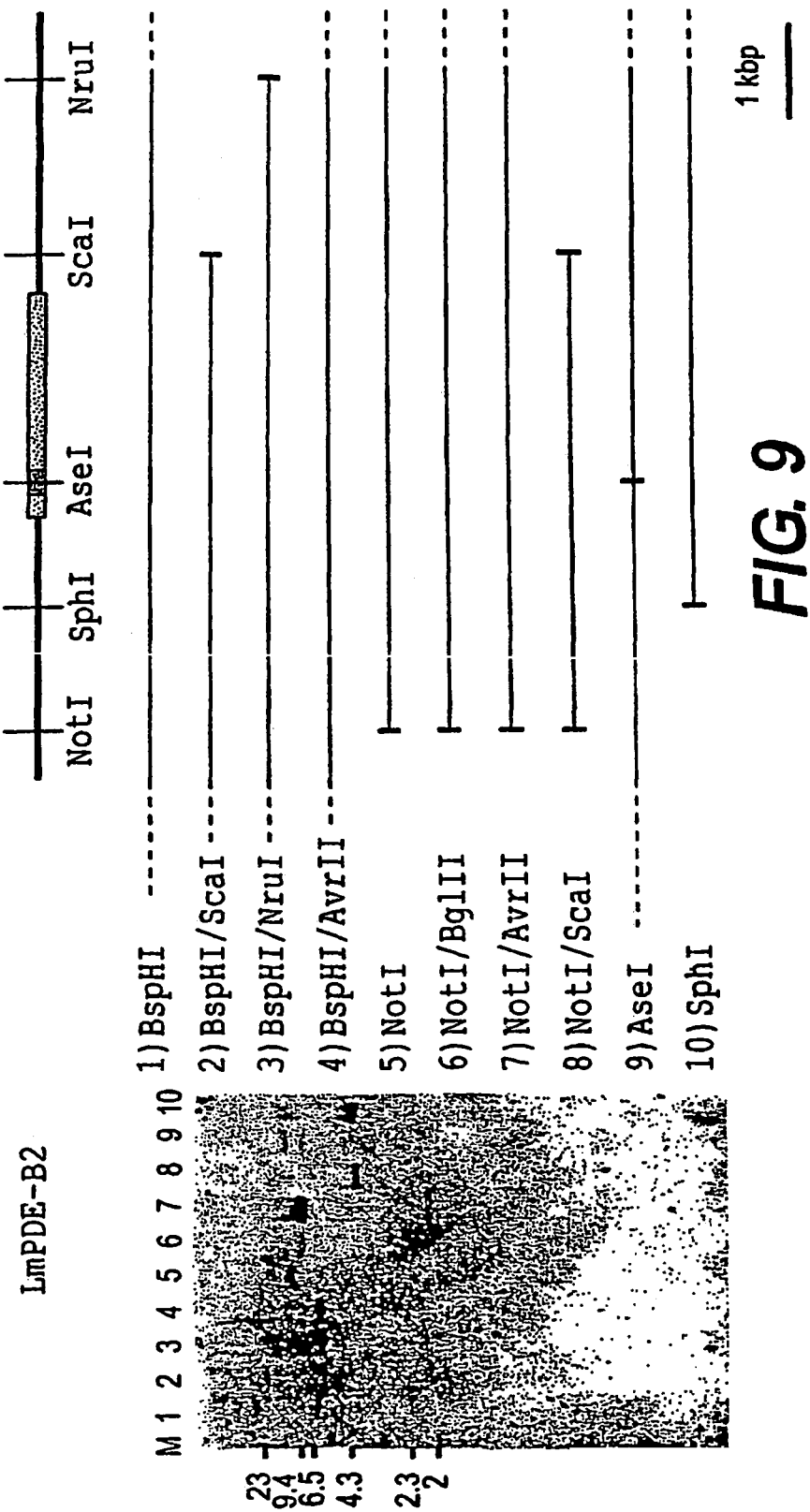
FIG. 9 shows the results of a Southern blot analysis for LmPDE-B2 using a conserved region of the LmPDE-B2 sequence as the hybridization probe.
Figure 11:
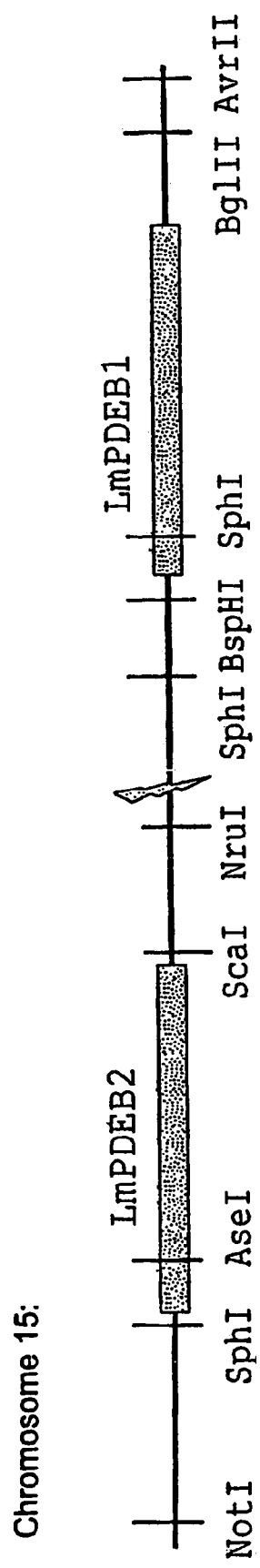
FIG. 11 shows a schematic drawing of the location of the LmPDE-B1 and LmPDE-B2 loci and their approximate relative locations on chromosome 15.

When the nucleotide sequences of the cloned LmPDE-B1 and LmPDE-B2 genes were compared to the sequences present in the *Leishmania* genome database, it was evident that the sequences in the database had been assembled incorrectly. The 3'-untranslated regions of the two genes had inadvertently been swapped. The correct organization of these two genes was then established by Southern blot analysis of a series of restriction digests of *L. major* genomic DNA (as shown in FIGS. 8 and 9). Lane 8 of each hybridization (NotI/ScaI double digest) shall be used as an example for the analytical reasoning. If the sequence assembly in the database were correct, a NotI/ScaI double digest should yield a fragment of at least 8 kb when hybridized with a LmPDE-B2-specific probe (since no ScaI restriction site is present in the immediate 3'-region of LmPDE-B2 gene). In contrast to this prediction, the data show a 4 kb fragment is generated, demonstrating the presence of a ScaI restriction site close to the 3'-end of the LmPDE-B2 gene. All additional digests shown in FIGS. 8 and 9 support, or are compatible with this conclusion. In addition to establishing the genomic organization of the LmPDE-B1 and LmPDE-B2 genes, these experiments demonstrated that each is a single-copy gene. The hybridization probes used in the Southern blotting analysis were as follows: LmPDE-A-specific: nucleotides 462-910 of the open reading frame (corresponding to nucleotides 991-1439 in FIG. 2); LmPDE-B1-specific: nucleotides 96489 of the open reading frame (corresponding to nucleotides 1362-1755 in FIG. 4); LmPDE-B2-specific: 106-417 of the open reading frame (corresponding to 2287-3936 in FIG. 6). This analysis also confirmed that LmPDE-B1 and LmPDE-B2 are tandemly arranged and separated by about 5 kb on chromosome 15 as shown in FIG. 11.

Example 4

The following example provides the methods used to produce a transgenic yeast strain, containing a LmPDE-A and a LmPDE-B1, wherein the endogenous PDE activity was deleted.

The verified open reading frames of LmPDE-A and LmPDE-B1 were cloned into a yeast expression vector (pLT1, S. Kunz, unpublished) and transfected into a *Saccharomyces cerevisiae* strain wherein both endogenous PDE genes had previously been deleted (strain PP5: MATa leu2-3 leu2-112 ura3-52 his3-532 his4 cam pde1::URA3 pde2::HIS3; Colicelli et al. (1993) *Proc. Natl. Acad. Sci. U.S.A.* 90, 11970-11974). The pLT1 expression vector is a 2μ-based yeast vector carrying a LEU2 selector gene. The cloning site is flanked by a strong TEF2 promotor followed by an optimized Kozak box, and by a Cyc1 terminator. PDE-deficient *S. cerevisiae* accumulate intracellular cAMP, which results in a heat-sensitive phenotype. In particular, no growth is observed after a 15 minute heat shock at 55° C. As shown in FIG. 12, both LmPDE-A and LmPDE-B1 fully complemented this phenotype and restored heat-shock insensitive growth. For a heat-shock assay, patches were streaked onto SC-met-ura plates and grown for 2 days at 30° C. The patches were then replicated onto a plate pre-warmed to 55° C. The plate was incubated for an additional 15 min at 55° C., let cool to room temperature and was then incubated for 1-2 days at 30° C. These findings demonstrate that both LmPDE-A and LmPDE-B1 constructs produce active enzymes and that both enzymes are capable of hydrolyzing cAMP. Subsequent experiments demonstrated that LmPDE-B2 also fully complemented the heat-sensitive phenotype and restored heat-shock resistance (Johner et al. (submitted) *J. Biol. Chem.*).

The open reading frames of LmPDE-A, LmPDE-B1 and LmPDE-B2 were cloned independently into a yeast expression vector (pLT1, S. Kunz, unpublished) and transfected into a *Saccharomyces cerevisiae* strain wherein the endogenous PDE genes had previously been deleted (strain PP5: MATa leu2-3 leu2-112 ura3-52 his3-532 his4 cam pde1::URA3 pde2::HIS3; Colicelli et al. (1993) Proc. Natl. Acad. Sci. U.S.A. 90, 11970-11974). These strains were deposited at the American Type Culture Collection (ATCC) on Aug. 25, 2004, and have been assigned numbers PTA-6167, PTA-6246, and PTA-6247, respectively.

Example 5

The following example provides the methods used to characterize the catalytic activities of recombinant LmPDE-A, LmPDE-B1, and LmPDE-B2. The example also provides the methods used to evaluate the sensitivity of recombinant LmPDE-B1 and LmPDE-B2 to commercially available PDE inhibitors.

Example 5.1

Preparation of Yeast Lysates

PP5 yeast cells expressing LmPDE-A, LmPDE-B1, and LmPDE-B2, were lysed as described previously (Zoraghi et al. (2001) *J. Biol. Chem.* 276, 11559-11566). The cells were grown to mid-log to end-log phase in SC-leu medium, collected, resuspended in the original volume of prewarmed YPD medium, and incubated for an additional 3.5 hours at 30° C. to maximize protein expression. The cells were then harvested, washed twice in $H_2O$, pelleted by centrifugation, and stored overnight at −70° C. The cell pellet was thawed on ice and resuspended in ice-cold extraction buffer (50 mM Hepes pH 7.5, 100 mM NaCl, 1× Complete® protease inhibitor cocktail without EDTA (Roche)). Cells were lysed by grinding with glass beads (0.45-0.50 mm) in 2 ml Sarstedt tubes using a FastPrep FP120 cell disrupter (3×45 seconds at setting 4). The lysed cells were centrifuged and glycerol was added to the resulting supernatant to a final concentration of 15% (v/v). Aliquots were snap-frozen in liquid nitrogen and were stored at −70° C.

Example 5.2

Assay of PDE Activity in Yeast Lysates

PDE activity was determined in 50 mM HEPES, pH 7.5, 0.5 mM EDTA, 10 mM $MgCl_2$, and 50 mg/ml BSA in a final assay volume of 100 µl. Each assay contained 50,000 cpm of $^3$H-labeled cAMP, with unlabeled cAMP added to adjust the desired total substrate concentration. Reactions were performed at 30° C. and were linear for at least 60 minutes. The standard reaction time was set to 15 minutes, and the amount of enzyme was always chosen so that no more than 15% of the substrate was hydrolyzed. Inhibitor studies were done at a cAMP concentration of 1 µM. Inhibitors were dissolved in DMSO, but the final DMSO concentration in the assays never exceeded 1%. Control reactions with DMSO alone were always included. Reactions were stopped by the addition of 25 µl of 0.5 N HCl. For the subsequent dephosphorylation of the AMP, the stopped reactions were neutralized with 20 µl of 1 M Tris base, followed by the addition of 10 µl of alkaline phosphatase (Roche Diagnostics; 1 unit/10 µl). The dephosphorylation reactions were incubated for 15 minutes at 37° C. and were then applied to 1 ml columns of QAE-Sephadex A25 in 30 mM ammonium formiate, pH 6.0. The $^3$H-adenosine formed as a reaction product was eluted with 1.6 ml of 30 mM ammonium formiate, pH 6.0 and was collected into 3.5 ml of water-soluble scintillation fluid (Packard Ultima Flo). Assays were performed in triplicate, and data were analyzed using the Graph Pad Prism software package.

Example 5.3

Activity and Specificity of LmPDEs

Lysates prepared from yeast expressing LmPDE-A consistently showed no measurable PDE activity. This observation is consistent with the finding that LmPDE-A is less efficient than LmPDE-B1 and LmPDE-B2 at complementing the PDE deficiency of the host strain PP5. In addition, these findings are very similar to the observations made with the trypanosomal homologue TbPDE1. For example, TbPDE1 complemented the PDE deficiency of PP5 cells but its effect was less than that of other trypanosomal or human PDEs, and no enzymatic activity was detectable in the corresponding yeast cell lysates (Kunz et al. (2004) Eur. J. Biochem. 271, 637-647).

Figure 13A:
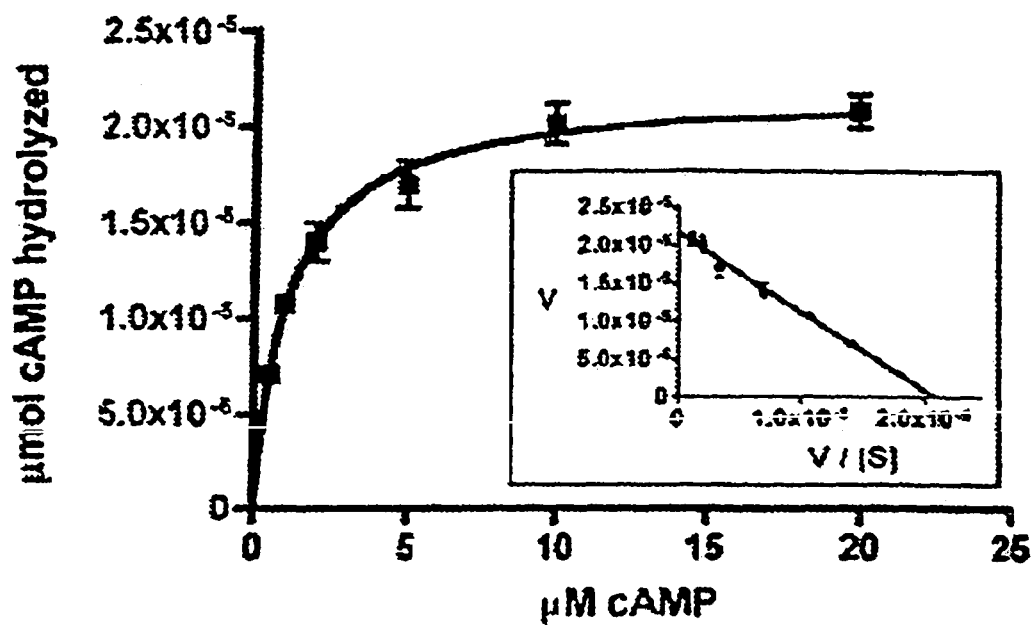
FIGS. 13A, 13B, and 13C show the Michaelis-Menten kinetics of recombinant LmPDE-B1-mediated hydrolysis of cAMP.
Figure 13B:
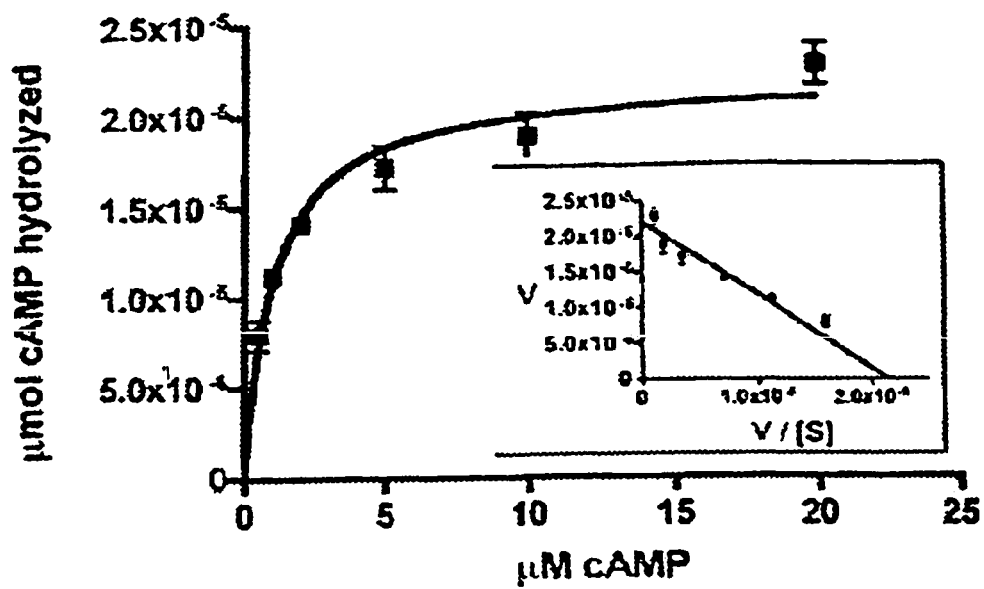
Figure 13C:
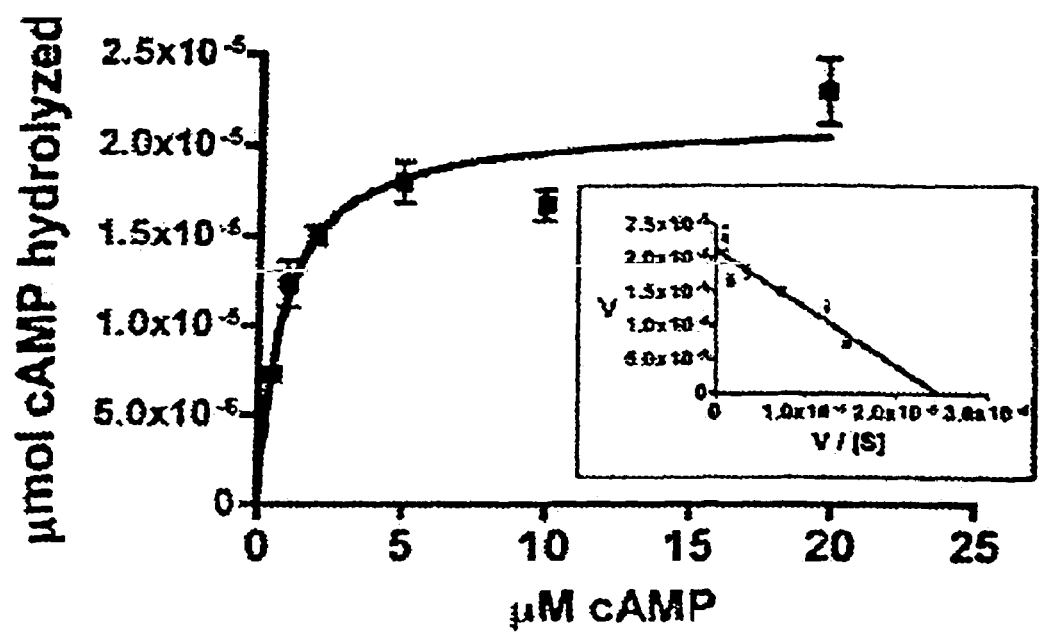
Figure 14A:
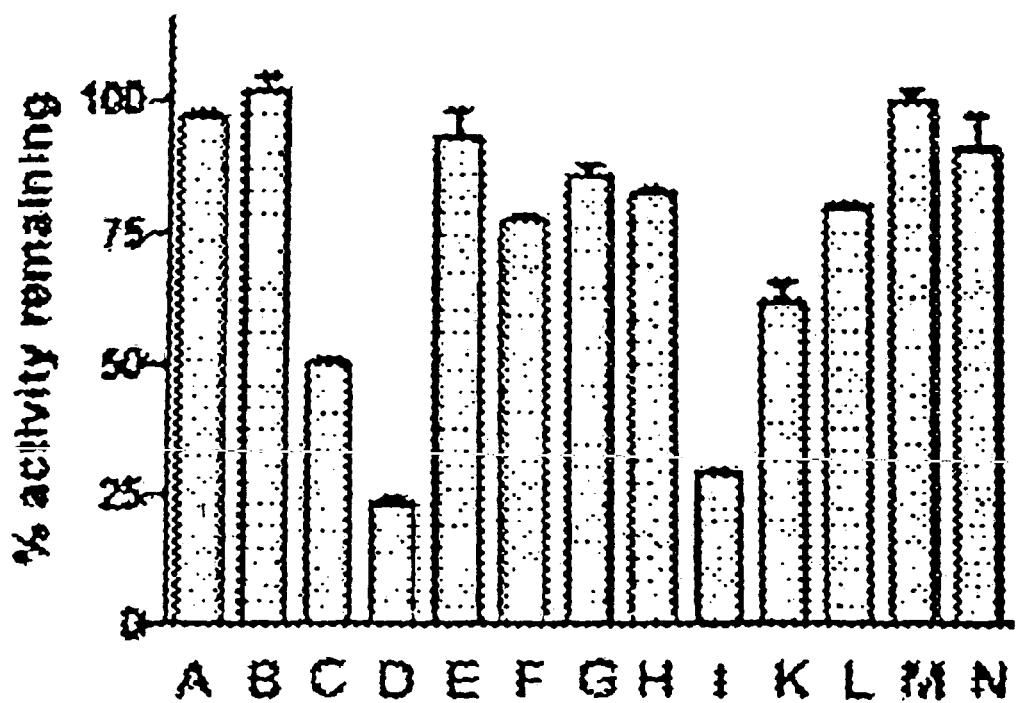
FIGS. 14A and 14B show the effect of various PDE inhibitors on LmPDE-B1 and LmPDE-B2, respectively, in the presence of 1 μM cAMP and 100 μM of cilostamide (A), zaprinast (B), etazolate (C), dipyridamole (D), Ro-20-1724 (E), rolipram (F), isobutylmethylxanthine (IBMX) (G), 8-methoxymethyl-IBMX (H), trequinsin (I), papaverine (K), milrinone (L), petoxifylline (M), and erythro-9-(2-hydroxy-3-nonyl) adenine (EHNA) (N).
Figure 14B:
Figure 14C:
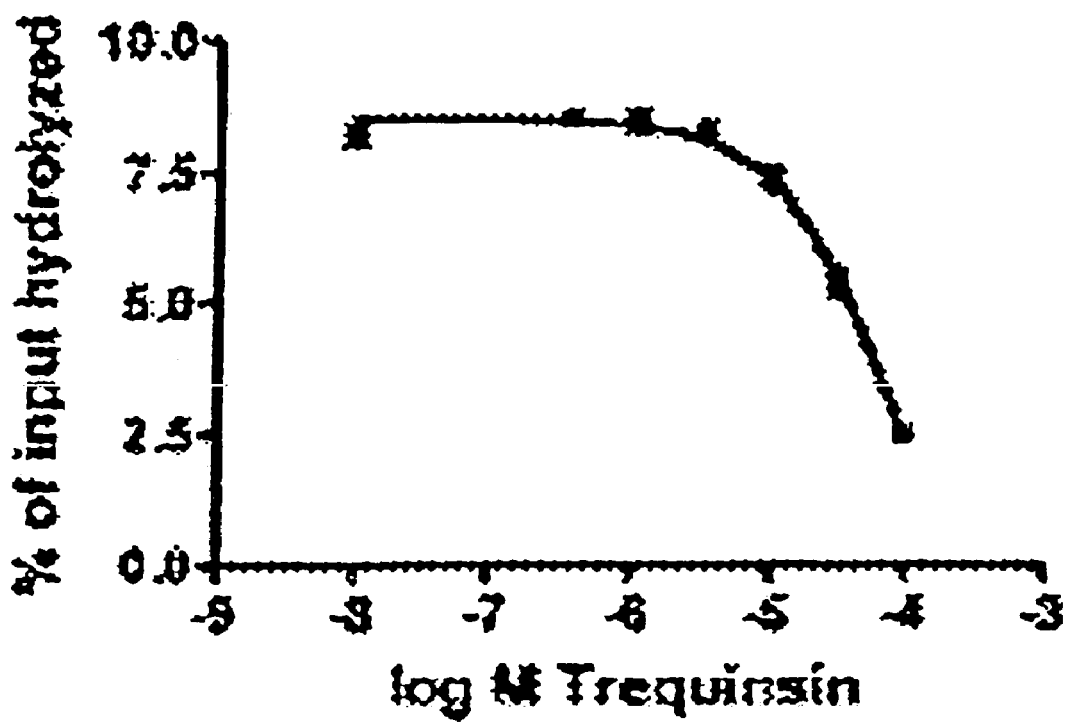
FIGS. 14C and 14D show representative dose-response profiles of trequinsin against LmPDE-B1 and LmPDE-B2, respectively.
Figure 14D:
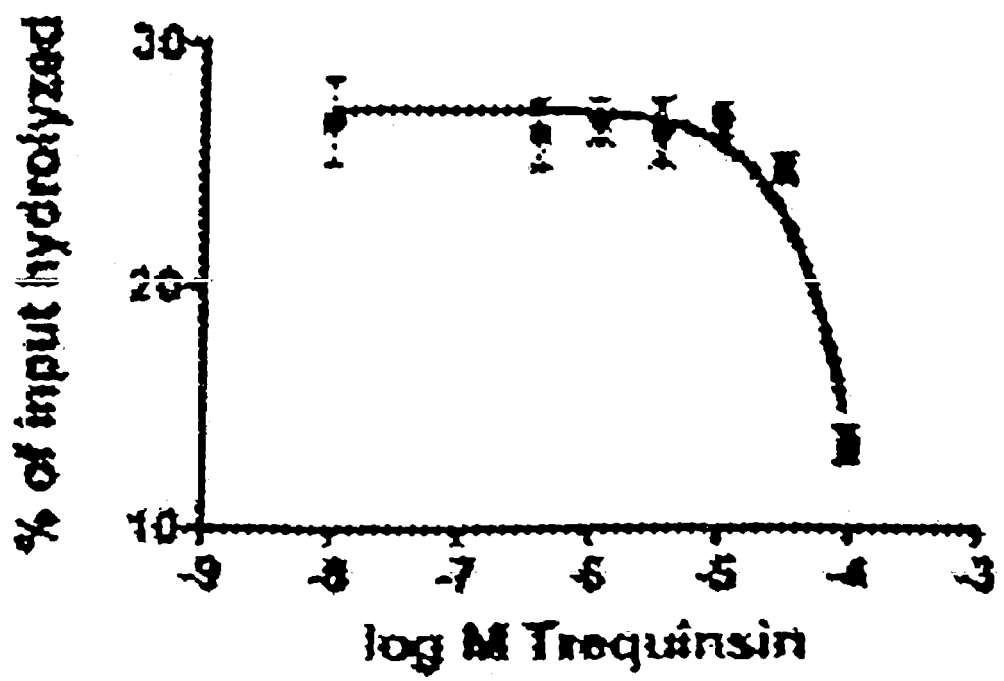

In contrast to lysates from LmPDE-A expressing cells, lysates from yeast strains expressing LmPDE-B1 and LmPDE-B2 showed strong PDE activities. Both enzymes exhibited very similar $K_M$ values for cAMP that were within the range of other class I PDEs (Zoraghi et al. (2001) J. Biol. Chem. 276, 11559-11566; Rascon et al. (2002) Proc. Natl. Acad. Sci. USA 99, 471-44719; Zoraghi et al. (2002) Proc. Natl. Acad. Sci. USA 99, 4343-4348; Francis et al. (2001) Prog. Nucleic Acid Res. Mol. Biol. 65, 1-52; Mou and Cote (2001) J. Biol. Chem. 276, 27527-27534). In addition, the presence of a 100-fold excess of cGMP did not affect the rate of hydrolysis of cAMP by LmPDE-B1 (compare FIG. 13B with FIG. 13A). A 50-fold excess of the reaction product 5'-AMP also had no effect on $K_M$ (nor $K_{cat}$) (FIG. 13C). Similar results were obtained with LmPDE-B2 (data not shown). Therefore, LmPDE-B1 and LmPDE-B2 are cAMP-specific PDEs.

These data are in good agreement with the finding that no cGMP-hydrolyzing activity is detectable in whole cell extracts from *Leishmania major* (data not shown). Because PDE-catalyzed hydrolysis is the only mechanism by which a cell can dispose of its cyclic nucleotides (except for possible export mechanisms; Guo et al. (2003) J. Biol. Chem. 278, 29509-29514), the absence of a cGMP-hydrolyzing PDE activity from Leishmanial cells suggests that cGMP signaling may not exist in *Leishmania major*.

Example 5.4

Activity of LmPDEs in the Presence of PDE Inhibitors

FIG. 14 shows the effects of several commercially available PDE inhibitors (100 µM) on LmPDE-B1 and LmPDE-B2 activity in the presence of 1 µM cAMP. Both enzymes were insensitive to the broad spectrum PDE inhibitor IBMX but were partly sensitive to trequinsin, dipyridamole, and etazolate. Trequinsin and dipyridamole inhibited LmPDE-B1 activity with $IC_{50}$ values of 96.6 and 22.6 µM, respectively.

The observed inhibitor profile, including the fact that dipyridamole and trequinsin were the most potent compounds, closely corresponds to that reported previously for trypanosomal PDEs (Zoraghi et al. (2001) J. Biol. Chem. 276, 11559-11566; Zoraghi et al. (2002) Proc. Natl. Acad. Sci. USA 99, 4343-4348; Rascon et al. (2002) Proc. Natl. Acad. Sci. USA 99, 4714-4719). The fact that several potent and specific inhibitors of different human PDEs had no effect on the Leishmanial PDEs strongly suggests that the development of *Leishmania*-specific PDE inhibitors is feasible.

Example 6

The following example describes the methods used to determine the effect of the PDE inhibitors dipyridamole, etazolate, and trequinsin on the proliferation of *L. major* promastigotes in vitro.

*L. major* MHRO/IR/75/ER or LV39 promastigote forms were cultured at 27° C. in SDM medium containing 5% heat-inactivated fetal bovine serum (R. Brun and M. Schonenberger (1979) Acta Trop. 36, 289-292). Cell proliferation was assayed in 5 ml cultures containing various concentrations of dipyridamole, etazolate, or trequinsin dissolved in DMSO (final concentration of 1% v/v) or 1% v/v DMSO as a control. At various times, 150 µaliquots were withdrawn and absorbance was measured at 600 nm in a microtiter plate reader. The correlation between $OD_{600}$ and cell number was strictly linear over at least the range of $3\times10^5$ to $4\times10^7$ cells/ml.

Figure 15:
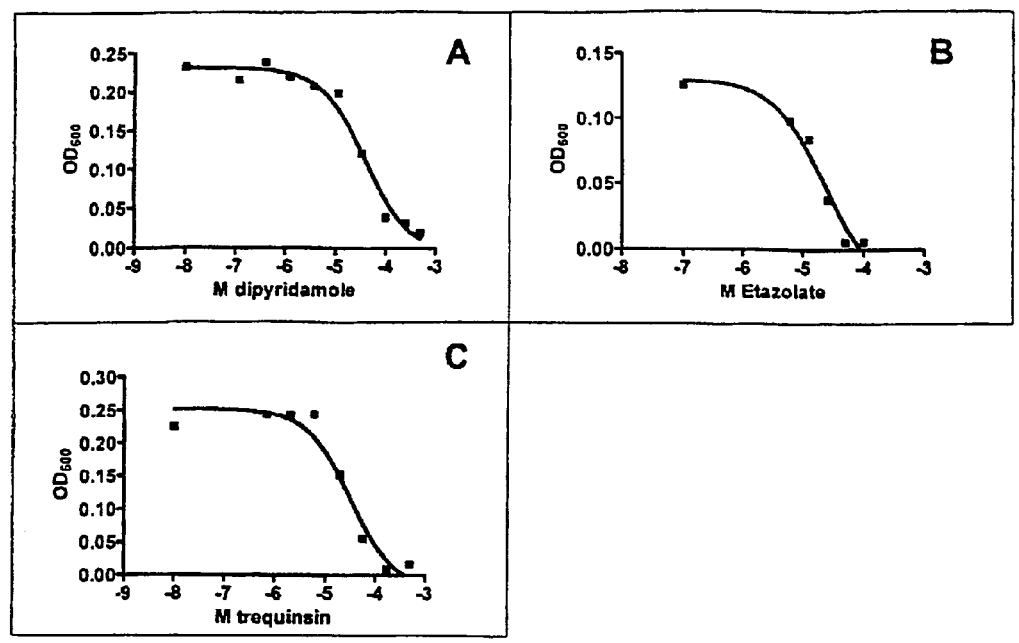
FIG. 15 shows the inhibition of *L. major* promastigote proliferation in the presence of increasing concentrations of dipyridamole (A), etazolate (B), and trequinsin (C).

As shown in FIG. 15, all three PDE inhibitors strongly inhibited promastigote proliferation with $IC_{50}$ values of about 50 µM. The extent of inhibition was independent of cell density, and the effect of the inhibitors was not reduced by prolonged incubation of the cultures.

These results are consistent with the ability of dipyridamole, etazolate, and trequinsin to inhibit the activity of recombinant LmPDE-B1 (see, e.g., FIG. 14). In addition, the data strongly suggest that LmPDE-B1 and LmPDE-B2 are involved in the growth of *L. major*, and they further support the development of *Leishmania*-specific PDE inhibitors for the therapy of leishmaniasis.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically included in the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Although the foregoing invention has been described in some detail by way of illustrations and examples for purposes of clarity of understanding, it will be apparent to those skilled in the art that certain changes and modification may be practiced. Therefore, the description and examples of the disclosure should not be considered as limiting the scope of the invention, which is defined by the scope of the appended claims. Other aspects, advantages, and modifications are within the scope of the following claims.

What is claimed is:

1. An isolated nucleic acid molecule consisting of a nucleic acid sequence that encodes a protein comprising the amino acid sequence set forth in SEQ ID NO: 3 or variants and mutants thereof that are at least 85% identical to SEQ ID NO: 3, wherein the protein, variant, or mutant hydrolyzes cyclic adenosine mono-phosphate (cAMP).

2. An isolated nucleic acid molecule according to claim 1 wherein the nucleic acid molecule consists of the nucleotide sequence set forth in SEQ ID NO: 4 beginning with adenine at position 1267 and ending with adenine at position 4059.

3. The nucleic acid molecule of claim 1, wherein the nucleic acid molecule is a DNA molecule.

4. A vector comprising the nucleic acid molecule of claim 1.

5. The vector of claim 4 wherein the nucleic acid molecule is operably linked to at least one expression control sequence.

6. An isolated host cell comprising the vector of claim 5.

7. The isolated host cell of claim 6 wherein the isolated host cell is a bacterial cell.

8. The isolated host cell of claim 6 wherein the isolated host cell is an eukaryotic cell.

9. The isolated host cell of claim 8 wherein the eukaryotic cell is *Saccharomyces cerevisiae*.

10. A method of producing a *Leishmania* cyclic nucleotide-specific phosphodiesterase (LmPDE) protein comprising culturing the isolated host cell of claim 6 under suitable conditions so as to produce the LmPDE protein in the isolated host cell and recovering the LmPDE protein so produced.

11. The nucleic acid of claim 1, wherein the protein has a $K_M$ value from 1 to 2 µM for cyclic adenosine mono-phosphate (cAMP).

12. The nucleic acid of claim 1, wherein the protein does not hydrolyze cyclic guanosine mono-phosphate (cGMP).

13. The nucleic acid of claim 1, wherein the protein substantially hydrolyzes cyclic adenosine mono-phosphate (cAMP) in the presence of up to about 100 µM of a phosphodiesterase inhibitor chosen from cilostamide, zaprinast, etazolate, Ro-20-1724, rolipram, isobutylmethylxanthine (IBMX), 8-methoxymethyl-IBMX, papaverine, milrinone, petoxifylline, and erythro-9-(2-hydroxy-3-nonyl)adenine.

14. The nucleic acid of claim 1, wherein the nucleic acid sequence encodes a protein comprising the amino acid sequence set forth in SEQ ID NO: 3 or variants and mutants thereof that are at least 90% identical to SEQ ID NO: 3.

15. The nucleic acid of claim 14, wherein the nucleic acid sequence encodes a protein comprising the amino acid sequence set forth in SEQ ID NO: 3 or variants and mutants thereof that are at least 95% identical to SEQ ID NO: 3.

16. The nucleic acid of claim 1, wherein the nucleic acid sequence encodes a protein comprising the amino acid sequence set forth in SEQ ID NO: 3 or variants and mutants thereof that are at least 99% identical to SEQ ID NO: 3.

* * * * *

SEQUENCE LISTING

<160> NUMBER OF SEQ ID NOS: 6

<210> SEQ ID NO 1
<211> LENGTH: 631
<212> TYPE: PRT
<213> ORGANISM: Leishmania major

<400> SEQUENCE: 1

Met Leu Asp Phe Leu Glu Gln Leu Gln Gln Leu Ala Ser Val Tyr Ala
 1               5                  10                  15

Ile Cys Gly Asn Ala Val Ser Val Met Ala Gly Met Ser Asp Thr Ala
            20                  25                  30

Glu Glu Leu Thr Phe Arg Ser Tyr Asp Ser Leu Glu Gly Ala Ser Tyr
        35                  40                  45

Ile Cys Asn Leu Asn Glu Lys Ala Leu His Thr Ala Lys Ala Ser Leu
    50                  55                  60

Cys Asp Asn Ala Asp Trp Ser Ser Phe Phe Arg Glu Val Gln Leu Ala
65                  70                  75                  80

Phe Asn Ser Gly Arg Val Thr Val Gln Pro Gly Asn Ala His Arg Val
                85                  90                  95

Ala Val Asn Ala Ala Ala Pro Val Ser Ala Asp Ser Lys Gly Leu Ala
            100                 105                 110

Cys Ser Met Glu Val His Cys Leu Ser Gly Ser Gly Glu Lys Cys Ala
        115                 120                 125

Thr Phe Val Leu Glu Arg Thr Thr Glu Asp Gln Gln Lys Tyr Ile Leu
    130                 135                 140

Glu Ser Met Leu Gln Ala His His Met Tyr Asn His Pro Lys Glu Tyr
145                 150                 155                 160

Glu Gln Lys Leu Leu His Ile Met Glu Ala Lys Glu Ile Ala Cys Thr

```
                         165                 170                 175
Lys Arg Glu Ala Leu Asp Arg Glu Leu Val Ala Leu Asn Asp Asn Leu
            180                 185                 190

Thr Arg Asn Lys His Lys Gln Lys Ile Asn Asn Glu Arg Lys Glu Glu
            195                 200                 205

Leu Leu Lys Lys Leu Gly Gly Tyr Ser Thr Glu Asn Thr Gly Asn Pro
            210                 215                 220

Trp Gln Ala Ile Gln Glu Gln Gln Arg Thr Ala Gly Glu Asn Thr
225                 230                 235                 240

Lys Ser Arg Leu Pro Ser Pro Leu Gly Asn Arg Thr Cys Lys Asp Phe
                245                 250                 255

Asp Leu Val Leu Phe Arg Met Ile Lys Ser Arg Trp Leu Ser Pro Glu
            260                 265                 270

Gln Cys Asp Ala Ser Ser Pro Ala Asn Arg Val Val Gln Pro Tyr Ser
            275                 280                 285

Lys Glu Asp Leu Ala Ile Gln Val Ser Gln Leu Ser Gly Ser Arg Ala
            290                 295                 300

Ala Ile Trp Lys Ala Leu Asp Ser Ile Asp Ser Trp Ser Tyr Arg Val
305                 310                 315                 320

Phe Asp Val Gln Ala Ala Met Ser Gly Asp Asp Tyr Leu Ser Leu Ser
                325                 330                 335

Thr Gln Thr His Gly Gly Ser Leu Leu Ile Thr Met Tyr Ala Leu Leu
            340                 345                 350

Cys Met His Asp Phe Leu Gln Lys Phe Lys Ile Asp Glu Gln Ile Ala
            355                 360                 365

Leu Asn Trp Ile Ser Ala Val Glu Ala Ser Tyr His Gly Asn Pro Tyr
            370                 375                 380

His Asn Ser Met His Ala Ala Asp Val Leu Gln Ile Thr Asp Phe Ile
385                 390                 395                 400

Ile Thr Gln Gly Gly Leu Ala Lys Arg Cys Asp Leu Ser Asp Ile Gln
                405                 410                 415

Val Phe Ser Ala Leu Leu Ala Ala Ser Ile His Asp Phe Asp His Pro
            420                 425                 430

Gly Ile Asn Asn Asn Phe His Ile Lys Thr Gly Ser Tyr Leu Ala Thr
            435                 440                 445

Leu Tyr Asn Asp Arg Ser Val Leu Glu Asn Leu His Val Ser Ser Val
            450                 455                 460

Phe Glu Leu Met Lys Asn Pro Ala Phe Asn Ile Leu Ala Ser Phe Ser
465                 470                 475                 480

Asp Glu Gln His His Glu Val Arg Glu Thr Met Ile Glu Met Val Leu
                485                 490                 495

Ala Thr Asp Met Gly Ser His Gly Lys Tyr Val Ala Ser Leu Lys Gly
            500                 505                 510

Lys Met Gln Glu His Ser Ser Phe Thr Gln Thr Ala Glu Gln Asn Leu
            515                 520                 525

Cys Leu Ala Ile Ala Leu Lys Met Ala Asp Ile Ser Asn Cys Gly Arg
            530                 535                 540

Pro Leu Asp Ile Tyr Leu Arg Trp Gly Ala Lys Val Ser Asp Glu Phe
545                 550                 555                 560

Tyr Gln Gln Gly Asp Arg Glu Arg Asn Leu Gly Leu Glu Cys Ser Pro
                565                 570                 575

Phe Met Asp Arg Leu Gln Pro Ser Leu Ala Lys Ser Gln Ile Ala Phe
            580                 585                 590
```

```
Met Asn Tyr Ile Ile Thr Pro Phe Phe Glu Gln Val Ala Glu Leu Leu
            595                 600                 605

Pro Asp Met Arg Phe Ala Val Ala Leu Val Glu Glu Asn Lys Ala Tyr
    610                 615                 620

Trp Ala Asn His Asp Asp Ser
625                 630

<210> SEQ ID NO 2
<211> LENGTH: 10966
<212> TYPE: DNA
<213> ORGANISM: Leishmania major
<220> FEATURE:
<221> NAME/KEY: modified_base
<222> LOCATION: (414)
<223> OTHER INFORMATION: a, t, c, g, other or unknown
<220> FEATURE:
<221> NAME/KEY: modified_base
<222> LOCATION: (423)
<223> OTHER INFORMATION: a, t, c, g, other or unknown

<400> SEQUENCE: 2
tggctaccgc cctgccagca agtaccggag gcgccggctc gttttctttt tgttgccttt      60
tccaagcaac tgacgggaca cgtttcagtg catgcgcatt accacgatgc ttacggtgaa     120
gcacgaccgt gcacattcac tcaaggtatt gtgagcgcga acaagcaaat cccaaaacaa     180
gccgcctgcg tatgtctctg cagtttccca tgtgcaaatc tacctgtctt cgactctgcc     240
gccatccttc tctctttcct aactctgttt ctctttctct gcaacagagc tgaagtctga     300
cgcgcttctc gttctttcgt ttttttcct cttcccccctt ttttttgcag cttctcccca     360
acacggttgg tcgaccgctc cagaaaataa cagcaagagg cgaaacagta acgnaaacac     420
ccnacccacc cacccactca ccaaacaggc ggccgaaaaa aaagactccc ctctgaactt     480
ttgcttttcg ttgctcttcc tgcggtgccg cgctctagca gcggcagcga tgctcgactt     540
tcttgagcag ctgcagcagc tggcaagtgt gtacgccatc tgcggcaatg ctgtctccgt     600
gatggcgggg atgagcgaca cggcagagga gctgacgttc cgttcctacg acagtttaga     660
aggcgcctcc tacatctgca acttgaacga gaaggctctt cacacagcga aggcctcgct     720
ctgcgacaat gccgattgga gcagcttctt tcgcgaggtt cagctggcat tcaactcggg     780
tagagtaacc gtgcagcctg aaatgctcca tcgagtcgcc gttaacgccg ccgcgccagt     840
ttccgccgac tctaaaggcc tagcatgctc gatggaggtg cattgcctgt cggggtcagg     900
ggagaagtgt gcaaccttg tgcttgagcg aaccacggag gaccagcaga agtatattct     960
cgagagcatg ctgcaggcac atcacatgta taaccacccg aaggagtacg agcagaagct    1020
gctccacatc atggaagcca aggagatagc gtgcacgaag cgcgaggcac ttgatcgtga    1080
gctggtcgcg ctgaacgata atttgacacg caacaagcac aagcagaaga taaacaacga    1140
gcgcaaagag gagcttctaa agaagctcgg cggttacagc acagagaaca cgggaaatcc    1200
gtggcaggcg attcaggagc agcagcagag gacagctggc gagaacacga agtctcggct    1260
gccgagcccg ctcgggaacc gcacctgcaa ggattttgat cttgtcctgt ttcgcatgat    1320
caagagtcgg tggctgtcac cggagcagtg cgacgcatcc tcgcccgcga atcgcgtcgt    1380
gcagccgtac tccaaggagg acctcgcgat ccaggtgagc caactctcag gtagccgagc    1440
tgcgatatgg aaggcactgg attccatcga ctcatggagc taccgcgtgt tgatgtccca    1500
ggcggctatg agcggtgacg actacctctc gctctcgacg cagacgcacg gcgggtctct    1560
cctgataacc atgtacgcac tgctgtgcat gcacgacttt ctgcaaaaat tcaagattga    1620
```

-continued

```
cgagcaaatt gcgctcaact ggatcagcgc agtggaggcg agttaccatg gcaacccgta    1680
tcacaactcg atgcacgccg cggatgtgct gcagattacg gacttcatca tcacacaggg    1740
agggttggcg aagaggtgcg acctaagcga catccaggtc ttctctgcct tgctggctgc    1800
ctcgatccat gacttcgacc accctggcat caacaataac ttccacatca agacaggcag    1860
ctaccttgct acgctgtaca acgatcgcag tgtcctggaa atctgcacg tgagcagcgt     1920
tttcgagctc atgaagaacc cagccttcaa catcctagcc agcttcagtg atgagcagca    1980
tcatgaggtc cgcgagacga tgatagagat ggtgctggcg acggacatgg gctctcacgg    2040
aaagtacgtg gcgagtctga agggcaagat gcaggagcac tctagtttca ctcagaccgc    2100
cgagcagaat ctctgcctcg cgattgctct gaaaatggcc gacatttcaa actgcgggcg    2160
cccgcttgac atttacctgc gctggggagc gaaggtgtcg gatgagttct accagcaggg    2220
cgaccgtgag cgcaacctgg gcctcgaatg cagtcccttc atggatcgcc ttcagccgag    2280
ccttgcgaag agccagattg ccttcatgaa ctacatcatc actcccttct tgagcaggt     2340
ggccgagctt ctgcccgata tgcgcttcgc ggtggctttg gtggaggaaa acaaagcgta    2400
ctgggccaac cacgacgact cgtagagaca tcccactcac cgcctttcgt ggcgcacctg    2460
tttcctcacc gccccctttt ttcgtggtg acgcgctctt tgtggataca cacacacaca     2520
cacacacaca cacacacaga cacagtcttc gttctaccta gtgtcacgtc ggttttcttc    2580
accggaagcg gggcaaggat gtatatatct atttctctct cttgttgcag ctcccacctt    2640
cactgcctcc ctcgttgcct ctccttgcga tgtattatta ttattttgt tgttctcgcc     2700
gattatttct tccacgctga tgggaaggtg taaaaggcgg aggagaaggg ggagaggagt    2760
tgaaggaaaa aggagtaaca ccaactggaa ccctcactcg ttttcttttt cgccttttg     2820
ttccgtatcc gctcagtctc cttaattttt ttttgtggta tgaatttgct gagttgtcct    2880
cttgaagtgc gaacacttgt aatccctctg gtggcttttg acacgtgtgt gatgagctcc    2940
acacttctct tcttgcttcc ttcccacttt ctcgtcttct caccctccat tcttcacctc    3000
acatgtgcat ctggcgtgtg tgcacgtatg cgtaacgagc ctgtcgcaca cgcttcttcg    3060
cctctctcat gcttttgttt gtgcatttcc ttcatgccaa cctccgtgtt tttatgttct    3120
attttacgc ttgctttcaa ccctgtgtgt gtgcttccgc cgccgttttt atttttccct     3180
cctcagtggt tgtttgtggt ggtacccgaa ttgccgtttc gcacatacgc gggcttcgcc    3240
ttgacgaggt ttacctctct cttccttcc ctgggtttgt cgcagaccgc cctagctccc     3300
tcccttcccc acatccctcc cgatcctttg gccccccttg tgcaaaacaa gaaagagaga    3360
gggcaccgtc cacctcctt ggttctctct gttttcttcg cctcttcgat gatgcgctta     3420
gtttgactga cgcggtgcag cgggtagcgt ttacatgctg ttgccttttt ttttgtattt    3480
cctttttgacg attatggttc tacgcggctt gcgtttggcg gcgacaagcc actactctgt    3540
gaagaaaaac aaacaagaaa aggcgttgtc aatgcgaaag ggtgcgctac tggagatgga    3600
gatgagcgtt ggtgtcatct tcgttggtgc ttcccatcgc tgagttcatg cattgcgact    3660
ttaggcctta tccaaggtct ggccggcact tctccacaag gattttgtca ctgccgtatg    3720
aactcggtag ccaggctatg attcccatct cttgcttctg gagcacagcg caacccccc     3780
tttgcatcct tctcttctcg agtccaacgg ctcttctccc tttctctcct cttctcttcc    3840
gctgcccgcc ttcgtcgacg tttctgggtt tcatgccact cccccttcc ctgcacggag     3900
gaaaagcaga agtacagttt ctcaaaatct tgtctctaca cggcttgcca gtgtccgcac    3960
```

```
tcgtcccgtt actttcacac ggcgcacacg acgacactta cccccccccc tacacacaca      4020
cacacacaca cacacacaca cacacacaca cactgcacag tgtcacggtg catcatctga      4080 aacattttc cttttttcct tttcgcggaa cacattcttt cttcctatta ctattttgct      4140 taccctttgtt ggcagcctgc taccattttt ttgtttccgt ttccttgtgt tggcgattat    4200
atacatatat acatatatgt atatatatat atatatgtgt atatgcttcg atcatcgtgg     4260
gtctttgcat ccgtgtgcac ctctcgcaac acacttctgt cagcgcaatt gtcttttga     4320 aaagtagatt gttggccaca cactctgcga tagcgcgttt tccagggacg agctgcagtc    4380
tgcacacttc accgcctcat caccttgacg ttattattat tattttaagc ttcccgcaga   4440
gtttgtctgc aagttgaccc agagtctttt actcgagcgc acaccatcaa acatcagcca   4500
tgcatctttc tgagctttgc cgggactcca acatcgacgt gatcatcgct cgccttcgcc   4560
aggtagcacc cctagagcct gcgccggctt tctctttgtc cgaaggagca gcagatgacg   4620
acacaactcc cgcaactgga cactcggact ttcatgggct gtggagctat caggacaatg    4680
acgggcgtac agccttccat tgggccatag cgctcaagaa cttcgacctg gctcgcaagt    4740
tgatgcaggc accgtacaat tcgcctgtgc tgaccgaaga tgaggagtgg agcacaccgt   4800
ttgccactgc ctgtagcgtt ggggcaccgc tagacctgct gagagagatt ctggaccgga    4860
gtgtggttga gttagccgcg cacatgaagc agaaggagca tcagcaaaac cccacttccg    4920
aggagcagaa cagcagcagt gccgccgtga ccgagcctgc cgaggggagc agcgacggaa    4980
agccgacaaa gttcttgtca gacatgccgg gaattttgca gcccgtcgac ggcactcctg    5040
cttctattag cgccgtgctt gttgacgccg aggatgcgac gggacaaacg cctctgcttc    5100
tagctgtggg acgtgggcac ctgagcattg tgcgcttctt gctggagaac ggtgcaaatt   5160
tgatgcatca aaaccgcagg ggccagtcgt gcctgcatcg cgccgtgaac cgcggaaaca   5220
tggagctcgt tgagtttctt gtttcgacaa gtgagaacaa cgcgaagagc aaggcagtgc   5280
atcgggtgtg gatggacctg cgggacaaac acggcgactc cgcgctcttc tacgcttcca   5340
tggataacaa tgaggagatt ggccggtacc tgctgcgcca cggcgccgat cgcgagctgc   5400
gcaatgcaga cggcaaagca ttctgggaag tgtagacatc gaagaagaca acaagggaca   5460
ttgagcgcaa ccgaaaaatc gtcgacttca gctcttgttt agcatatgtc gagaaggcca   5520
tcgctgttct tgagggcagg gacttatgcg gctgtgcatg gctactgtgc gacaagaggg    5580
catcaattca ggaccaccta gcgcgtgtac ttcttgcttc ttaccacccc ctcccccaca   5640
tgtcgccgct tccccatcaa agtgtgtgcg taactttgaa aacgcagtga tcatctcggc   5700
ttgtatcgca tttttttctc catttttttt tttgcttgga cctcccccaa acaaaaggaa   5760
aagggttgag tgtggtggt cgtgacccac tcgtcaccat gcgcgtcgtg ggaaggaagg    5820 ggcggggtg tacggtaaca ctgcacatgc acacatacgg tatgccactt tggggctctt    5880
ttgaaaagct aaagaacaac aaaaaagaga cagcactcat ctgcaagtat ggtctttgtc   5940
attgtttctt cttgagctgc accgcaggag cccttgcgcc acttcgacgc cgctgcgcat   6000
agttcggtgt ctctgtcgca cgctgcggca cgttgcgcca cggggcaaca cccaagctcg   6060
accaagcctc gtgcttcccc cacttggctc gtgtttgttt tgctctcgtg cgccccctct   6120
tttctggtcg ttttttccatt tcgtgccaat cagctctctg tgcccccccc ccttcccctc  6180
tctctcactt cagtcccttt tgtacaacgt accgcacgtt ttacgttgga aagtggccgt    6240
catgaagcgt cgtgagcagc gccgacacgc cgagcgcgag cagctgccaa ctgccttgac    6300
gaagctggtc cagctcattc catccgacga ggatgcgcgc cgctaccttg caagggagtt    6360
```

```
cgccgacatc acgcaggacg aagcagggtc gaatgcaccg tgctccgcgg agggaagtgg   6420
gcacgatgct ggcgcaggcg acgcgtggat ctacggcagc gggctcgaga agctgctgtc   6480
ggttctagga gaggaggcgt gtcctgatgg ggctttcgat attgttcgta tcactcgccg   6540
cgtgccgcgc agccaatcca cgattgacag gatcaatgtg gcggagttgt gctttgcggt   6600
ttcccaggcg tcgggcccgg tggatgtcca cgagcgacgt cgcactgctg gtgccacgtc   6660
cggaccgctg gacgagacga tacctcttct gcagtactac cggggagtc gatttgacgc   6720 cattgtgcgt ggcgaggacc catcttctcc tgcagctcga catgccgccg ccgacgcagc   6780
actattggag gaaaatagca gccatcttga gatcgcctct gcaggcaacg gcagcagaaa   6840
gaacgttgac tcggaatggc cggcgttcgt gcagagcatg tctacgccgc ttcctatgac   6900
gcttcgcctg caccacagtg agcgtgcttt ggaggccatc gcaacccgca tgctcaccac   6960
acccgacatt gccgccgtag tgcgtcctgt gaccgccttt ccgtccagcg ctggtctcta   7020
ctcctgcagc aatagcgact accacagcca caagcgcgtg gagtacgtct gccgcaccct   7080
gcacgctgct agcgccgtgt catttcagga ggtggtgtcg gcgataccgg tgtttgtgct   7140
ggatgtgcag ccgcaacaca ctgtcgtgga tctctgcgcg gcacctggca gcaaaacagt   7200
gcaggccttg gacaccatgc tgagcggtgg gtggtctgca gacgtctgtc gaggggtgct   7260
catcgccaac gaaaaggaca gagtgaaggc gacgcagaca cttccggcgc ggctgaagcg   7320
ctaccacgcc ccaaacgtga tgactacccg atgcgacggt gtgcagtggc ctcgtttgta   7380 cttttaacgat cctacgaacc caagcagcga gccgcaagaa cggcggtttg accgcatcat   7440
ctgcgacgtc ccgtgcagcg gcgacggcac catccgcaag gagtgttcca tcgccacaac   7500
atggtcggca agctacgtga agtccctcgt gccaacccaa cgtgcgttgc tgtgccgcgg   7560
ccttgacctc ttggccacag ggggcattct ggtttacagc acgtgcagca tgaatccgaa   7620
ggaggacgag gaggtggttt gcgtcgggtt ggaggctttc ggcgacagtg tcgagctcat   7680
cgacgtgaat gcggttctac aggagaaggg atttcacctg cactcggcag gagggattct   7740
ctccccgaat gtggagggga tgcagcaccc ggtgctgccg ccgacgtacg acggcaacaa   7800
ggtcctgcgc attttgccgc atcgtgatga caccggcggg ttctttgtgg cggcttttcg   7860
caaagcaaag cagccagacc ggacggcgcc cacagtgatt cgacacaagc tgaaccactg   7920
gacgaaaggc aagctgtggg cgccagttgg cgtcgaggac gaggcgtggg ccaacatatc   7980
aaccttctac ggctttgacc gccgcgacga agcgaacttc gtctactatg acgccactag   8040
ctcttcgtcc gggaaaggcc tcgtgcctct gtatcacctc aatccaaatg gtgggcctat   8100
acgccgcatc gtgctctcga ctccggcgct ggcggatatg gtgctgcgca cacgtccgta   8160
caagggccct ggcgtggagg tggtgtccgt cggtatgcgc gcgttcgagg catacgacgg   8220 aaggttttg ccaactgcgg cctgccggtg gcgcgccgtc gttgagtccg cctctttttt   8280
ggcaccgcgc tttactgccc gaaggctgca cttccacgtt tcgaagcaca agcagctact   8340
cgaggatctg ctccgaaacg gccacgttta cacgcgagat cactgga gga cagtgttggg   8400 tggagatcct gctgttgtag ccgctaacgc gaatccgaag gcgctggtca agcctggcag   8460
ccgactcgag gcgttgctga cgcagggcag tagtgaatct accatctctg acgaggaggt   8520
ggcggtgctg ctgacaagcc acgtggaggt agggtgcgtt ttggtgggca tcctcttcga   8580
cgagccgacc gatgcagccg ctggtccgtg gtacatgagc gcgacgctga gcgggcacaa   8640
gctggagctc gccatcgatg gctctctgcg tgcgttcggg ttgatgacgt tttttggcat   8700
```

```
tcacgacgtt gagcgtggct cgctggccgg caacaacatc ggcagtgcgg tcgcagacga    8760
agagcctgag gagcaggcaa aggaggtgta gcaccggaag cttcacacgg cgtggtgtcg    8820
cataactcct gtgctttcac tgcagtggct tatcgagact acagttacat tcgatttcaa    8880
tcgaagaggc catggagcct gtctgcactg ttgatccttc tccttttttt gcgtatgcgt    8940
actattctaa gcgagtaacc gcatcttcac tgactaaacc gccaaacttc atgagtcgca    9000
ggagcagtat aattgtcgcc gagcccctca tcacgtgtat gaggggcgaa acgaaaaatg    9060
atgagaggcg atgcatggct tttcaatagc cgtgacgcgt ccgtgtgtgc gctggattcg    9120
ctgctctggc ttttccacga aggggatgga tcgcgcaata cacgcgcgtt ggaatgcacg    9180
gccattctcg ctctgtgctc cggcgtcctc ttgagggtgc ggctggtgtt ggagtggggt    9240
tgagggtcgc cgagaagacg cgtgctttct gaacagctca cgagcagagc ctctgctact    9300
tgaaccaact ctcttccact acgaacgctc tttcggtatc ttcaatccat cttctctgtc    9360
ttgctattcg gtcttcgtcc accttggctt cacgaagaag ggaagccaag cctcagcaca    9420
cagcaacatc cgcacaagcc gtaccctta ccacctctgt ggttccactc catctccttc    9480
actggtgtac acgatataat cggcgttttt cttctctgtt gttgccctcc tttctctctc    9540
gtgctcctgt tgggccattt cgatacgcgc aagcgtcgct atttcgtgct ttacatcttg    9600
cgttggtctc gccccgattg ctcgtggcat tttctcgtca tcgttttttcc gtctccgtac    9660 gttgccgtgt ttctctttac ttctatggag gcacgttgtg catcttcgcc cctctccgct    9720
tctttgtcag acagcgcggc caaggcgagg ttggtcgggt gcgcgggcgg tctcatttct    9780
ccatagctcc gtgcttttaa tacaccctcc ttcctcctcc cttgtttcca taactcgtta    9840
ttttcttgtt tctggggggg gttcgacccc ttttgtgta atcagcacca tgcaggtcgg    9900
tgtatatgac agagatgatc agatgtgcca gtatgagggc tgcacggaga tcgatctgct    9960
gcctgcccgg tgctccaact gcgacaagcg attctgcacc caccatctct cccacagcgc   10020
acatcgctgt ccggccgtga cggatgtgcg ggtcgggacg tgccccatat gctatcgcgt   10080
tgtaccgttg gagtacccgc gccaatgcat ggacgaggcg gtgtcccggc acattgaccg   10140
aggatgtcgc gatgtaccgc agggcagctt attttacggg ggcgcctctg cgaaggggcg   10200
gcccggccag gcgagaggtc gccgcttggg cggctcggca cggccgtgca gcattcaagg   10260
ctgccacgag gcctccgaga cgcgcgtgga agtgtgacca atgcggccag acattctgcc   10320
ttcagcaccg cggacctctg cagcaccact gccgcgccgc cgccgccacg cgcagcgccg   10380
tcgcgccctc cccttcagag cgggatgctg gcatgctggt gtctctgccg ggtgacaagg   10440
cggtttccgt ggcatgtctg ctcactcatc ccgccaacac tcccgaaaag gcggtgggca   10500
aggcgacaga gctgccctcg gacatggtga catgcctcgt gtgcttcctc atacccactt   10560
gtgtgtccaa aaaggacggg aacgctggct gcgaagagtt cgagccggtg ccccgttct    10620 tcatgttcat gcccaagaat acagcactag gccgtctcct ggacacggcg gtggatcgtg   10680
ccgccatgaa ctcaccggcc gtgcgcaccg gaaaccctg gaacttgttc gccgtcacac    10740
tgcccatcca cgccgaggcc gaggcagcct actattctcc tcttacactc tcgacggtgg   10800 tgaaaagag tgctgtcggc atggcggagc gcactattgt gttttctctcg ccgctccaag   10860 ccttgcccga aggcgtgatc aaggcggtga aggacttgga taggaaaggg tcgtggccgt   10920
caacgtcatc gtcctccagt caagggtgtc aagtgatgtg atgagg               10966
```

<210> SEQ ID NO 3
<211> LENGTH: 930

<212> TYPE: PRT
<213> ORGANISM: Leishmania major

<400> SEQUENCE: 3

```
Met Ala Tyr Phe Thr Ala Lys Arg Ala Ser Ser Met Gly Ala Ser Thr
1               5                   10                  15

Val Pro Ser Gly Asn Asp His Leu Leu Glu Ala Leu Thr Leu Cys Asp
            20                  25                  30

Cys Ile Leu Ser Arg Tyr Lys Arg Cys Gly Val Gln Leu Asn Asp Ala
        35                  40                  45

Glu Ala Ala Phe Ala Asn Leu Gln Gln Arg Ile Ser Ser Ile Ser
    50                  55                  60

Gly His Ala Ala Asp Ala Ala Cys Pro Ala Gly Ala Thr Arg Lys Gln
65                  70                  75                  80

Ser Gln Glu Leu Gly Leu His Glu Tyr Ala Gln Leu Ala Gln Arg Cys
                85                  90                  95

Leu Ile Phe Gln Asn Pro Leu Ala Gln Ile Val Ala Thr Ile Asn Glu
            100                 105                 110

Glu Phe Ser Lys Leu Val Ser Cys Ser Val Arg Thr His Tyr Ala Asn
        115                 120                 125

Thr Asn Asp Ala Val Leu Cys Asp Pro Val His Asp Thr Val Ala Thr
130                 135                 140

Ile Asp Thr Ser Thr Pro Ile Gly Arg Cys Ala Lys Thr Lys Thr Thr
145                 150                 155                 160

Val Thr Ile Ser Asp Thr Val Tyr Ile Pro Leu Cys Tyr Asn Ser His
                165                 170                 175

Val Val Gly Cys Leu Glu Val Glu Ser Thr Ala Ile Asp Thr Ser Thr
            180                 185                 190

Pro Phe Phe Gly Tyr Leu Leu Gln Val Ala Ala Leu Thr Leu Gln Asn
        195                 200                 205

Ala Thr Ser Ile Asp Thr Leu Arg Trp Glu Thr Arg Lys Ala Glu Ala
    210                 215                 220

Met Val Gly Met Ala Thr Arg Leu Ala Arg Asp Thr Leu Glu Glu Ser
225                 230                 235                 240

Val Leu Val Gln Ser Ile Ile Asn Thr Ala Lys Thr Leu Thr Glu Ser
                245                 250                 255

Asp Arg Cys Ser Ile Phe Leu Val Lys Ala Asp Gly Ser Leu Glu Ala
            260                 265                 270

His Phe Glu Asp Gly Asn Val Val Leu Pro Ala Gly Thr Gly Ile
        275                 280                 285

Ala Gly His Val Ala Glu Ser Gly Ala Val Val Asn Ile Pro Asn Ala
    290                 295                 300

Tyr Glu Asp Asp Arg Phe His Arg Ser Val Asp Lys Val Thr Gly Tyr
305                 310                 315                 320

His Thr Arg Thr Ile Leu Cys Leu Pro Ile Ala Phe Glu Gly Thr Ile
                325                 330                 335

Val Ala Val Ala Gln Leu Ile Asn Lys Leu Asp Met Val Thr Gln Ser
            340                 345                 350

Gly Gln Arg Leu Pro Arg Val Phe Gly Arg Arg Asp Glu Glu Leu Phe
        355                 360                 365

Glu Thr Phe Ser Met Phe Ala Ala Ala Ser Leu Arg Asn Cys Arg Ile
    370                 375                 380

Asn Glu Thr Leu Leu Lys Glu Lys Lys Ser Asp Ala Ile Leu Asp
385                 390                 395                 400
```

```
Val Val Ala Leu Leu Ser Asn Thr Asp Ile Arg Asp Val Asp Ser Ile
            405                 410                 415
Val Arg His Val Leu His Gly Ala Lys Lys Leu Leu Asn Ala Asp Arg
            420                 425                 430
Ser Ser Met Phe Leu Leu Asp Lys Glu Arg Asn Glu Leu Tyr Ser Lys
            435                 440                 445
Met Ala Asp Ser Ala Asn Glu Ile Arg Phe Pro Cys Gly Gln Gly Ile
            450                 455                 460
Ala Gly Thr Val Ala Glu Ser Gly Val Gly Glu Asn Ile Met Asp Ala
465                 470                 475                 480
Tyr Ala Asp Ser Arg Phe Asn Ser Ala Val Asp Arg Gln Leu Gly Tyr
                485                 490                 495
Arg Thr Gln Ser Ile Leu Cys Glu Pro Ile Thr Leu Asn Gly Glu Val
            500                 505                 510
Leu Ala Val Val Gln Leu Val Asn Lys Leu Gly Asp Asp Gly Ser Val
            515                 520                 525
Thr Cys Phe Thr Pro Thr Asp Gln Glu Thr Phe Lys Val Phe Ser Leu
            530                 535                 540
Phe Ala Gly Ile Ser Ile Asn Asn Ser His Leu Leu Glu Phe Ala Val
545                 550                 555                 560
Asn Ala Gly Arg Glu Ala Met Thr Leu Asn Leu Gln Arg Asn Ser Ile
                565                 570                 575
Thr Ala Gln Arg Ala Pro Lys Ser Val Lys Val Ile Ala Val Thr Pro
            580                 585                 590
Glu Glu Arg Glu Ala Val Met Ser Ile Asp Phe Gly Gly Ala Tyr Asp
            595                 600                 605
Phe Thr Ser Pro Gly Phe Asn Leu Phe Glu Val Arg Glu Lys Tyr Ser
            610                 615                 620
Glu Pro Met Asp Ala Ala Gly Val Val Tyr Asn Leu Leu Trp Asn
625                 630                 635                 640
Ser Gly Leu Pro Glu Lys Phe Gly Cys Arg Glu Gln Thr Leu Leu Asn
                645                 650                 655
Phe Ile Leu Gln Cys Arg Arg Arg Tyr Arg Arg Val Pro Tyr His Asn
            660                 665                 670
Phe Tyr His Val Val Asp Val Cys Gln Thr Leu His Thr Tyr Leu Tyr
            675                 680                 685
Thr Gly Lys Ala Ser Glu Leu Leu Thr Glu Leu Glu Cys Tyr Val Leu
            690                 695                 700
Leu Val Thr Ala Leu Val His Asp Leu Asp His Met Gly Val Asn Asn
705                 710                 715                 720
Ser Phe Tyr Leu Lys Thr Asp Ser Pro Leu Gly Ile Leu Ser Ser Ala
                725                 730                 735
Ser Gly Asn Asn Ser Val Leu Glu Val His His Cys Ser Leu Ala Ile
            740                 745                 750
Glu Ile Leu Ser Asp Pro Ala Ala Asp Val Phe Glu Gly Leu Ser Gly
            755                 760                 765
Gln Asp Val Ala Tyr Ala Tyr Arg Ala Leu Ile Asp Cys Val Leu Ala
            770                 775                 780
Thr Asp Met Ala Arg His Gly Asp Leu Ser Arg Val Phe Asp Asp Met
785                 790                 795                 800
Ala Lys Ala Gly Tyr Asp Ser Asn Asp Gln Glu Ser Arg Arg Leu Val
                805                 810                 815
```

```
Met Glu Thr Leu Ile Lys Ala Gly Asp Val Ser Asn Val Thr Lys Pro
        820                 825                 830
Phe Glu Thr Ser Arg Met Trp Ala Met Ala Val Thr Glu Glu Phe Tyr
        835                 840                 845
Arg Gln Gly Asp Met Glu Lys Glu Lys Gly Val Glu Val Leu Pro Met
        850                 855                 860
Phe Asp Arg Ser Lys Asn Asn Glu Leu Ala Arg Gly Gln Ile Gly Phe
865                 870                 875                 880
Ile Asp Phe Val Ala Gly Lys Phe Phe Arg Asp Ile Val Gly Asn Leu
                885                 890                 895
Phe His Gly Met Gln Trp Cys Val Asp Thr Val Asn Ser Asn Arg Ala
                900                 905                 910
Lys Trp Gln Glu Ile Leu Asp Gly Arg Arg Asp Ser Ile Arg Pro Ser
        915                 920                 925
Ile Val
    930

<210> SEQ ID NO 4
<211> LENGTH: 7095
<212> TYPE: DNA
<213> ORGANISM: Leishmania major

<400> SEQUENCE: 4
ctgcgagcgg gaggacaggg cgaggcaacg tgtgcgagat aaggtcgtgg cacagagagg      60
atacggctat gagagggatg tgtgctgttg gtgtgtcctc aacgttcgtg ctaaaggtcc     120
gtccaaaggt gaggaagttg ggacgaggaa gcatgcatgg acggtctcgt ggcctcatca     180 cctccttctcg gtgccatcat taccaccctt cgctcctgct ttttcgccgc catgcccagc     240
gggacttttt ttcgtcttgt tcgctttcct cctcctcctc ctcctcctcc tgtggttgct     300
ttcatgcatg taatctatgc gcggtgtgcg gactacaccg tcgcccaccg ccctcccctc     360
tccccgtctt ttcctccttg tttagcgttc tctttttctt ggcaccccct cttttttccg     420
agcaacgcaa tgcctccgcc tccccacccc gtatgtcgca cccctgtgtc ccttgcgcac     480
gcctcttacc gtactgtaac cctttttcgcg tacacgggca ccatctcggt tttacttgta     540
tattagtctg gcctgccaaa atcatgaagt ccaccacacc tgcctagtcc atgccgccta     600
tctgttgccg cgattctgca ccgctcctta tccagcgcgt cgttggagta gaatctcccg     660
ctggcccgtc ccgttgccct tgtatggaga ccgccaagag ttgtggcaca ttcaaagttg     720
ccccatgtgc gacccggcga ttaggcaact gtaaaaaaag gagcggcgtc attcacagga     780
gtagacggtg cgttctgccg tggcctcttt cgtgctgctc tctctctatg catctctctc     840
cttctcacgg attactctcc gtggccactg cgtgccctcc tggctgtttc ccggctcttt     900
tccccatttg tgcgctcttc catccatgca cccaatcaaa aaatcggatg cggtcatgtc     960
tgtcgtgcgt gcatctctgc atccgtctgc cagtgcgtgc gtgcgtgtgt gtgtgtgtgt    1020
gtgcgcacgt cagaaccgtc tcaagtccct cacctcagcg tcaatctacc ctcattgtcg    1080
tcgtcggcct tgacgtgttt tcggtcatcg tttcaccatt gtctcggctc aacgaccaca    1140
atagaaaaaa gcatagggat cggaaagctg tggcctatac acgttcacgg gtgcccgctc    1200
agcgctggac acgtgcgcac gtccaccgca tcacagtgag agacggagag aaaccagcgt    1260
agcgccatgg catatttcac ggccaagagg gcgtcctcga tgggtgcaag caccgttccg    1320
agcggcaacg accatctcct cgaggcactc acgctgtgcg actgcattct gagccgttac    1380
aagcgctgcg gggttcagct caacgacgcg gaggccgccg ccttcgccaa tttgcagcag    1440
```

-continued

```
cgcatatcta gcatctccgg ccacgcagca gacgccgcat gcccagcagg cgccactcga    1500
aagcagtcgc aggaactggg actgcacgag tacgctcaac tggcgcagcg gtgcctgatc    1560
ttccagaacc ccctcgccca aattgtcgcc accatcaatg aagagttctc caaacttgtg    1620
agctgttcag tgcgcacgca ctacgccaac acaaacgacg cggtgctatg cgacccagtg    1680
cacgacactg ttgcaaccat cgatacatcg accccatcg gcaggtgtgc gaagacgaag    1740
acgaccgtta ccatttccga cacggtgtac atcccctat gttacaacag ccacgtcgtc    1800
ggctgcctgg aggtggagag caccgcaatc gacacgagca cgccgttttt cgggtacctg    1860
cttcaagtgg cggcactaac actgcagaac gctacctcca tcgatacact gcggtgggag    1920
actcggaagg cagaggccat ggtgggcatg gcgacacggc ttgctcgaga cacgttggag    1980
gagtcggtgc tggtgcagtc catcatcaac acggcaaaga cgctgacgga gagcgaccgg    2040
tgtagcatct tcctggtgaa agcggacggc agcctggagg cgcacttcga ggacggcaac    2100
gttgtggtgc tgcctgcggg gacgggcatc gcaggtcacg ttgcggaatc tggcgccgtg    2160
gtgaacatcc cgaacgcgta cgaggacgac cggttccacc ggtccgtgga caaggtgact    2220
ggctaccaca cgcgcacgat cttgtgtctg ccgatcgcgt tcgagggcac gatcgttgcc    2280
gttgcgcagc tgatcaacaa gctggacatg gtgacacaga gcgggcagcg gcttccgcgc    2340
gtgtttggac ggcgcgacga ggagctgttc gagacgttct cgatgttcgc tgcggcgtcg    2400
ctgcgcaact gccgcatcaa cgagacgctg ctgaaggaga agaagaagag cgacgcgatc    2460
ctggacgttg tggcgctgct gtcgaatacg gacatccgcg atgtggacag cattgtgcgg    2520
cacgtgctgc acggcgcgaa gaagctgctg aacgcggaca ggtcatcgat gtttctgctg    2580
gataaggagc gcaatgagct gtacagtaag atggcggaca gcgcgaacga gatccggttt    2640
ccctgcgggc aaggcattgc cggcactgtt gccgagtccg gcgttggcga gaatatcatg    2700
gacgcgtacg ctgactcgcg cttcaacagc gctgtggacc ggcagctggg ctaccgcaca    2760
cagtccatcc tgtgcgagcc gattacgctg aatggcgagg tgcttgccgt ggtgcagctc    2820
gtcaacaagc tcgcgacga cggtagcgtg acctgcttta cacccactga tcaagagacg    2880
tttaaagtgt tctcgctgtt tgcgggcatc tcgatcaaca acagccatct gctggagttc    2940
gcggtgaacg caggtcgtga ggcgatgacc ttgaacctgc agcgtaacag cattacagcg    3000
cagcgtgctc cgaagagtgt gaaggtgatc gcggtgacgc cggaggagcg tgaggcagtg    3060
atgtcgatcg acttcggggg cgcatatgac ttcacttcac cgggcttcaa cctgtttgaa    3120
gtgcgcgaga agtacagcga gccgatggat gcggctgccg gtgttgtgta acctgctca    3180 tggaacagtg gtctacccga gaagtttggc tgccgtgagc agacactgct gaacttcatc    3240
ttgcagtgcc gccgcaggta ccgccgagtg ccgtaccaca acttctacca cgtcgtggac    3300
gtgtgccaga cgctgcacac gtacttgtac acaggcaagg cgtcggagct cctgacagag    3360
ctggagtgct acgtgctgct cgtgacggca ctggtgcacg atcttgacca catgggcgtg    3420
aacaacagct tctacctgaa gacggactcg ccgctaggca tcctctccag cgcgagcggg    3480
aacaactccg tgctggaggt gcaccactgc agcctcgcca tcgagattct gtccgacccc    3540
gccgcggacg tgttcgaggg gctgagcggg caggacgttg cgtatgcgta ccgcgcgctg    3600
atcgattgcg tgctggccac tgatatggct cgccacgggg acttgtcgag ggttttcgat    3660
gatatgcgga aggccggcta cgactctaac gatcaggaat ctcgtcgcct ggtgatggaa    3720
acgctgatca aggccggtga cgtgtcgaat gtgacgaaac cgttcgagac gtcgcgcatg    3780
```

-continued

```
tgggcgatgg ctgtgacgga ggagttctac cgtcagggtg acatggagaa ggagaagggc    3840
gtggaggtgc tgccgatgtt tgaccggtcg aagaacaacg agctggcgcg tgggcagatt    3900
ggcttcatcg acttcgtagc tggcaagttc ttccgggata ttgtgggcaa cctatttcat    3960
ggaatgcagt ggtgtgtgga cacggtaaac tccaaccgcg caaagtggca agagatcctg    4020
gatggccgcc gcgactccat ccgaccctcg attgtttaag gcgtcggtcc cgtggtatcg    4080
ttgatgccgt aatagcgcgc ggtggtgccg ttgctcctgg tgcggaaagt gtctggtaag    4140
tgcaggcgct gtgttgacgt tggcggctgt gcttatctag cgaacgctt gtgtcatgga    4200 tgagcagcag gtttcgagca gcggtgcaat gcgggcgctg gaaggcggaa tgttgcagtg    4260
ttgttggggt gtgtggctac aatgctaagc gtctgtgcgt tggagcttgt tctcatgtgt    4320
tgcttctatg ctacccattg gatgttcaat cgcaaaggtt aagagactgc tgtctgtttt    4380
ttttttgtct gtacaactct tctgcttctt ctctctgtgt tgctgctgct gtcgcctcgc    4440
tgcaccgcca ctcggccccc ttcttccgtg gccccatgcc cgtgcgtacg tgtgcgtgaa    4500
gaggcactgg cggtgtcggc gtccggccca ccccaccccc cggcaggcca cacgcattcg    4560
gagactaccc cctctcgcct ctctcgtttt cgtttcgttt ttggttggtt ctcttgtcgc    4620
tttggttggt cctctgcact gtgcgcttgc tcgtatttat cccttgcctc tgtttcctgt    4680
cggtgtaatc ggatgcacca gccacgtgtg tatgccggtg tctgtaagtg aagaagtcag    4740
agattggtac gcttgtgcac agactcagat acccatatat atgccaataa aatcgattat    4800
tgtatctcgg ccattcacca agccctccct cccctcgcc cactcccatt ccgagtgtgc    4860
tgtactttgt ttcttcctcc ttcttcaatt tctcttcccc cccctcttct cttgatttcg    4920 tcccctccc gcttctcgca cgaaacgaca ggagggcggt gcgatgtggc tgaggccgat    4980
gctggaacac tgggaaaacg ccgcagaaac gtcttggatt tagatctgtc tcaccctccc    5040
ctatacctat ctctcccgcc accagtgtag gcgatggagt gtctattgtg tggtggacgg    5100
tgctcctgtt gggtaaatgg cctgtaggat gttcgaagta cgtgttcttc tcagcacaac    5160
gctggatgtc ctgcgcttgc caccgcgtct gtctcccaca ttctctgtat gtttcacctt    5220
ctctctcccg ttggcacaag gcaggcatcg agcgtgtgcg ttcttttctc ttggcgatgg    5280
cgcacgctct gtgcttcttt tcgtctctgc tcgctgttac cctcccgctg tcagtgcgcc    5340
tctcttgttc tacgacttcg cggctctgtt ccactccccc cccctatct cccccccccc    5400 cacacacaca ccactcccat ctgttcgcgt actatatgct caatgctgag cctgggttcc    5460
aagtggttct cttgctcttc gtcgtccccg tctcgcgctc ttgtctctct tttccgtta    5520 cggtttcctg tctgtcgcca ctttctcggc atccccgacc cgatgtacaa ctcaagcccc    5580
cccctagggc tcacctccgt cttcctcctc cccgaacccc atgtgacgtc gcttctcttc    5640
tctctcccga ttttgtcttc cttttttctc ttttacgatt ggattgcact tcttcgtgct    5700
tccgcgtatg ataggacgcc ggcgtggccc cccccccttc cacctcccgc accttctctc    5760
cgtccctctt cccacgtgta gctgtccgtg cttttgtgcg aagtcgatgc aatccaaacc    5820
aagctgtgtg cgcggaagga gagcgacaga gagagagaga gcgagcgagc ggaactggag    5880
aaggtgccgc tcaccaacag aagaggaaag aggcgggtac gttacaccac gagccaaagc    5940
gaaagaaaag taggacggta ccgcacacac tgccgtacgc ccggagactc gttccctcgc    6000
catgaccgcc gccaaagaag ccgtgttaga gtgaaccaga ttgtttctga gttgctcccc    6060
ggtgtgcttg gctgcggcag cacctctccc ccttcacgtc tgcggcgggc cacgcgcggt    6120
gagagggcgt agacacacca cgcatgggag aagacaaaac atgagatgac gaacacctcg    6180
```

-continued

```
tgcggtgctg aaagcagtgc taagtagcgt ctttaaggca ccccacagga cgactgctct    6240
gtcggcgact tctatccaga tgtgttcatc ctcgtgtacc tctcccttga ttcgcctgtg    6300
ttccacgcac gtgctccacc tcatcatact ttactgatcc tcccctcct  cttccctgc     6360 tctgcgacac cttctcttcg acacttgcca cgacctgtcg gtgcgccctt ctccctcctc    6420
tcgccacgtc ctgccccact tcgacaccct gggaaacttg cacgtgctcg tgcacgcggc    6480
cgtttggcac ctcacccatc tcccacacgc cgacatacat atgcccgct  cctcgcttca    6540 gcaataacag gttaggcata cacacgtaca caagtgcact tccatcacta caactctttt    6600
gacaggacta ccacccttt  acaaccctcc cccaacacga gaaatgactg gagaaatcag    6660
cgagaaggcc ttccctcttt cgacggaccg cctcagccag accatcctcg atctcgtgca    6720
ggaggcgagc aatgccaaga tggtgaagaa aggtgccaac gaggccacca aggccttgaa    6780
ccgcggtatt gcggacctga tagtgttggc gggtgacacg aacccgattg agattctcct    6840
gcacctcccc ctcttgtgcg aagacaagaa cgtcccgtac gtcttcgtgc cgtccaagac    6900
ggcgcttggc cgcgcgtcgc aggtgtctcg caatgtcgtg gcgctagcca tccttcaggg    6960
cgagaacagc cctgttgcgg cgaaggtgca ggcagtgaag ctcgagatcg agcgcttgct    7020
ctgaggtgtt tttccttgct ttctgtttgt aatttttttt tgtatttgcg tgttccctgt    7080
gtttctgttc tcttt                                                     7095
```

<210> SEQ ID NO 5
<211> LENGTH: 940
<212> TYPE: PRT
<213> ORGANISM: Leishmania major

<400> SEQUENCE: 5

```
Met His Ser Ala Val Phe Ser Pro Asp Ala Pro Tyr Cys Gly Ala Ala
 1               5                  10                  15

Gly Ser Asn His Leu Cys Glu Ala Val Ala Leu Cys Gln Ser Ile Leu
                20                  25                  30

Ala Arg Tyr Arg Arg Thr Gly Thr Ser Phe Ser Ser Thr Glu Leu Lys
            35                  40                  45

Ala Ile Gln Ala Leu Arg Thr Glu Phe Pro Asp Thr Ala Gln Glu Pro
        50                  55                  60

Ala Ala Asn Ser Ala Ala Ser Pro Asp Gln Thr Thr Lys Asp Phe Leu
    65                  70                  75                  80

Ser Ile Leu Asp Asp Ala Thr Asp Val Pro His Asn Pro Gln Asn Asp
                85                  90                  95

Ile Val Ala Phe Val Glu Glu Cys Cys Asp Asn Thr Lys Glu Pro Thr
            100                 105                 110

Val Leu Phe Ala Ala Ile Asn Glu Arg Ile Ser Ala Val Thr Cys Ser
        115                 120                 125

Arg Asn Val Arg Thr Tyr Met Val Ile Ala Asn Asn Leu Leu Trp
    130                 135                 140

Asp Pro Val Asn Gly Val Ala Ala Leu Ile Asp Val Thr Pro Leu
145                 150                 155                 160

Gly Lys Cys Ala Gln Ala Arg Asn Met Leu Thr Ile Ala Asn Thr Leu
                165                 170                 175

Tyr Ile Pro Leu Trp Phe Arg Ser Glu Leu Val Gly Cys Val Glu Val
            180                 185                 190

Pro Gly Ala Cys Ile Pro Arg Asp Lys Ala Thr Cys Ala Gln Leu Leu
        195                 200                 205
```

-continued

```
Leu Arg Cys Val Thr Val Ala Val Arg Asn Ser Ile Asn Ile Ser Ile
    210                 215                 220
Arg Lys Arg Glu Ala Asn Lys Ile Glu Ala Met Val Gly Met Ala Thr
225                 230                 235                 240
Arg Leu Ala Arg Asp Thr Leu Glu Glu Ser Val Leu Val Gln Ser Ile
                245                 250                 255
Ile Asn Thr Ala Lys Thr Leu Thr Glu Ser Asp Arg Cys Ser Ile Phe
            260                 265                 270
Leu Val Lys Ala Asp Gly Ser Leu Glu Ala His Phe Glu Asp Gly Asn
        275                 280                 285
Val Val Val Leu Pro Ala Gly Thr Gly Ile Ala Gly His Val Ala Glu
    290                 295                 300
Ser Gly Ala Val Val Asn Ile Pro Asn Ala Tyr Glu Asp Asp Arg Phe
305                 310                 315                 320
His Arg Ser Val Asp Lys Val Thr Gly Tyr His Thr Arg Thr Ile Leu
                325                 330                 335
Cys Leu Pro Ile Ala Phe Glu Gly Thr Ile Ala Val Ala Gln Leu
            340                 345                 350
Ile Asn Lys Leu Asp Met Val Thr Gln Ser Gly Gln Arg Leu Pro Arg
        355                 360                 365
Val Phe Gly Arg Arg Asp Glu Glu Leu Phe Glu Thr Phe Ser Met Phe
    370                 375                 380
Ala Ala Ala Ser Leu Arg Asn Cys Arg Ile Asn Glu Thr Leu Leu Lys
385                 390                 395                 400
Glu Lys Lys Lys Ser Asp Ala Ile Leu Asp Val Val Ala Leu Leu Ser
                405                 410                 415
Asn Thr Asp Ile Arg Asp Val Asp Ser Ile Val Arg His Val Leu His
            420                 425                 430
Gly Ala Lys Lys Leu Leu Asn Ala Asp Arg Ser Ser Met Phe Leu Leu
        435                 440                 445
Asp Lys Glu Arg Asn Glu Leu Tyr Ser Lys Met Ala Asp Ser Ala Asn
    450                 455                 460
Glu Ile Arg Phe Pro Cys Gly Gln Gly Ile Ala Gly Thr Val Ala Glu
465                 470                 475                 480
Ser Gly Val Gly Glu Asn Ile Met Asp Ala Tyr Ala Asp Ser Arg Phe
                485                 490                 495
Asn Ser Ala Val Asp Arg Gln Leu Gly Tyr Arg Thr Gln Ser Ile Leu
            500                 505                 510
Cys Glu Pro Ile Thr Leu Asn Gly Glu Val Leu Ala Val Val Gln Leu
        515                 520                 525
Val Asn Lys Leu Gly Asp Asp Gly Ser Val Thr Cys Phe Thr Pro Met
    530                 535                 540
Asp Arg Glu Thr Phe Gln Val Phe Ser Leu Phe Ala Gly Ile Ser Ile
545                 550                 555                 560
Asn Asn Ser His Leu Leu Glu Phe Ala Val Asn Ala Gly Arg Glu Ala
                565                 570                 575
Met Thr Leu Ser Leu Gln Arg Asn Ser Ile Thr Ala Gln Arg Ala Pro
            580                 585                 590
Lys Ser Val Lys Val Ile Ala Val Thr Pro Glu Glu Arg Glu Ala Val
        595                 600                 605
Met Ser Ile Asp Phe Gly Gly Ala Tyr Asp Phe Thr Ser Pro Gly Phe
    610                 615                 620
```

```
Asn Leu Phe Glu Val Arg Glu Lys Tyr Ser Glu Pro Met Asp Ala Ala
625                 630                 635                 640

Ala Gly Val Val Tyr Asn Leu Leu Trp Asn Ser Gly Leu Pro Glu Lys
            645                 650                 655

Phe Gly Cys Arg Glu Gln Thr Leu Leu Asn Phe Ile Leu Gln Cys Arg
        660                 665                 670

Arg Arg Tyr Arg Arg Val Pro Tyr His Asn Phe Tyr His Val Val Asp
    675                 680                 685

Val Cys Gln Thr Leu His Thr Tyr Leu Tyr Thr Gly Lys Ala Ser Glu
690                 695                 700

Leu Leu Thr Glu Leu Glu Cys Tyr Val Leu Leu Val Thr Ala Leu Val
705                 710                 715                 720

His Asp Leu Asp His Met Gly Val Asn Asn Ser Phe Tyr Leu Lys Thr
                725                 730                 735

Asp Ser Pro Leu Gly Ile Leu Ser Ser Ala Ser Gly Asn Asn Ser Val
            740                 745                 750

Leu Glu Val His His Cys Ser Leu Ala Ile Glu Ile Leu Ser Asp Pro
        755                 760                 765

Ala Ala Asp Val Phe Glu Gly Leu Ser Gly Gln Asp Val Ala Tyr Ala
    770                 775                 780

Tyr Arg Ala Leu Ile Asp Cys Val Leu Ala Thr Asp Met Ala Lys His
785                 790                 795                 800

Ala Asp Ala Leu Ser Arg Phe Thr Glu Leu Ala Thr Ser Gly Phe Glu
                805                 810                 815

Lys Asp Asn Asp Thr His Arg Arg Leu Val Met Glu Thr Leu Ile Lys
            820                 825                 830

Ala Gly Asp Val Ser Asn Val Thr Lys Pro Phe Glu Thr Ser Arg Met
        835                 840                 845

Trp Ala Met Ala Val Thr Glu Glu Phe Tyr Arg Gln Gly Asp Met Glu
    850                 855                 860

Lys Glu Lys Gly Val Glu Val Leu Pro Met Phe Asp Arg Ser Lys Asn
865                 870                 875                 880

Asn Glu Leu Ala Arg Gly Gln Ile Gly Phe Ile Asp Phe Val Ala Gly
                885                 890                 895

Lys Phe Phe Arg Asp Ile Val Gly Asn Leu Phe His Gly Met Gln Trp
            900                 905                 910

Cys Val Asp Thr Val Asn Ser Asn Arg Ala Lys Trp Gln Glu Ile Leu
        915                 920                 925

Asp Gly Arg Arg Asp Ser Ile Arg Ser Ser Ile Val
    930                 935                 940

<210> SEQ ID NO 6
<211> LENGTH: 6945
<212> TYPE: DNA
<213> ORGANISM: Leishmania major

<400> SEQUENCE: 6
acaggcaggt gcgtgtggag aggttgaagg acaaggttca tccacagctc agtgccgcca      60
agccggtgct caagttgaat gcggctcccg cgccgttgtg caagaagaat ccactgtcag     120
ccccagtgcc tttgaagaag gtgccagcaa tggtaaagcc gcaacggaag cggacgctgc     180
cgatcgtcac caagacaact gcgagaaagg ccgcaccggt ggcgtctcct gatagaaatg     240
ccccgccggc agtgacgctt cagctggtca ccaagcgagc tgccggcgtt cccgcactg      300 aaacgaaggg tgtgcccgcc tcctgccgag cccgcgtgaa ggtcagcgcg gcccaaaagg     360
```

```
tagccgcggc cgctaccaag aaggcgctca agaagggtac atccacctca caggcgacaa     420
ccgccacaga cgagggtggg gacttcttcg ccgaggattt catggcggaa ggtgaaggag     480
acgacgtcgg gctcgaggtt gccgacaagt ccgctggtga cacgaacgcg caagtagcag     540
cgcccacggc gccagtgaag cagaagcgta agtccgccgg gcgtcgtgca gctcgcagtc     600
acctccttgc acccgagtcg atgctccctg cgacggcacg gtcacagaag gtgattgtgg     660
cgcacacccc cacgtgtaga aaggcaccgc ggccggtgtg cacctcccca tcatcccact     720
ttactcctgc acgacgcaag gtgagccttg ccgacaacat ccgcgctcag ctggccagtt     780
ttttgtagtc actgggtcgc gtgcgtggtg ccgaacgcgg ggaacggctt gacctacctc     840
ttcacgcgcg ctgaacaaca tatagagaaa acactagatg ccacccttc ctctcctctc      900 ccagctgccc ttcccctgct ccccatcgac catgcgtgaa ggttgtcccc accacctcgt     960
atctgtccag cggtggcatg ataatggcgg cagatttgag ctgacttgga gaatggcaag    1020
acaggaaagc gggggggggg gggcaaaaga agagatagag gggagagcgt atgaggggggg    1080 ggggcggcgg acgcgcacac actcatctgc tcgtgagggc acgtaacgcc ctagcaaatg    1140
ttttgcatag acaagggaag gacaaagcgc catcgatacc ggagagcaat acagactcac    1200
atacatacat acatgcgaac gcctacgcgc gtcccgcaca tgaggacagc cgaataagtc    1260
tgcggtgtta cctcaaagaa aaaggcacag gaggcacaat cgagacagca gctgtgctgt    1320
ctcggttgcg gtacgagtg ttccgcccac gtcgtttct gcacatccct tcacgattgt       1380
gctgcgggtg cgctcgtgtg actcattgtc gaaacacgtc agagcagctg ccggccacaa    1440
cagtaccccg ctggcgcggc tggcgagacg cggggacatc acgtgtcagt atggtgccac    1500
caagcgaaga gggagggaga ggcgaagggc tgagatgacg gatctgctac tgaatgcgcg    1560
aagagcgggc gtgtggtacg tggaggatag ccgcccaagt tgaacgttac ggctcgatct    1620
tctccgtgaa gaaacggtgc gcgttctcct tttccgctgc cgtttctttc tctccctgta    1680
tgcctcgcca tcatgtatca ttacggatgt cctgtcctgc cccacttctt cctgccttc     1740 tcgcctacca actactgaac gctgtcagtg cgcctctcgc ttctccagct ccacacgcgc    1800
tcactggcca tcatcaaagg gaagccacca tcggcaccca aggagcttaa ccagcatttg    1860
aggttcttca aaaggcggtg tgaggtgcag ctgcactgga tcattcgggg gacacaaacg    1920
cgcatgcgtg cacggctgca cacgggaccc gtcattgtct cttccgctct gttgctcctg    1980
tcgccgctct ccacagcgac acacatacac acacagtcag acacacacac acacacacac    2040
acacacacac acacacaagc gagccccata cacgcaaacg ccacgcggcc tctttgttgt    2100
tcgtttgttc actcttgttt ttcggctcgt attggccgct gtcttcgatt tgttatcaac    2160
tggcagtgac gccgtacagc gatgcattca gcggtctttt cccccgatgc gccgtattgc    2220
ggcgcagccg gctccaatca cctatgtgag gcggttgcac tctgccagtc gattctggcg    2280
cgctaccgtc ggactggtac atccttctcc tccacagagc tgaaggcgat tcaagccctg    2340
cgcaccgagt tccctgatac cgcgcaagag ccggctgcga atagcgcggc ttcacccgac    2400
cagaccacga aggacttcct gagcattctt gacgatgcaa ccgacgtgcc gcacaaccca    2460
cagaacgaca ttgtcgcgtt tgtggaggag tgctgcgaca acaccaagga gccaacagta    2520
ttgtttgcgg cgattaatga gcgcatttca gccgtgactt gctcgcgtaa tgtccgcacg    2580
tacatggtga tcgcaaacga caatctccta tgggaccctg tcaacggtgt tgccgccctt    2640
atcgacgacg tcacgccctt gggcaagtgc gcgcaagcgc gcaacatgct gacgattgcc    2700
```

```
aacaccctat acatccccct ctggtttcgg tccgagctcg ttggctgcgt ggaggtgccg    2760
ggtgcctgca tcccaaggga caaggctacc tgtgctcagc ttctgctccg gtgcgtcacc    2820
gttgccgttc gaaacagcat caacatctcc atcagaaaga gggaagcaaa taagatcgag    2880
gccatggtgg gcatggcgac acggcttgct cgagacacgt tggaggagtc ggtgctggtg    2940
cagtccatca tcaacacggc aaagacgctg acggagagcg accggtgtag catcttcctg    3000
gtgaaagcgg acggcagcct ggaggcgcac ttcgaggacg gcaacgttgt ggtgctgcct    3060
gcggggacgg gcatcgcagg tcacgttgcg gaatctggcg ccgtggtgaa catcccgaac    3120
gcgtacgagg acgaccggtt ccaccggtcc gtggacaagg tgactggcta ccacacgcgc    3180
acgatcttgt gtctgccgat cgcgttcgag ggcacgatcg ttgccgttgc gcagctgatc    3240
aacaagctgg acatggtgac acagagcggg cagcggcttc cgcgcgtgtt tggacggcgc    3300
gacgaggagc tgttcgagac gttctcgatg ttcgctgcgg cgtcgctgcg caactgccgc    3360
atcaacgaga cgctgctgaa ggagaagaag aagagcgacg cgatcctgga cgttgtggcg    3420
ctgctgtcga atacggacat ccgcgatgtg acagcattg tgcggcacgt gctgcacggc    3480
gcgaagaagc tgctgaacgc ggacaggtca tcgatgtttc tgctggataa ggagcgcaat    3540
gagctgtaca gtaagatggc ggacagcgcg aacgagatcc ggtttccctg cgggcaaggc    3600
attgccggca ctgttgccga gtccggcgtt ggcgagaata tcatggacgc gtacgctgac    3660
tcgcgcttca acagcgctgt ggaccggcag ctgggctacc gcacacagtc catcctgtgc    3720
gagccgatta cgctgaatgg cgaggtgctt gccgtggtgc agctcgtcaa caagctcggc    3780
gacgacggta gcgtgacctg ctttacaccc atggaccggg aaacgttcca agtgttctcg    3840
ctgtttgcgg gcatctcgat caacaacagc catctgctgg agttcgcggt gaacgcaggt    3900
cgtgaggcga tgaccttgag cctgcagcgc aacagcatta cagcgcagcg tgctccgaag    3960
agtgtgaagg tgatcgcggt gacgccggag gagcgtgagg cagtgatgtc gatcgacttc    4020
gggggcgcat atgacttcac ttcaccgggc ttcaacctgt ttgaagtgcg cgagaagtac    4080
agcgagccga tggatgcggc tgccggtgtt gtgtataacc tgctatggaa cagtggtcta    4140
cccgagaagt ttggctgccg tgagcagaca ctgctgaact tcatcttgca gtgccgccgc    4200
aggtaccgcc gagtgccgta ccacaacttc taccacgtcg tggacgtgtg ccagacgctg    4260
cacacgtact tgtacacagg caaggcgtcg gagctcctga cagagctgga gtgctacgtg    4320
ctgctcgtga cggcactggt gcacgatctt gaccacatgg gcgtgaacaa cagcttctac    4380
ctgaagacgg actcgccgct aggcatcctc tccagcgcga gcgggaacaa ctccgtgctg    4440
gaggtgcacc actgcagcct cgccatcgag attctgtccg accccgccgc ggacgtgttc    4500
gaggggctga gcgggcagga cgttgcgtat gcgtaccgcg cgctgatcga ttgcgtgctg    4560
gccactgata tggcgaagca cgctgacgcg ctaagtcgct tcacagagtt ggcgacaagc    4620
gggtttgaga aagacaacga cacccaccgt cgcctggtga tggaaacgct gatcaaggcc    4680
ggtgacgtgt cgaatgtgac gaaaccgttc gagacgtcgc gcatgtgggc gatggctgtg    4740
acggaggagt tctaccgtca gggtgacatg gagaaggaga agggcgtgga ggtgctgccg    4800
atgtttgacc ggtcgaagaa caacgagctg gcgcgtgggc agattggctt catcgacttc    4860
gtagctggca agttcttccg ggatattgtg gcaacctat ttcatggaat gcagtggtgt    4920
gtggacacgg taaactccaa ccgcgcaaag tggcaagaga tcctggatgg ccgccgcgac    4980
tccatccgat cctcgattgt ttaaggcatc ggtcccgcgg tatcgttgat gccgtaatag    5040
cgcgcggaag tactcacggc gaatgtcttt cgagaagtga aagcggtgag ctcacttgtc    5100
```

-continued

```
actatggacg gatgagtgcc gttggtcgcc gctctgctgt gcgtgtctac gcgtcttatc    5160
cccacctcag tatgtgcacc gggccgtcat ttcccttgt acccgtcgct gtatccgcga     5220
cgcgggatgg tttgtgtgtt ggtgagtctc cctctctctg caccagggcc tgttctggtt    5280
gatgggcgcc tctcgcactg ctgaggacaa ggtgtggcac atgtgggcgt gtgagtcgtg    5340
tttttttttt ttggctctcg tcttgtctcc tctctcctcg ctattagccc ttttctgaac    5400
agacctctct ctctctctct gctcgtcttt cggaggagtg gtttgccgtt gaaggctgaa    5460
cggtacgaag ggggaggagt gagcagtgca ggtgcacaca cacgcaccac acctaattct    5520
ctcttcatcc gcctttcctt tttttccggt gtgtgtcccg aagatggttt cctgtctttg    5580
catccgtttc tctcccctt tttcgtgtg tctgtctttt gttgttcgtc acgaatctca      5640
cccgcctccc tccccctct cccattttt ctctcgtagg tgtgtgcatc tgtgctcctg      5700
gtgagacgga gtggagtggg ggcaccccgc agcgcgtggc atctctcccc cccccaggt     5760
gggggtcat tcgtgcaccc aaactctgtc tctgggagg aagctcagcg gcgcacccc       5820
accccaccc ccaccctctc cctcctatat ccctgccagt gcggaaccgc ttctcctggc     5880
gacagggtca agcacctata acgcagggag gacagagcaa gatgtcgctg cggatgtcgg    5940
ccgtcaggtg ccggatggcg tggcgccgga gcgacctgcg acagcgcaca cgcacgattc    6000
atgtgatggg cagagtgccg gcgtgactcg aacgcatccc acccccggcc ctcacactgt    6060
cctgctgctg tggggagcct gtgccatcgc gatggaatcg caccgtgtgg cgaccggcac    6120
aacgtgagcg gctgtggggc gacctgtgag gcggggtggg tgggtgggtg gcgggtagag    6180
ttcgaggctg aggctgtgcc ctcagatggc cgagttggcg cgttgcggtc acgtgtgtct    6240
ctgcagctgc ttcgcaccag gcgatagagg cctgtgacag ggccggtgca agagtggggc    6300
tcgacctcat gttgcatgac agagaaatga acatgctgta actcccctct ccttgactca    6360
tttccatctc ttgtgtcacc tactacctgt ccttctcagt gtcttggtgc acttgtgacg    6420
ttctcgcgtg tctcctcttt tcttttcttc tcgaagtttt ttgggtctgc agagagaggc    6480
gatgggagga ggagcagcca ggcttgcgtt gtgtgatgtc gagaagaaca atgtaacagc    6540
tcttctctcg ttgtcctcct tcctcccgct tctgttcggc gaggaaaaca gcagacttgt    6600
gtagcacaag atgctgctgg cgcctgctgt gtgacatgtg cgaggaagcc tcgcgcaaac    6660
cgtttgtggt ctctggaggg ggtactgcga gcgggaggac agggcgaggc aacgtgtgcg    6720
agataaggtc gtggcacaga gaggatacgg ctatgagagg gctgtgtgct gttggtgttt    6780
cctcaacgtt cgtgctaaag gtccgtccaa aggtgaggaa gttgggacga ggaagcatgc    6840
atggacggtc tcgtggcctc atcacctcct ttcggtgcca tcattaccac ccctcgctcc    6900
tgcttttcg ccgccatgcc cagcgggact ttttttcgtc tgttc                    6945
```